United States Patent
Chait et al.

(10) Patent No.: US 11,988,665 B2
(45) Date of Patent: *May 21, 2024

(54) SYSTEMS AND METHODS FOR DETERMINING VIRUSES SUCH AS CORONAVIRUSES

(71) Applicant: Analiza, Inc., Cleveland, OH (US)

(72) Inventors: Arnon Chait, Bay Village, OH (US); Boris Y. Zaslavsky, Solon, OH (US)

(73) Assignee: Analiza, Inc., Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/800,296

(22) PCT Filed: Feb. 26, 2021

(86) PCT No.: PCT/US2021/019795
§ 371 (c)(1),
(2) Date: Aug. 17, 2022

(87) PCT Pub. No.: WO2021/173915
PCT Pub. Date: Sep. 2, 2021

(65) Prior Publication Data
US 2023/0088162 A1    Mar. 23, 2023

Related U.S. Application Data

(60) Provisional application No. 63/091,849, filed on Oct. 14, 2020, provisional application No. 63/071,472, filed on Aug. 28, 2020, provisional application No. 63/003,843, filed on Apr. 1, 2020, provisional application No. 63/000,441, filed on Mar. 26, 2020, provisional application No. 62/987,385, filed on Mar. 10, 2020, provisional application No. 62/982,880, filed on Feb. 28, 2020.

(51) Int. Cl.
*G01N 33/569* (2006.01)
*C12Q 1/6888* (2018.01)
*C12Q 1/70* (2006.01)
*G01N 33/49* (2006.01)

(52) U.S. Cl.
CPC ..... *G01N 33/56983* (2013.01); *C12Q 1/6888* (2013.01); *C12Q 1/70* (2013.01); *G01N 33/491* (2013.01); *G01N 2333/11* (2013.01); *G01N 2333/165* (2013.01)

(58) Field of Classification Search
None
See application file for complete search history.

(56) References Cited

U.S. PATENT DOCUMENTS

| 7,968,350 | B2 | 6/2011 | Chait et al. |
| 8,099,242 | B2 | 1/2012 | Chait et al. |
| 11,535,902 | B2 | 12/2022 | Chait et al. |
| 2014/0065642 | A1* | 3/2014 | Chait ............... G01N 33/57434 435/7.92 |
| 2015/0219655 | A1 | 8/2015 | Chait et al. |
| 2021/0364517 | A1 | 11/2021 | Rotkin et al. |
| 2023/0088162 | A1 | 3/2023 | Chait et al. |

FOREIGN PATENT DOCUMENTS

| WO | WO 2004/111655 A1 | 12/2004 |
| WO | WO 2019/144966 A1 | 8/2019 |
| WO | WO2019144966 | * 8/2019 |
| WO | WO 2021/173915 A1 | 9/2021 |
| WO | WO 2021/185336 A1 | 9/2021 |

OTHER PUBLICATIONS

COVID-19 sequence (Year: 2020).*
Invitation to Pay Additional Fees dated Jun. 18, 2021, for International Application No. PCT/US2021/019795.
International Search Report and Written Opinion dated Aug. 11, 2021, for International Application No. PCT/US2021/019795.
International Preliminary Report on Patentability dated Sep. 9, 2022, for International Application No. PCT/US2021/019795.
International Search Report and Written Opinion dated Jul. 5, 2022, for International Application No. PCT/US2022/020484.
Cheung et al., A one-pot, isothermal DNA sample preparation and amplification platform utilizing aqueous two-phase systems. Anal Bioanal Chem. Aug. 2018;410(21):5255-5263. doi: 10.1007/s00216-018-1178-4. Epub Jun. 8, 2018.
Iqbal et al., Aqueous two-phase system (ATPS): an overview and advances in its applications. Biol Proced Online. Oct. 28, 2016;18:18.
Jue et al., Using an aqueous two-phase polymer-salt system to rapidly concentrate viruses for improving the detection limit of the lateral-flow immunoassay. Biotechnol Bioeng. Dec. 2014;111(12):2499-507. doi: 10.1002/bit.25316. Epub Aug. 25, 2014.

(Continued)

*Primary Examiner* — Shanon A. Foley
*Assistant Examiner* — Myron G Hill
(74) *Attorney, Agent, or Firm* — Wolf, Greenfield & Sacks, P.C.

(57) ABSTRACT

Certain aspects of the present disclosure generally relate to systems and methods for determining viruses. For instance, some aspects are directed to systems and methods for determining viruses using a partitioning system. Within the partitioning system, the virus may partition into one or more phases. In some cases, a virus-binding moiety facilitates partitioning of the virus. The phases may be assayed to determine the virus based on, e.g., quantitative or qualitative assessments of the distribution of virus-binding and/or signaling moieties. The virus-binding moiety may be attached to particles that may form a complex around a virus. The complex may be detectable without a signaling moiety (e.g., as a color change) in some embodiments. In some cases, more than one virus may be determined. For example, a virus-binding moiety may substantially alter the partitioning behavior of one virus or complex, relative to another, by being selective for the first virus.

20 Claims, 22 Drawing Sheets

(56) References Cited

OTHER PUBLICATIONS

Paz et al., A simplified SARS-CoV-2 detection protocol for research laboratories. PLoS One. Dec. 18, 2020;15(12):e0244271.

* cited by examiner

Controls

Virus mixture

Controls

Virus mixture

SYSTEMS AND METHODS FOR DETERMINING VIRUSES SUCH AS CORONAVIRUSES

RELATED APPLICATIONS

This application is a national stage filing under 35 U.S.C. § 371 of International Application No. PCT/US2021/019795, filed Feb. 26, 2021, entitled "Systems and Methods for Determining Viruses Such as Coronaviruses," which claims the benefit of U.S. Pat. Apl. Ser. No. 62/982,880, filed Feb. 28, 2020, entitled "Systems and Methods for Determining Viruses such as Coronaviruses"; U.S. Pat. Apl. Ser. No. 62/987,385, filed Mar. 10, 2020, entitled "Systems and Methods for Determining Viruses such as Coronaviruses"; U.S. Pat. Apl. Ser. No. 63/071,472, filed Aug. 28, 2020, entitled "Systems and Methods for Determining Viruses such as Coronaviruses"; U.S. Pat. Apl. Ser. No. 63/091,849, filed Oct. 14, 2020, entitled "Systems and Methods for Determining Viruses such as Coronaviruses"; U.S. Pat. Apl. Ser. No. 63/000,441, filed Mar. 26, 2020, entitled "Determination of Viruses such as Coronaviruses Based on Viral Proteins"; and U.S. Pat. Apl. Ser. No. 63/003,843, filed Apr. 1, 2020, entitled "Determination of Viruses such as Coronaviruses Based on Viral Proteins." Each of the above is incorporated herein by reference in its entirety.

FIELD

Certain aspects of the present disclosure generally relate to systems and methods for determining viruses such as coronaviruses.

BACKGROUND

Coronaviruses are a group of viruses that cause diseases in mammals and birds. In humans, coronaviruses cause respiratory tract infections that are typically mild, such as the common cold, though rarer forms such as SARS, MERS and COVID-19 can be lethal. Coronaviruses are enveloped viruses with a positive-sense single-stranded RNA genome and a nucleocapsid of helical symmetry. The genome size of coronaviruses ranges from approximately 27 to 34 kilobases. The name coronavirus is derived from the Latin corona, meaning "crown" or "halo," which refers to the characteristic appearance of the virus particles: they have a fringe reminiscent of a crown or of a solar corona.

SUMMARY

Certain aspects of the present disclosure generally relate to systems and methods for determining viruses such as coronaviruses. The subject matter of the present disclosure involves, in some cases, interrelated products, alternative solutions to a particular problem, and/or a plurality of different uses of one or more systems and/or articles.

For example, some aspects of the present disclosure generally relate to systems and methods for determining viruses. For instance, some aspects are directed to systems and methods for determining viruses using a partitioning system. Within the partitioning system, the virus may partition into one or more phases. In some cases, a virus-binding moiety facilitates partitioning of the virus. The phases may be assayed to determine the virus based on, e.g., quantitative or qualitative assessments of the distribution of virus-binding and/or signaling moieties. The virus-binding moiety may be attached to particles that may form a complex around a virus. The complex may be detectable without a signaling moiety (e.g., as a color change) in some embodiments. In some cases, more than one virus may be determined. For example, a virus-binding moiety may substantially alter the partitioning behavior of one virus or complex, relative to another, by being selective for the first virus.

One aspect is generally directed to a method comprising partitioning a biological fluid in an aqueous multi-phase partitioning system, wherein the biological fluid arises from a subject suspected of being infected with a virus, and wherein the aqueous multi-phase partitioning system comprises an agent comprising a signaling moiety and a virus-binding moiety; and determining the signaling moiety within the phases of the partitioning system.

Another aspect is generally directed to a method comprising partitioning a biological fluid in a partitioning system, wherein the biological fluid arises from a subject suspected of being infected with a virus, and wherein the partitioning system comprises an agent comprising a signaling moiety and a virus-binding moiety; and determining the signaling moiety within the phases of the partitioning system.

Yet another aspect is generally directed to a method of distinguishing a first virus and a second virus, comprising partitioning a fluid in an aqueous multi-phase partitioning system, wherein the fluid is suspected of containing the first virus and/or the second virus, and wherein the fluid comprises a targeting species able to selectively bind to the first virus or the second virus, relative to the other; and determining a distribution of the first virus and the second virus within the partitioning system, wherein the first virus exhibits a first partitioning behavior, and the second virus exhibits a second partitioning behavior distinguishable from the first virus.

One aspect is generally directed to a method comprising partitioning a biological fluid in a first aqueous multi-phase partitioning system, wherein the biological fluid arises from a subject suspected of being infected with a virus; partitioning fluid from a phase of the first aqueous multi-phase partitioning system into a second aqueous multi-phase partitioning system; and determining a virus within the second aqueous multi-phase partitioning system.

Another aspect is generally directed to a method comprising partitioning a biological fluid in an aqueous multi-phase partitioning system, wherein the biological fluid arises from a subject suspected of being infected with a virus; and determining the virus in at least one phase of the partitioning system using an agent comprising a signaling moiety and a virus-binding moiety.

Still another aspect is generally directed to a method comprising partitioning a biological fluid in an aqueous multi-phase partitioning system, wherein the biological fluid arises from a subject suspected of being infected with a virus; releasing nucleic acid from the virus into the partitioning system; determining the nucleic acid in a phase of the partitioning system; removing at least a portion of the phase containing the virus from the partitioning system; and sequencing the nucleic acid within the phase removed from the partitioning system.

Yet another aspect is generally directed to a method comprising partitioning a biological fluid in an aqueous multi-phase partitioning system, wherein the biological fluid arises from a subject suspected of being infected with a virus; determining a nucleic acid associated with the virus in at least one phase of the partitioning system; and sequencing the nucleic acid.

In one aspect, the method is generally directed to partitioning a biological fluid in an aqueous multi-phase partitioning system, wherein the biological fluid arises from a subject suspected of being infected with a virus; releasing nucleic acid from the virus into the partitioning system; removing at least a portion of the phase containing the virus from the partitioning system; and determining the virus by sequencing the nucleic acid within the phase removed from the partitioning system.

In another aspect, the method is generally directed to partitioning a biological fluid in an aqueous multi-phase partitioning system, wherein the biological fluid arises from a subject suspected of being infected with a virus, and wherein the aqueous multi-phase partitioning system comprises an agent comprising a binding moiety specific for the virus; and determining the virus within at least one phase of the partitioning system.

In yet another aspect, the method is generally directed to partitioning a biological fluid in a partitioning system, wherein the biological fluid arises from a subject suspected of being infected with a virus, and wherein the partitioning system comprises an agent comprising a binding moiety specific for the virus; and determining the virus within the phases of the partitioning system.

In still another aspect, the method is generally directed to partitioning a biological fluid in an aqueous multi-phase partitioning system, wherein the biological fluid arises from a subject suspected of being infected with a virus; and determining the virus in at least one phase of the partitioning system using an agent comprising a binding moiety specific for the virus.

The method, in one aspect, comprises partitioning a biological fluid in an aqueous multi-phase partitioning system, wherein the biological fluid arises from a subject suspected of being infected with a SARS-CoV-2 virus, wherein the aqueous multi-phase partitioning system comprises an agent comprising a gold nanoparticle and an antibody able to specifically bind a spike protein of the SARS-CoV-2 virus, and wherein at least 50% of the gold nanoparticles partitions in a single phase of the partitioning system when the SARS-CoV-2 virus is present; and within 10 minutes of partitioning, determining the partitioning of the gold nanoparticles by determining a change in color in at least one phase of the partitioning system.

The method, in another aspect, is a method of distinguishing a first virus and a second virus. In one set of embodiments, the method comprises partitioning a fluid in a partitioning system, wherein the fluid is suspected of containing the first virus and/or the second virus, and wherein the fluid comprises a targeting species able to selectively bind to the first virus or the second virus, relative to the other; and determining a distribution of the first virus and the second virus within the partitioning system, wherein the first virus exhibits a first partitioning behavior, and the second virus exhibits a second partitioning behavior distinguishable from the first virus.

The method, in still another aspect, comprises partitioning a biological fluid in a first partitioning system, wherein the biological fluid arises from a subject suspected of being infected with a virus; partitioning fluid from a phase of the first partitioning system into a second partitioning system; and determining a virus within the second partitioning system.

The method, in yet another aspect, comprises partitioning a biological fluid in a partitioning system, wherein the biological fluid arises from a subject suspected of being infected with a virus; and determining the virus in at least one phase of the partitioning system using an agent comprising a signaling moiety and a virus-binding moiety.

According to one aspect, the method comprises partitioning a biological fluid in a partitioning system, wherein the biological fluid arises from a subject suspected of being infected with a virus; releasing nucleic acid from the virus into the partitioning system; determining the nucleic acid in a phase of the partitioning system; removing at least a portion of the phase containing the virus from the partitioning system; and sequencing the nucleic acid within the phase removed from the partitioning system.

According to another aspect, the method comprises partitioning a biological fluid in a partitioning system, wherein the biological fluid arises from a subject suspected of being infected with a virus; determining a nucleic acid associated with the virus in at least one phase of the partitioning system; and sequencing the nucleic acid.

According to yet another aspect, the method comprises partitioning a biological fluid in a partitioning system, wherein the biological fluid arises from a subject suspected of being infected with a virus; releasing nucleic acid from the virus into the partitioning system; removing at least a portion of the phase containing the virus from the partitioning system; and determining the virus by sequencing the nucleic acid within the phase removed from the partitioning system.

According to still another aspect, the method comprises partitioning a biological fluid in a partitioning system, wherein the biological fluid arises from a subject suspected of being infected with a virus, and wherein the aqueous multi-phase partitioning system comprises an agent comprising a binding moiety specific for the virus; and determining the virus within at least one phase of the partitioning system.

In accordance with one aspect, the method comprises partitioning a biological fluid in a multi-phase partitioning system, wherein the biological fluid arises from a subject suspected of being infected with a virus; removing at least a portion of one phase of the partition system; releasing nucleic acid from the virus into the portion of the one phase; and determining the nucleic acid in the phases of the partition system.

In accordance with another aspect, the method comprises partitioning a biological fluid in a multi-phase partitioning system, wherein the biological fluid arises from a subject suspected of being infected with a virus; removing an aliquot from one phase of the partition system; releasing nucleic acid from the virus into the portion of the aliquot; and determining the nucleic acid in the phases of the partition system.

In accordance with yet another aspect, the method comprises partitioning a biological fluid in a multi-phase partitioning system, wherein the biological fluid arises from a subject suspected of being infected with a virus; removing aliquots from each of the phases of the partition system; releasing nucleic acid from the virus into the aliquots; and determining the nucleic acid in the aliquots of the partition system.

Another aspect is generally directed to a method, comprising partitioning a biological fluid in an aqueous multi-phase partitioning system, wherein the biological fluid arises from a subject is suspected of being infected with a virus, and wherein the aqueous multi-phase partitioning system comprises an agent comprising a particle and a virus-binding moiety; and determining the particle within the phases of the partitioning system.

Still another aspect is generally directed to a method, comprising partitioning a biological fluid in a partitioning system, wherein the biological fluid arises from a subject is suspected of being infected with a virus, and wherein the partitioning system comprises an agent comprising a particle and a virus-binding moiety; and determining the particle within the phases of the partitioning system.

Yet another aspect is generally directed to a method, comprising exposing a biological fluid arising from a subject suspected of being infected with a virus to an agent comprising a particle and a virus-binding moiety; partitioning the biological fluid in an aqueous multi-phase partitioning system; and determining the particle within the phases of the partitioning system.

Still another aspect is generally directed to a composition comprising an aqueous multi-phase partitioning system, comprising an agent comprising a signaling moiety and a virus-binding moiety, and a targeting species able to bind to a virus.

In another aspect, the composition comprises an aqueous multi-phase partitioning system, comprising an agent comprising a particle and a virus-binding moiety, and a targeting species able to bind to a virus.

Yet another aspect is generally directed to a composition comprising a partitioning system, comprising an agent comprising a signaling moiety and a virus-binding moiety, and a targeting species able to bind to a virus.

One aspect is generally directed to a method comprising partitioning a biological fluid in an aqueous multi-phase partitioning system, wherein the biological fluid arises from a subject, and wherein the aqueous multi-phase partitioning system comprises an agent comprising a signaling moiety and a virus-binding moiety; and determining the signaling moiety within the phases of the partitioning system.

Another aspect is generally directed to a method comprising partitioning a biological fluid in a partitioning system, wherein the biological fluid arises from a subject, and wherein the partitioning system comprises an agent comprising a signaling moiety and a virus-binding moiety; and determining the signaling moiety within the phases of the partitioning system.

Yet another aspect is generally directed to a method of distinguishing a first virus and a second virus comprising partitioning a fluid in an aqueous multi-phase partitioning system, wherein the fluid comprises a targeting species able to selectively bind to a first virus or a second virus, relative to the other; and determining a distribution of the first virus and the second virus within the partitioning system, wherein the first virus exhibits a first partitioning behavior, and the second virus exhibits a second partitioning behavior distinguishable from the first virus.

One aspect is generally directed to a method comprising partitioning a biological fluid in a first aqueous multi-phase partitioning system; partitioning fluid from a phase of the first aqueous multi-phase partitioning system into a second aqueous multi-phase partitioning system; and determining a virus arising from the biological fluid within the second aqueous multi-phase partitioning system.

Another aspect is generally directed to a method comprising partitioning a biological fluid in an aqueous multi-phase partitioning system, and determining a virus arising from the biological fluid in at least one phase of the partitioning system using an agent comprising a signaling moiety and a virus-binding moiety.

Still another aspect is generally directed to a method comprising partitioning a biological fluid in an aqueous multi-phase partitioning system; releasing nucleic acid from a virus within the biological fluid into the partitioning system; determining the nucleic acid in a phase of the partitioning system; removing at least a portion of the phase containing the virus from the partitioning system; and sequencing the nucleic acid within the phase removed from the partitioning system.

Yet another aspect is generally directed to a method comprising: partitioning a biological fluid in an aqueous multi-phase partitioning system; determining a nucleic acid associated with a virus arising from the biological fluid in at least one phase of the partitioning system; and sequencing the nucleic acid.

In one aspect, the method is generally directed to partitioning a biological fluid in an aqueous multi-phase partitioning system; releasing nucleic acid from a virus arising from the biological fluid into the partitioning system; removing at least a portion of the phase containing the virus from the partitioning system; and determining the virus by sequencing the nucleic acid within the phase removed from the partitioning system.

In another aspect, the method is generally directed to partitioning a biological fluid in an aqueous multi-phase partitioning system, wherein the aqueous multi-phase partitioning system comprises an agent comprising a binding moiety specific for a virus within the biological fluid; and determining the virus within at least one phase of the partitioning system.

In yet another aspect, the method, is generally directed to partitioning a biological fluid in a partitioning system, wherein the partitioning system comprises an agent comprising a binding moiety specific for a virus within the biological fluid; and determining the virus within the phases of the partitioning system.

In still another aspect, the method is generally directed to partitioning a biological fluid in an aqueous multi-phase partitioning system; and determining a virus arising from the biological fluid in at least one phase of the partitioning system using an agent comprising a binding moiety specific for the virus.

The method, in one aspect, comprises partitioning a biological fluid in an aqueous multi-phase partitioning system, wherein the aqueous multi-phase partitioning system comprises an agent comprising a gold nanoparticle and an antibody able to specifically bind a spike protein of a SARS-CoV-2 virus, and wherein at least 50% of the gold nanoparticles partitions in a single phase of the partitioning system when the SARS-CoV-2 virus is present; and within 10 minutes of partitioning, determining the partitioning of the gold nanoparticles by determining a change in color in at least one phase of the partitioning system.

The method, in another aspect, is a method of distinguishing a first virus and a second virus. In one set of embodiments, the method comprises partitioning a fluid in a partitioning system wherein the fluid comprises a targeting species able to selectively bind to a first virus or a second virus, relative to the other; and determining a distribution of the first virus and the second virus within the partitioning system, wherein the first virus exhibits a first partitioning behavior, and the second virus exhibits a second partitioning behavior distinguishable from the first virus.

The method, in still another aspect, comprises partitioning a biological fluid in a first partitioning system; partitioning fluid from a phase of the first partitioning system into a second partitioning system; and determining a virus arising from the biological fluid within the second partitioning system.

The method, in yet another aspect, comprises partitioning a biological fluid in a partitioning system; and determining a virus arising from the biological fluid in at least one phase of the partitioning system using an agent comprising a signaling moiety and a virus-binding moiety.

According to one aspect, the method comprises partitioning a biological fluid in a partitioning system; releasing nucleic acid from a virus arising from the biological fluid into the partitioning system; determining the nucleic acid in a phase of the partitioning system; removing at least a portion of the phase containing the virus from the partitioning system; and sequencing the nucleic acid within the phase removed from the partitioning system.

According to another aspect, the method comprises partitioning a biological fluid in a partitioning system; determining a nucleic acid associated with a virus arising from the biological fluid in at least one phase of the partitioning system; and sequencing the nucleic acid.

According to yet another aspect, the method comprises partitioning a biological fluid in a partitioning system; releasing nucleic acid from a virus arising from the biological fluid into the partitioning system; removing at least a portion of the phase containing the virus from the partitioning system; and determining the virus by sequencing the nucleic acid within the phase removed from the partitioning system.

According to still another aspect, the method comprises partitioning a biological fluid in a partitioning system wherein the aqueous multi-phase partitioning system comprises an agent comprising a binding moiety specific for a virus within the biological fluid; and determining the virus within at least one phase of the partitioning system.

In accordance with one aspect, the method comprises partitioning a biological fluid in a multi-phase partitioning system; removing at least a portion of one phase of the partition system; releasing nucleic acid from a virus arising from the biological fluid into the portion of the one phase; and determining the nucleic acid in the phases of the partition system.

Another aspect is generally directed to a method, comprising partitioning a biological fluid in a multi-phase partitioning system; removing an aliquot from one phase of the partition system; releasing nucleic acid from a virus arising from the biological fluid into the portion of the aliquot; and determining the nucleic acid in the phases of the partition system.

Still another aspect is generally directed to a method comprising partitioning a biological fluid in a multi-phase partitioning system; removing aliquots from each of the phases of the partition system; releasing nucleic acid from a virus arising from the biological fluid into the aliquots; and determining the nucleic acid in the aliquots of the partition system.

Yet another aspect is generally directed to a method comprising partitioning a biological fluid in an aqueous multi-phase partitioning system, wherein the aqueous multi-phase partitioning system comprises an agent comprising a particle and a virus-binding moiety; and determining the particle within the phases of the partitioning system.

Still another aspect is generally directed to a method comprising partitioning a biological fluid in a partitioning system, and wherein the partitioning system comprises an agent comprising a particle and a virus-binding moiety; and determining the particle within the phases of the partitioning system.

Another aspect is generally directed to a method comprising exposing a biological fluid to an agent comprising a particle and a virus-binding moiety; partitioning the biological fluid in an aqueous multi-phase partitioning system; and determining the particle within the phases of the partitioning system.

Still another aspect is generally directed to a method comprising partitioning a biological fluid in an aqueous multi-phase partitioning system, wherein the partitioning system causes viruses arising from the biological fluid to partition such that at least 90% of viruses that are intact after partitioning are present in a first phase of the partitioning system; and determining the virus in the first phase of the partitioning system.

In another aspect, the present disclosure encompasses methods of making one or more of the embodiments described herein. In still another aspect, the present disclosure encompasses methods of using one or more of the embodiments described herein.

Other advantages and novel features of the present disclosure will become apparent from the following detailed description of various non-limiting embodiments of the disclosure when considered in conjunction with the accompanying figures.

BRIEF DESCRIPTION OF THE DRAWINGS

Non-limiting embodiments of the present disclosure will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of ordinary skill in the art to understand the disclosure. In the figures.

DETAILED DESCRIPTION

Figure 1:
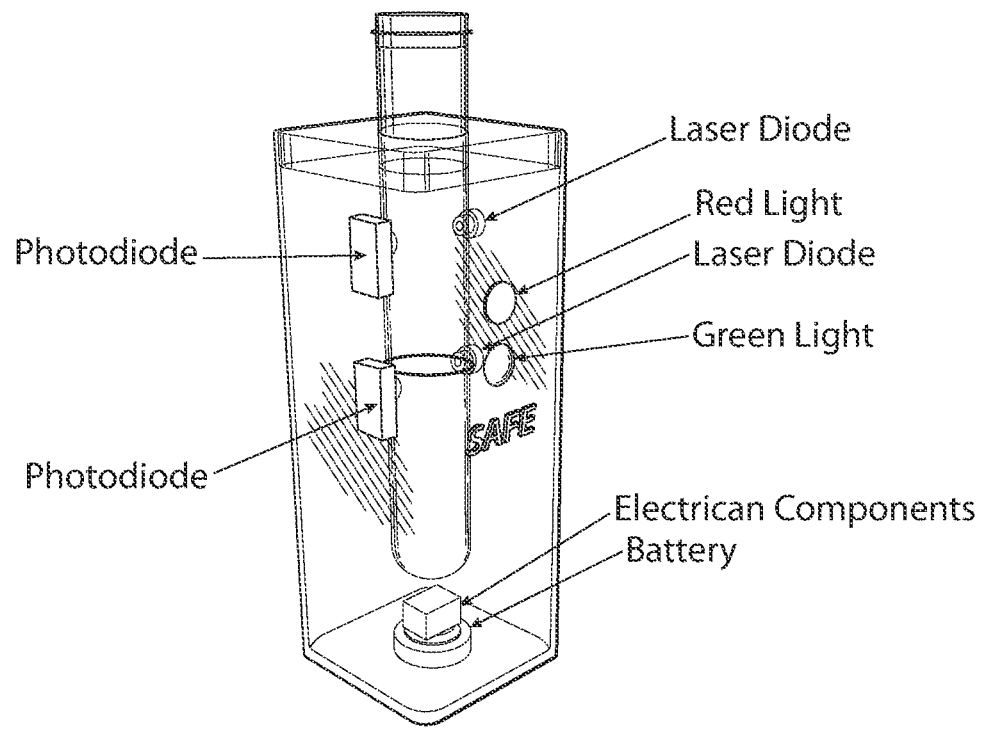
FIG. 1 illustrates an example device for determining a virus, in accordance with certain embodiments.

Certain aspects of the present disclosure generally relate to systems and methods for determining viruses such as coronaviruses. For instance, some aspects are directed to systems and methods for determining a virus using a partitioning system, such as an aqueous multi-phase partitioning system. Within the partitioning system, the virus may partition into a single phase, or more than one of the phases. In some cases, a binding moiety (e.g. a virus-binding moiety), such as an antibody selective for the virus, may also be added to facilitate partitioning of the virus. The binding moiety, in some cases, may also be attached to particles, such as gold or other nanoparticles, which may result in the formation of a complex of particles around a virus. One or more of the phases may be assayed to determine the virus, and/or RNA (or other nucleic acids) arising from the virus. For example, an agent comprising a virus-binding moiety, and optionally, a signaling moiety may be used within the partitioning system, where the distribution of the virus-binding moiety and/or the signaling moiety can be determined and used to determine the virus, qualitatively and/or quantitatively. For instance, if the signaling moiety is a dye, or is fluorescent, then the amount or concentration of signaling moiety in the phases of the partitioning system can be determined, for example, using fluorescence, absorbance, plate readers, or by visual inspection. As another example, the partitioning of the virus and/or RNA from the virus may be used to determine the virus; for example, by comparing the partitioning behavior of the virus and RNA from the virus may be used to determine how intact the virus is in the sample, and/or how infectious the sample or a subject is. In some cases, the partitioning of the virus may be altered, e.g., using various targeting species. In addition, in some cases, more than one type of virus may be determined using such a system. For example, different viruses may partition differently in a partitioning system such as discussed herein. As another example, a binding moiety may be selective for a coronavirus but not an influenza virus, or vice versa, such that the binding moiety may substantially alter the partitioning behavior of one virus, or complexes including the virus, relative to the other. In such fashion, viruses may be readily distinguished from each other, e.g., in a single partitioning system.

The binding moiety, in some cases, may also be attached to particles, such as gold or other nanoparticles, which may result in the formation of a complex of particles around a virus. As another example, the complex itself may contain a signaling moiety, e.g., attached to the particle, or the particle itself may contain a signaling moiety. In some cases, the complex itself may be detectable, e.g., as a change in color, even, in some embodiments, without a signaling moiety. Thus, for instance, if the signaling moiety is a dye, or is fluorescent, then the amount or concentration of signaling moiety in the phases of the partitioning system can be determined, for example, using fluorescence, absorbance, plate readers, or by visual inspection (i.e., visually). In some embodiments, the particles themselves are fluorescent. In addition, in some cases, more than one type of virus may be determined using such a system. For example, a binding moiety may be selective for a coronavirus but not an influenza virus, or vice versa, such that the binding moiety may substantially alter the partitioning behavior of one virus, or complexes including the virus, relative to the other. In such fashion, viruses may be readily distinguished from each other.

One aspect of the present disclosure is generally directed to systems and methods for determining viruses. Examples include, but are not limited to, coronaviruses, influenza viruses, or other viruses such as those described herein. In one set of embodiments, a partitioning system, such as an aqueous multi-phase partitioning system, is used. A sample, e.g., of a biological fluid taken from a subject, may be analyzed to determine whether a species of virus is present (e.g., SARS, MERS, COVID-19, etc.), and/or a type of virus is present (e.g., a coronavirus). The biological fluid may also be collected from a subject. Biological fluids may, in some cases, be processed for further use. Specific viruses, in certain embodiments, can be determined in the biological fluid. Further non-limiting examples of viruses are described below. In addition, in some cases, different types of viruses may be distinguished from each other (e.g., a coronavirus versus an influenza virus).

The sample of biological fluid may comprise fluids such as whole blood, blood serum, blood plasma, saliva, nasal fluid, sputum, urine, CNS fluid, breast nipple aspirate fluid, cerebral spinal fluid, semen, or the like. The subject that the biological fluid is taken from may be human, or non-human, e.g., a non-human mammal. Non-human mammals include, but are not limited to, a dog, cat, horse, cow, pig, sheep, goat, chicken, primate, rat, and mouse. In some cases, the subject is one that is suspected of being infected with a virus. For example, the subject may have previously been exposed to someone having the virus, or may at least be suspected of potentially having the virus. In addition, in certain embodiments, the subject may not be suspected of potentially having a virus (e.g., the fluid may be collected during routine screening).

A variety of different viruses may be determined, in accordance with various embodiments. Non-limiting examples of viruses, including infectious viruses, include coronaviruses or influenza viruses. Other non-limiting examples include adenoviruses, coxsackieviruses, Epstein-Barr viruses, hepatitis viruses (A, B, and C), herpes simplex viruses (types 1 and 2), cytomegaloviruses, herpes viruses (type 8), HIV, measles viruses, mumps viruses, papilloma viruses, parainfluenza viruses, polioviruses, rabies viruses, respiratory syncytial viruses, rubella viruses, varicella-zoster viruses, etc.

In some embodiments, a coronavirus may be determined. Examples of coronaviruses include, but are not limited to, HCoV-229E, HCoV-OC43, SARS-CoV, HCoV-NL63, HKU1, MERS-CoV, or SARS-CoV-2. As discussed herein, in some cases, one or more proteins of the coronavirus may be used to determine the virus, e.g., by interaction with a binding moiety that is able to bind to the proteins, or a targeting species, such as are discussed herein. Examples of such proteins on viruses include, but are not limited to, peplomers, envelope proteins, membrane proteins, nucleocapsids, spike glycoproteins, hemagglutinin-esterase dimers (HE), or the like. In addition, in some cases, the nuclear material of the virus (for example, RNA) may be determined, e.g., by interaction with a binding moiety or a targeting species, etc.

In some embodiments, an influenza virus may be determined. Influenza viruses include genera such as Influenza virus A, Influenza virus B, Influenza virus C, Influenza virus D, Isavirus, Thogotovirus, and Quaranjavirus. Examples of influenza A viruses include, but are not limited to, H1N1, H1N2, H2N2, H3N1, H3N2, H3N8, H5N1, H5N2, H5N3, H5N8, H5N9, H7N1, H7N2, H7N3, H7N4, H7N7, H7N9, H9N2, H10N7, etc. Examples of Influenza B viruses include, but are not limited to, Victoria and Yamagata. In some cases, one or more proteins of the influenza virus may be used to determine the virus, e.g., by interaction with a binding moiety or a targeting species, such as are discussed herein. Non-limiting examples of such virial proteins include hemagglutinin, neuraminidase, membrane proteins, glycoproteins, nucleocapsids, etc. In addition, in some cases, the nuclear material of the virus (for example, RNA) may be determined, e.g., by interaction with a virus-binding moiety or a targeting species.

In one set of embodiments, the biological fluid is partitioned in a partitioning system, such as a two-phase partitioning system, or other multi-phase system, e.g., having 3 or more phases. Two, three, four, or more phases may be present in the multi-phase partitioning system. In some embodiments, the partitioning system is aqueous, e.g., where each of the fluids is aqueous. Such aqueous partition systems may include aqueous phases formed with water and different types of polymers, such as Dextran and PEG or Dextran and Ficoll, by the same types of polymers with different molecular weights, such as Dextran-70 and PEG-600 or Dextran-70 and PEG-8,000, by the same polymers but containing different in type and/or concentration salt additives, different buffers of different pH and concentration, etc. Further examples of partitioning systems are described in more detail herein. However, it should be understood that in other embodiments, other types of multi-phase systems, e.g., containing non-aqueous phases, may be used.

In certain embodiments, the partitioning system may comprise an agent comprising a binding moiety, e.g., that is able to bind to a virus. Such agents may attach to target viruses within the sample via virus-binding moieties and/or a targeting species, e.g., by attaching to one or more proteins within the virus, for example, proteins such as peplomers, envelope proteins, membrane proteins, nucleocapsids, spike glycoproteins, hemagglutinin-esterase dimers (HE) or the like. For example, in some embodiments, a virus-binding moiety may bond to a protein (e.g. a peplomer) of a virus (e.g. a coronavirus such as COVID-19). In some cases, for example, the binding moiety may contain an antibody that is able to attach to the proteins.

In some cases, the agent may also comprise a particle, such as a nanoparticle. In some embodiments, at least some of the particles may be partially or fully coated with a virus-binding moiety, such as RNA or an antibody, or other virus-binding moieties such as those described herein. The agent may also comprise other moieties, such as signaling moieties and/or other moieties such as those described herein.

The virus-binding moiety may be selected to bind to a virus or at least a portion thereof, e.g., a protein of the virus, viral RNA, etc. In some cases, the binding may be specific. For example, the binding affinity of the virus-binding moiety to a portion of the virus may be less than 1 mM, less than 100 nM, less than 10 nM, or less than 1 nM. In some cases, the virus-binding moiety may bind to at least a portion of the virus to a significantly higher degree than to other molecules. For instance, the binding affinity may be at least 10×, 100×, or 1000× greater than for any other molecules that are present, e.g., in a sample of biological fluid. In some cases, the binding may be essentially irreversible, although it need not be in other cases. Thus, for example, in the case of a receptor/ligand binding pair the ligand would specifically and/or preferentially select its receptor from a complex mixture of molecules, or vice versa. An enzyme would specifically bind to its substrate, a nucleic acid would specifically bind to its complement, an antibody would specifically bind to its antigen, etc.

In some embodiments, one or more agents bind to a virus. For example, in some embodiments at least 1, at least 2, at least 4, at least 5, at least 10, at least 50, at least 100, at least 200, or more agents bind to a virus. In some embodiments, up to 500, up to 200, up to 100, up to 50, up to 10, up to 5, up to 4, or up to 2 agents bind to a virus. Combinations of these ranges are possible. For example, in some embodiments at least 1 and up to 500 agents may bind to a virus.

The binding interactions may be, for example, hydrogen bonds, van der Waals forces, hydrophobic interactions, covalent coupling, or the like. In addition, in some embodiments, the virus-binding moiety may be selected so as to selectively bind to a first virus, relative to a second virus. For example, the virus-binding moiety may be able to selectively bind a coronavirus relative to an influenza virus, or vice versa. Virus-binding moieties may comprise, for example, antibodies (e.g., able to bind to a protein, for example, the proteins described herein for coronaviruses, influenza viruses, etc.), or nucleic acids (e.g., able to bind to nucleic acids, such as RNA or DNA, arising from a virus, e.g., such that the virus-binding moiety comprises a nucleic acid sequence substantially complementary to a portion of the virus's genome). For example, the antibody may be an IgA. Other non-limiting examples include IgG, IgM, IgD and IgE.

In some cases, the antibody is a protein or glycoprotein consisting of one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as myriad immunoglobulin variable region genes. Light chains may include kappa or lambda. Heavy chains may include gamma, mu, alpha, delta, or epsilon, which in turn include immunoglobulin classes such as IgG, IgM, IgA, IgD, or IgE. A typical immunoglobulin (antibody) structural unit may comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. Antibodies exist as intact immunoglobulins or as a number of well-characterized fragments, e.g., which can be produced by digestion with various peptidases. Thus, for example, pepsin can digest an antibody below (i.e., toward the Fc domain) the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab')2 dimer into an Fab' monomer. The Fab' monomer is essentially a Fab with part of the hinge region. While various antibody fragments are defined in terms of the digestion of an intact antibody, such fragments may also be synthesized de novo, for example, chemically by utilizing recombinant DNA methodology, by "phage display" methods, or the like. Examples of antibodies include single chain antibodies, e.g., single chain Fv (scFv) antibodies in which a variable heavy and a variable light chain are joined together (directly or through a peptide linker) to form a continuous polypeptide.

The signaling moiety, if present, may be any entity that can be determined, e.g., to determine the partitioning of the virus. For instance, upon binding of the virus-binding moiety to the virus, the signaling moiety may be determined, qualitatively and/or quantitatively, in the partitioning system, e.g., to allow the partitioning of the virus within the partitioning system to be determined. The signaling moiety, may be for example, colored, fluorescent, radioactive, etc. Non-limiting examples of signaling moieties include a dye, a fluorescent dye, a chemiluminescent entity, a radioactive label, an isotope such as a non-radioactive isotope or an isotope detectable by mass spectrometry, a ligand which can serve as a specific binding partner to a labeled antibody, an enzyme, an antibody which can serve as a specific binding partner for a labeled ligand, an antigen, a group having a specific reactivity, and/or an electrochemically detectable moieties. Non-limiting examples of dyes or fluorescent signaling moieties include fluorescein, calcein, rhodamine, Green Fluorescent Protein (GFP), etc. Those of ordinary skill in the art will be aware of other fluorescent entities that are readily commercially available.

The signaling moiety may be determined, in some cases, using a suitable detector, although in certain embodiments, the signaling moiety can be determined unaided, e.g., to the naked eye. Examples of suitable detectors include, but are not limited to, microscopes (e.g., fluorescence microscopes), plate readers, ELISA readers, Geiger counters, mass spectrometers, cameras (e.g., within smart phones or cell phones) or the like. Other examples of detectors include any of those described herein. In some cases, the signaling moiety may be colorimetrically determined (e.g. within the phases of the partitioning system). The signaling moiety can also be determined, in some embodiments, by determining a color change in at least one phase of the partitioning system. The signaling moiety may also be determined fluorescently, in some embodiments. In some cases, the signaling moiety may be determined using ELISA (e.g. within the phases of the partitioning system).

Binding of the agent, in some cases, may also alter the partitioning of the virus. For example, the agent may bind to the virus via the virus-binding moiety, thereby altering the effective structure of the virus, and at least in some cases, its partitioning. Accordingly, upon binding of the virus-binding moiety to a virus, the partitioning of the agent may appear to change, which can be determined, for example, by determining a change in the partitioning of the signaling moiety within the partitioning system. In some cases, the change in partitioning may be relatively substantial. For example, the change in partitioning may be such that in the presence (or absence) of the virus, the agent partitions such that at least 50% (by number), at least 55%, at least 60%, at least 65%, at least 70%, at least 75%, at least 80%, at least 85%, at least 90%, at least 95%, etc. of the agent is in a single phase of the partitioning system.

In some cases, this change in partitioning may be intentional. For example, in certain embodiments, the agent may comprise other components whose partitioning behavior may change, e.g., upon binding to a virus.

A variety of methods may be used to determine partitioning of the virus in one or more phases within a partitioning system. For instance, in one set of embodiments, a signaling moiety may be determined, e.g., as discussed herein. In another set of embodiments, however, other methods may be used, for example, if no signaling moiety is present. For example, in one set of embodiments, aggregation of virus may be determined as a change in color or clarity, etc., within one or more phases of the partitioning system. A variety of systems may be used to determine the particles and/or the phases colorimetrically, for example, by determining the particles themselves, and/or signaling moieties or the like, e.g., as discussed herein. For example, the particle may be determined based on the partitioning of a signaling moiety within the phases of the partitioning system. As another example, the particle may be determined by exposing the agent to a second agent comprising a signaling moiety and a binding moiety able to bind to the agent and/or the virus. In some embodiments, the particle may be determined within phases of the partitioning system by determining a change in light scattering.

In some cases, partitioning of the virus in one or more phases within a partitioning system may be determined using a suitable detector, although in some embodiments, partitioning may be determined without a detector, e.g., by using the naked eye. Examples of suitable detectors include, but are not limited to, microscopes (e.g., fluorescence microscopes), plate readers, ELISA readers, Geiger counters, mass spectrometers, cameras (e.g., within smart phones or cell phones) or the like. Other examples include any of the detectors described herein. In some cases, the virus may be colorimetrically determined.

In some cases, the detector may be a handheld device or a portable device, such as the example shown in FIG. 1. As one example, a smart phone or a cell phone may be used to determine the signaling moiety. As another example, a cellphone or a smartphone can be used as a colorimetric detector. For example, an app or a program on a smartphone may be used to determine one, two, or more phases of the partitioning system, and if the colors or other characteristics of the phases meet certain criteria (e.g., different colors, different ratios of light scattering, different intensities, etc.), e.g., due to the formation of complexes in a phase, then the virus may be determined.

As yet another example, the agent may be determined by exposing the agent to a second agent comprising a signaling moiety and a binding moiety, where the binding moiety is able to bind the complex. For instance, the binding moiety may be able to bind to the virus, e.g., a virus-binding moiety, and/or bind to the particles. For example, in one set of embodiments, the second agent may comprise a signaling moiety and a virus-binding entity. The virus-binding entity of the second agent may be the same or different than the virus-binding entity of the agent, e.g., as described above.

As another example, the second agent may comprise a signaling moiety and a complex-binding entity, e.g., able to bind to the complex of the virus and the agent, as described above. For instance, the complex-binding entity may be selected to bind to the complex, e.g., specifically. For example, the binding affinity of the complex-binding moiety to a portion of the complex, such as to the particle, to the virus, etc. may be less than 1 mM, less than 100 nM, less than 10 nM, or less than 1 nM. In some cases, the complex-binding moiety may bind to a portion of the complex to a significantly higher degree than to other molecules, e.g., within the sample. For instance, the binding affinity may be at least 10×, 100×, or 1000× greater than for any other molecules or entities that are present. In some cases, the binding may be essentially irreversible, although it need not be in other cases. Thus, for example, in the case of a receptor/ligand binding pair the ligand would specifically and/or preferentially select its receptor from a complexed mixture of molecules, or vice versa. An enzyme would specifically bind to its substrate, a nucleic acid would specifically bind to its complement, an antibody would specifically bind to its antigen, etc. The binding interactions may be, for example, hydrogen bonds, van der Waals forces, hydrophobic interactions, covalent coupling, or the like. In addition, in some embodiments, the complex-binding entity may be selected so as to selectively bind to complexes of a first virus, relative to a second virus. For example, the complex-binding moiety may be able to selectively bind a coronavirus complex relative to an influenza virus complex, or vice versa. Exemplary complex-binding moieties may include or comprise, but are not limited to, antibodies (e.g., able to bind to a protein, for example, the proteins described herein for coronaviruses, influenza viruses, etc.), or nucleic acids (e.g., able to bind to nucleic acids, such as RNA or DNA, arising from a virus, e.g., such that the virus-binding moiety comprises a nucleic acid sequence substantially complementary to a portion of the virus's genome). For example, the antibody may be an IgA. Other examples include IgG, IgM, IgD and IgE.

In certain embodiments, a targeting species able to bind to a virus that may be present, e.g., in the partitioning system. The targeting species may be separate from the agent (e.g. the first agent and/or the second agent) in some embodiments. In certain embodiments, a virus may be exposed a targeting species within a partitioning system (e.g. a first aqueous multi-phase partitioning system, a second aqueous multi-phase partitioning system). The targeting species may be allowed to bind to or otherwise interact with a virus, e.g., specifically. In some embodiments, binding of the targeting species to the virus alters partitioning of the virus in the partitioning system. This may be useful, for example, to help distinguish a first virus from a second virus, e.g., a coronavirus and an influenza virus. For instance, the targeting species may have a virus-binding moiety (for example, as discussed herein), that is able to recognize only a first virus but not a second virus. Binding of the targeting species to the first virus thus may alter the partitioning behavior of the first virus, but not the second virus, as the second virus is not recognizable (or is recognizable, but to a much lesser extent), by the targeting species. Accordingly, the viruses may exhibit substantially different partitioning behavior in the presence of the targeting species, which can be determined, for example, using agents or techniques such as those described herein. However, it should be understood that a targeting species is not required, and in other embodiments, the viruses may exhibit distinguishable partitioning behavior, i.e., without any targeting species, and/or the agent itself may alter the partitioning behavior, e.g., upon binding to the virus.

Exemplary targeting species may include or comprise, but are not limited to, antibodies (e.g., able to bind to a protein, for example, the proteins described herein for coronaviruses, influenza viruses, etc.), or nucleic acids (e.g., able to bind to nucleic acids, such as RNA or DNA, arising from a virus, e.g., such that the virus-binding moiety comprises a nucleic acid sequence substantially complementary to a portion of the virus's genome). For example, the antibody may be an IgA. Other examples include IgG, IgM, IgD and IgE.

In addition, in some cases, the targeting species may cause aggregation of the viruses. For example, the targeting species may be able to bind to two or more viruses. As an example, the targeting species may include two or more antibodies, nucleic acids, or other species able to bind to a virus.

Figure 2:
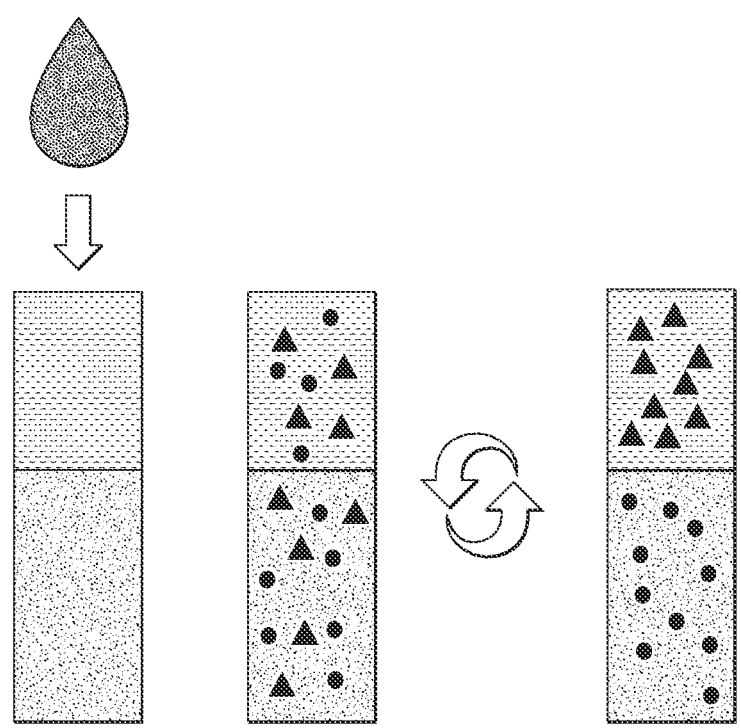
FIG. 2 illustrates an example of a partitioning system for different viruses in another embodiment.

One non-limiting example of such a system can be seen schematically in FIG. 2. In this figure, a partitioning system is shown on the left, and a sample is added. The sample may be, e.g., blood, sputum, saliva, nasal fluid, or other biological fluids such as those described herein. In this example, a two-phase partitioning system is shown as a schematic, although in other embodiments, there may be two or more than two phases.

In this example, the sample may contain two types of viruses, shown schematically as triangles and circles. The triangles represent the virus of interest, while the circles represent other types of viruses (and there may be more than one type of such viruses present in other embodiments). For example, in certain cases, there may be 2, 3, 4, or more contaminating viruses, and/or other entities that are present. Initially, the sample may be randomly distributed between the two phases, although with some mixing, the system may progress towards an equilibrium. This may be facilitated, for example, by agitating the sample in some fashion, e.g., stirring, vortexing, centrifugation, etc. In addition, in some cases, the agitation may be performed by hand. Such agitation may facilitate the distribution of the viruses in the different phases of the partitioning system. This is shown schematically in FIG. 2 as perfect separation (all triangles in the upper phase and all circles in the lower phase), although in reality, the separation need not always be 100% efficient. Lesser amounts of separation are also possible, e.g., as discussed herein. After partitioning of the viruses in the phases, one or more of the phases may be assayed to determine the viruses within those phases, e.g., qualitatively and/or quantitatively (e.g., as a concentration). In some cases, a signaling moiety may be used to facilitate assaying of the viruses. For example, the viruses may be determined colorimetrically, using fluorescence, based on radioactivity, or the like. In certain instances, the assay may be performed using the naked eye (e.g., by determining the viruses colorimetrically), although in some cases, other assay techniques, such as those described herein, may be used to determine the viruses.

Figure 3:
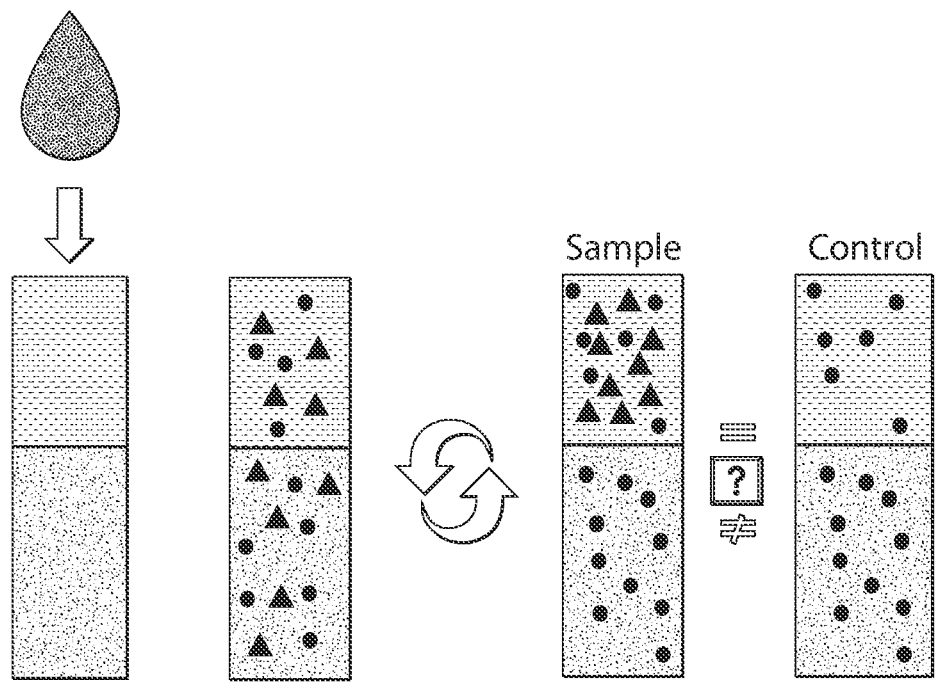
FIG. 3 illustrates another example of a partitioning system which partitions two different viruses different, in yet another embodiment.

Another non-limiting example of a system is shown schematically in FIG. 3. In this figure, the non-desired viruses are shown being unable to partition between the two phases (as is shown in the "control" experiment), although the viruses of interest can partition (as is shown in the "sample" experiment). A variety of techniques may be used to assay the sample. For example, the top phase of the experiments may be removed and used to determine whether the viruses of interest are present or not. As another example, the distribution of viruses in an experiment may be determined, with higher concentrations of viruses within the top phase being related to the presence of the virus of interest. It should be noted that the viruses need not necessarily be distinguished from each other (although they can be), as it is only the total concentration of viruses that is determined in this variation.

As a non-limiting example, the non-desired viruses may be a known virus (e.g., influenza virus), and the partitioning system may be selected such that known virus distributes in both phases (the concentrations within the two phases may be the same or different). If a virus of interest is present, and is predominantly partitioned in the top phase, then the overall virus partition coefficient, e.g., obtained by a non-specific viral assay of both phases, will be different than what would be expected if only the influenza virus were present (compare the "sample" and the "control" experiments, respectively). Accordingly, for example, the "sample" may be flagged for further analysis or assays, e.g., using techniques such as those described herein. This may be valuable, especially if the virus of interest is relatively new, or one that has not yet been well-characterized, etc. In certain embodiments, the virus need not be explicitly determined; instead, the "sample" may merely be identified as being one where further testing is required, e.g., due to the change in partitioning of viruses within the partitioning system, for example, when compared to the partitioning of known viruses.

It should be understood that although the partitioning was demonstrated as an idealized system, in reality, the partitioning may not be perfect. For example, the sizes of the phases and/or concentrations of viruses within the phases can vary, e.g., where perfect separation or partitioning is not achieved.

Figure 4:
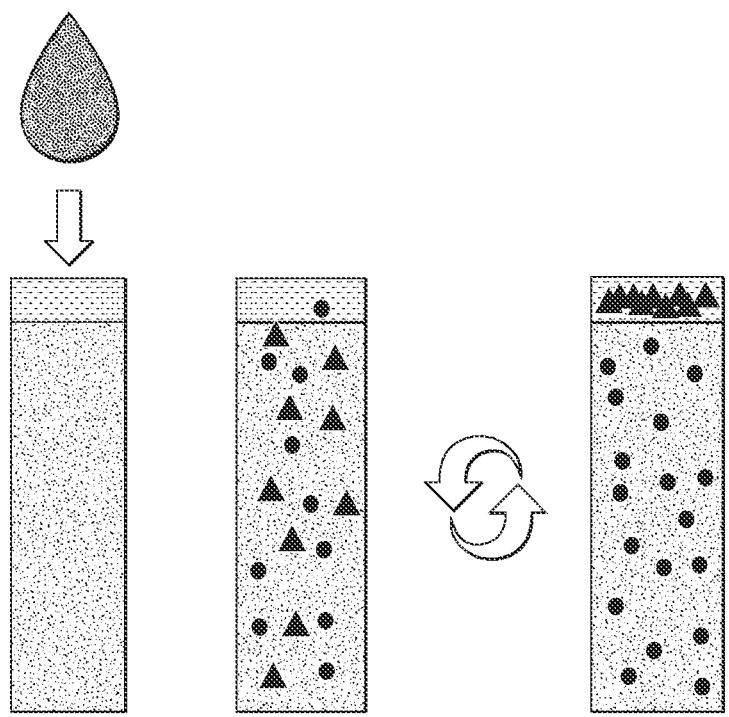
FIG. 4 illustrates another example of a partitioning system in which the phases are not all substantially evenly distributed, in still another embodiment.

As another example, a schematic diagram is shown in FIG. 4 as a non-limiting example. In this case, the top phase is relatively small compared to the bottom phase. This may be useful, for example, where the virus is to be analyzed and/or determined, and/or to facilitate enrichment of the viruses, sample purification, or the like. For example, after using this system, the viruses of interest may be relatively concentrated in a first phase, while other viruses may be more evenly distributed or not concentration within the first phase along the virus of interest.

Another aspect of the present disclosure relates to methods and devices for detecting the presence or risk of a disease or condition, e.g., an infection, as related to differential solubility behavior of a virus in the portions or phases of two substantially immiscible liquids. Partitioning systems, including aqueous partitioning systems may be generally employed in some embodiments, wherein the partitioning behavior of a virus is determined. In some cases, different viruses may be distinguished, e.g., as discussed herein.

In some embodiments, a virus can be partitioned in the phases of two (or more) substantially immiscible liquids of a partitioning system, such as an aqueous partitioning system. For example, the two phases of a partitioning system may have different molecular structures in some cases. In equilibrium, differences between the molecular interactions of the virus and the various phases may be determined using the value of a partitioning coefficient between the phases. The value of the partition coefficient for a virus may change, for instance, if the three-dimensional structure of the virus changes.

The chemical ingredients used to prepare a partitioning system that naturally partitions into two or more phases may be selected (e.g., as discussed below) so as to provide this differentiation of behavior as a function of the virus. Once one or more viruses have been partitioned, each phase can be assayed, for example, through immuno-specific assays like ELISA. The viruses may be determined in each phase. A partitioning coefficient, K, may also be determined in some cases from the ratio of concentration of viruses in each phase.

K values for each virus may, in some embodiments, be chosen to be significantly different. For example, K values determined for a subject may be compared to similar ratio values previously determined and recorded for subjects with known health statuses, e.g., infections In one set of embodiments, a virus may be partitioned into the phases (e.g. aqueous phases) of two or more substantially immiscible liquids. Different viruses may differentially partition in each phase. The phases may have different molecular structures. In equilibrium, the differences between the molecular interactions of a virus and the various phases may be manifested through differential solubility of the virus between the phases. In addition, in some cases, the partitioning behavior of a virus may be altered using a targeting species, e.g., as discussed herein.

In some embodiments, only one of the phases (e.g. aqueous phases) is analyzed for concentration, for a virus; no ratio calculation may be used, as the second phase is used for partitioning but not for the assay (however, in other embodiments, more than one of the phases may be analyzed for viral concentrations, as discussed herein).

Preparation of partitioning systems such as those described herein may, in some embodiments, include large-scale robotic screening of chemical ingredients such as soluble polymers, salts, and other additives to cause spontaneous phase separation, e.g., into two or more phases. This screening may be targeted to discover and/or optimize such formulae to distinguish those which could confer differential partitioning of viruses.

In some aspects, a feature for allowing differential solubility for the viruses is a liquid partitioning system. Thus, certain embodiments make use of a liquid partitioning system for use in the detection of a disease or condition in a subject, including: two or more liquid phases, the liquid phases being substantially immiscible. In some cases, some or all of the liquid phases may have an aqueous component. In some embodiments, a plurality of species associated with the disease or condition can be solubilized. In some cases, the concentrations of a virus in a phase may be related to the presence or absence of the disease or condition in the subject.

Typical, but non-limiting, components of the aqueous phases include at least one of polyethylene glycol, dextran, polyvinyleperrolidone, Ficoll, and copolymer of ethylene glycol and propylene glycol. The liquid partitioning system may include, in some embodiments, substantially immiscible phases, where some or all of the phases may have an aqueous component. The virus may interact differently with the chemicals (and water) of each layer, and thus dissolve or partition differentially. Liquid partitioning systems, including aqueous liquid partitioning systems and various compositions for forming such systems, are discussed in greater detail herein. However it should be noted that the disclosure is not limited to only liquid-liquid partitioning, e.g., as described above, but also encompasses, in other embodiments, chromatography (e.g., liquid-liquid partition chromatography), heterogeneous two-phase systems, or multi-phase heterogeneous systems), and other suitable techniques for generating a partition coefficient or at least an apparent partition coefficient.

In addition, in accordance with certain aspects of the present disclosure, the state of a molecule, such as a virus, can be affected by many different factors including, but not limited to, changes in the structure of the virus, interactions with one or more other biomolecules or ligands, and the like. Evaluation of different states can be used as one method of determining the potential effectiveness of different potential species on the virus, etc.

Figure 5:
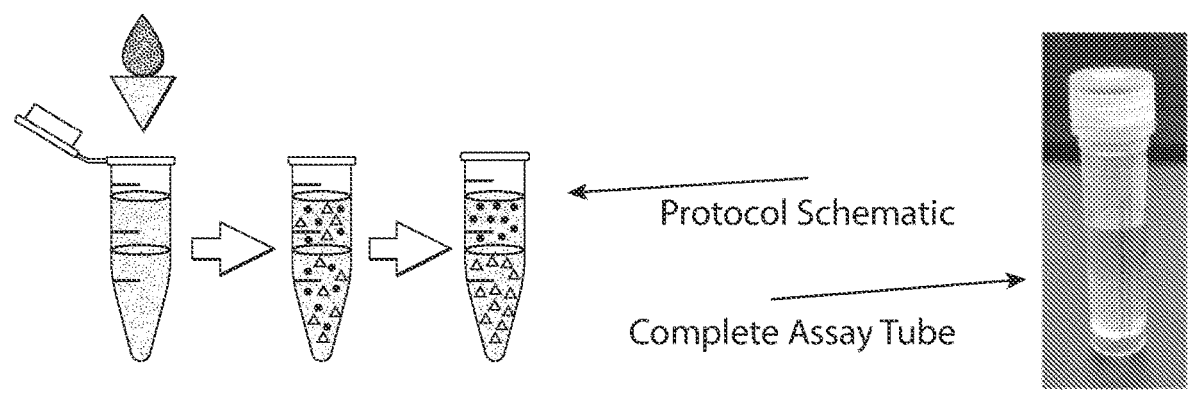
FIG. 5 illustrates an example of an assay in accordance with one embodiment.

As previously discussed, in certain embodiments, a virus may partition in one or more phases of the partitioning system, e.g., depending on the agent, a binding moiety, a targeting species, or the like. For example, a virus may be partitioned such that a significant concentration appears in one phase of the partitioning system, e.g., at least 50%, at least 55%, at least 60%, at least 65%, at least 70%, at least 75%, at least 80%, at least 85%, at least 90%, at least 95%, at least 99%, etc., of the virus (e.g., by number) is present in a single phase of the partitioning system. The virus may be determined, e.g., using a colorimetric assay, a signaling moiety, or other techniques such as those discussed herein. In addition, in some cases, a first virus may exhibit such partitioning, while a second virus may exhibit different partitioning. For instance, the second virus may partition more evenly within different phases of the partitioning system, or the second virus may partition in a different phase than the first virus (e.g., as shown in FIG. 5), or the like. Accordingly, the first and second viruses may be distinguished, for instance, based on their partitioning behavior. For instance, a first virus may be found predominantly in the first phase, while the second virus may be found relatively more evenly distributed in the first and second phases.

In addition, in some cases, partitioning of the virus in the partitioning system may be surprisingly rapid. For example, in some cases, substantial partitioning may occur in less than 1 hour, less than 30 minutes, less than 15 minutes, less than 10 minutes, less than 5 minutes, less than 3 minutes, less than 2 minutes, or less than 1 minute. In some cases, within these times, sufficient partitioning may have occurred to allow for determination of the virus as discussed herein, e.g., in one or more phases of the partitioning system. For example, within these times, partitioning of the virus can be determined colorimetrically or with the naked eye, etc.

In some aspects, a phase of the partitioning system may be removed, and optionally transferred to a second partitioning system. The second partitioning system may include any of the systems described herein, and may be the same or different than the first partitioning system.

In one set of embodiments, one or more of the phases of a partitioning system may contain a virus, which can be determined, e.g., as discussed herein. In some cases, the virus may be denatured, e.g., to release nucleic acid from the virus into the partitioning system, e.g., for determination. For example, the nucleic acid may comprise DNA and/or RNA. For example, to release nucleic acid, the virus can be exposed to a denaturing agent, alkaline hydrolysis, Iso-Quick, lysis buffer in conjunction with proteinase K, phenol-chloroform extraction followed by ethanol precipitation, solvent or detergent inactivation (e.g., using Triton X-100), pasteurization (heating, e.g., to temperatures of at least 60° C., at least 70° C., at least 80° C., at least 90° C., etc.), acidic (low pH) inactivation, or other techniques known to those of ordinary skill in the art.

In yet another set of embodiments, various systems and methods such as those discussed herein can be used to purify a sample of biological fluid. In some cases, the sample of biological fluid may be from a subject, such as a subject suspected of having or being exposed to a specific viral disease.

In some cases, systems and methods such as those discussed herein may be used prior to other tests such as those described herein, for example, identification tests such as polymerase chain reaction (PCR), sequencing techniques including those described herein, or the like. This may be important, for example, in applications when a sample may potentially be contaminated, e.g., with closely related RNA or DNA material from similar viral families, or to distinguish between different types of viruses (e.g., coronavirus versus influenza virus), etc. In certain embodiments, as a non-limiting example, a virus or viral component of interest from a sample may be partitioned into, or at least partially enriched in, one phase of a partitioning system (e.g., an aqueous multi-phase partitioning system), while other matter may be partitioned into a different phase. The phase containing or being enriched in the virus or other viral component of interest (e.g., RNA) may then in some cases be used for identification or sequencing tests, etc., such as those described herein.

In some embodiments, viruses or other viral material may be concentrated in one phase of a partitioning system (e.g., an aqueous multi-phase partitioning system) by selecting properties of the partitioning system such that the volume ratio between that phase and the other phase(s) will be large. For example, a partitioning system may be selected to have a volume ratio of the two phases to be 1:1 or more, 1:2 or more, 1:3 or more, 1:5 or more, 1:10 or more, 1:20 or more, 1:50 or more, or even larger, where the smaller volume is the phase containing or being enriched in the virus or other viral component of interest. In some cases, substantially all of the virus may be present in one phase of the partitioning system. According to certain embodiments, the presence of substantially all the virus in one or more phase of the partitioning system may mean that greater than or equal to 80%, greater than or equal to 85%, greater or equal to 90%, greater than or equal to 95%, or greater than or equal to 97.5% of the viruses may be found within that one or more phase.

In certain cases, a virus may be determined by determining a nucleic acid originating from the virus. For example, a virus may be denatured, e.g., as discussed herein, to release a nucleic acid from the interior of the virus. Those of ordinary skill in the art will be able to determine the nucleic acid, for example, using antibodies that bind to nucleic acid, or the like. The nucleic acid may be determined colormetrically, for example. In some cases, signaling moieties may be attached to nucleic acid-binding entities to facilitate detection, e.g., within the partitioning system. For example, signaling moieties that bind to nucleic acids can be used to determine partitioning. Non-limiting examples of signaling moieties include ethidium bromine or ethidium monoazide bromide, cyanine dyes (e.g. Cy3, Cy5, etc.), propidium iodide, crystal violet, dUTP-conjugated probes, DAPI (4',6-diamidino-2-phenylindole), 7-AAD (7-aminoactinomycin D), Hoechst 33258, Hoechst 33342, Hoechst 34580, YOYO-1, DiYO-1, TOTO-1, DiTO-1, etc. Other examples of signaling moieties include those discussed herein.

In addition, in some cases, the nucleic acid may be sequenced. Examples of sequencing techniques known to those of ordinary skill in the art include, but are not limited to, Sanger methods or other suitable techniques, chain-termination sequencing, sequencing-by-hybridization, Maxam-Gilbert sequencing, dye-terminator sequencing, chain-termination methods, Massively Parallel Signature Sequencing (Lynx Therapeutics), polony sequencing, pyrosequencing, sequencing by ligation, ion semiconductor sequencing, DNA nanoball sequencing, single-molecule real-time sequencing, nanopore sequencing, microfluidic Sanger sequencing, digital RNA sequencing ("digital RNA-seq"), etc.

In some cases, such signaling moieties such as those described herein may be determined unaided, e.g., to the naked eye, although detectors such as those described may be used in certain embodiments. Non-limiting examples of suitable detectors include microscopes (e.g., fluorescence microscopes), plate readers, ELISA readers, etc. In some cases, the signaling moiety may be colorimetrically determined.

As another non-limiting example, a signaling moiety may comprise a particle. The particles may be nanoparticles, such as gold nanoparticles, that, in some embodiments are, coated with a virus-binding moiety, such as RNA. These can be mixed, e.g., in situ, with a partitioning system containing viruses or other viral material. Upon hybridization with target viral nucleic acids in a partitioning system, a color change may be used to indicate presence of a specific target viral nucleic acid. This may be, in some embodiments, at high specificity due to the hybridization specificity of the nanoparticles. In addition, in some cases, e.g., if one phase of the partitioning system is enriched in the target viral nucleic acid, the color change may be relatively concentrated in one phase of the portioning system. Thus, a color change specific to one phase in the partitioning system may be used to determine the target viral nucleic acids. In addition, in some cases, the degree of color change may be used to determine concentrations. In some cases, this dual-specificity test may reach the diagnostic specificity of PCR with the speed and simplicity of other colorimetric screening assays.

In some cases, a targeting species may be used. Non-limiting examples include targeting species such as those described herein. For example, the targeting species may cause aggregation of the viruses.

Particles may be of any suitable size. For example, particles may have a diameter of greater than or equal to 10 nm, greater than or equal to 50 nm, greater than or equal to 100 nm, greater than or equal to 500 nm, greater than or equal to 1 micrometer, or greater. In some embodiments, particles have a diameter of less than or equal to 5 micrometers, less than or equal to 1 micrometer, less than or equal to 500 nm, less than or equal to 100 nm, or less. Combinations of these ranges are possible. For instance, in some embodiments, particles may have a diameter that is greater than or equal to 10 nm and less than or equal to 5 micrometer.

Particles as described herein may comprise any suitable material. In some embodiments, particles may comprise metals. For example, particles may comprise gold, silver, titanium, or any other suitable material. Particles may also comprise polymers or ceramic materials appropriate for a given embodiment.

In one aspect, partitioning systems such as those discussed herein may be used to determine intact viruses, e.g., virion particles, that may be present in a sample. For instance, a partitioning system may be used to separate or concentrate viruses, e.g., within one of the phases. Systems include those described herein. In addition, in some cases, the amount or concentration of intact viruses in a sample may be determined, and optionally compared to RNA (or other nucleic acids) that are not present within intact viruses, e.g., free-floating within the sample. The amount or concentration of RNA (or other nucleic acids) within one or more phases may be determined using any suitable technique, such as via polymerase chain reaction (PCR), sequencing or other techniques including those described herein, etc.

Similarly, intact viruses (e.g., virion particles) within one or more phases of the partitioning system may be determined using any suitable technique, including those discussed herein. The techniques for determining intact viruses and free nucleic acids may be the same or different. For instance, nucleic acids (e.g., RNA and/or DNA) may be extracted from the viruses, e.g., after separation, and determined in some fashion, e.g., via polymerase chain reaction (PCR), sequencing techniques including those described herein, or the like.

As a non-limiting example, if the partitioning behavior of free nucleic acid (e.g., arising from the virus) in the partitioning system is known, then the partitioning behavior of the nucleic acid may be compared to the partitioning behavior of a control, such as the free nucleic acid. This comparison may be used to determine the nucleic acid contained within intact viruses within the sample. For instance, a sample may be partitioned within a partitioning system, and one or more phases of the partitioning system may be removed or separated, e.g., for analysis using techniques such as those described herein. The one or more phases may be removed prior to determining the virus, or may be removed after determining the virus. After removal or separation, intact viruses within a phase may be processed to extract their nucleic acids, e.g., into solution. The amount and/or concentration of nucleic acids in the phases of the partitioning system may then be determined, and in some cases, used to determine a partition coefficient. The partition coefficient can, in some cases, be compared to the expected values for only free nucleic acid in the partition system, and any differences may be used to determine the existence of intact viruses within the sample, in addition to free RNA, and e.g., an amount or concentration.

Techniques such as these, in certain embodiments, can allow for the determination of intact viruses in a sample. In some cases, this may be related to the severity of the disease, the stage of illness, the infectiousness of the subject, or the like. In contrast, in many other techniques, it is not possible to distinguish intact viruses from viruses that have released their nucleic acids, e.g., into the sample.

As a non-limiting example, in one embodiment, a sample may be partitioned within the phases of a suitable partitioning system, e.g., such as has been described herein. After equilibration, aliquots of one or more of the phases may be taken, and optionally one or more of them may be processed in some fashion, e.g., to cause any intact viruses that might be present to release their nucleic acids into solution. The nucleic acids in the phases may be determined, e.g., using PCR or other sequencing techniques such as those described herein. In some cases, the amount of a particular nucleic acid sequence (e.g., the RNA of the virus) may be determined in the phases, and used to calculate a partition coefficient. This coefficient may in some embodiments be compared to the expected partition coefficient for the free form of the nucleic acid. If these are substantively equal, then that would suggest that no intact viruses were present in solution. However, if these values are different, then that would suggest at least some intact viruses were present in the sample, as the intact viruses may partition differently than free nucleic acid within the partitioning system. This may be particularly useful if the partitioning system is chosen to be selectively preferential to the intact virus, e.g., such that at least 50%, at least 55%, at least 60%, at least 65%, at least 70%, at least 75%, at least 80%, at least 85%, at least 90%, at least 95%, at least 99%, etc. of the virus is present in one phase, for instance, as is discussed herein. In some cases, the differences can be quantified and used to determine the relative amount or concentration of intact virus present within the sample.

One non-limiting example is now described with reference to FIGS. 6A-6B. In these figures, a sample, e.g., arising from a subject may be obtained, e.g., saliva (panel 1A) or a swab (panel 1B). The sample may be added to a partitioning system, e.g., directly or indirectly, and allowed to partition therein, e.g., as is shown in panels 2A/2B and 3. In some cases, this may be facilitated by shaking the container, or by using other techniques such as those described herein. In some cases, intact viruses (e.g., SARS-CoV-2 virions, or other viruses such as those described herein) may preferentially be present in the bottom phase, e.g., in concentrations or amounts such as those discussed herein. One or more of the phases may then be determined, e.g., to determine the presence of nucleic acids arising from the virus, e.g., using PCR techniques such as RT/PCR (reverse transcription polymerase chain reaction), or other techniques including those described herein. In addition, in some cases, intact viruses that may be present may be processed in some fashion, e.g., to cause release of nucleic acids into each phase.

In certain embodiments, a partitioning system causes the sample to partition such that intact viruses (e.g. SARS-CoV-2 virions, or other viruses such as those described herein) only appear in a first (e.g. bottom) phase. In certain embodiments, a partitioning system causes the sample to partition such that nucleic acids or antigens arising from non-intact viruses only appear in a second (e.g. top) phase. One or more phases may then be determined, e.g., to determine the presence of nucleic acids or antigens (e.g. spike protein antigens) arising from the virus, e.g. using PCR techniques such as RT/PCR to determine the presence of nucleic acids, or using antigen tests to determine the presence of antigens. According to certain embodiments, determining a first phase may determine whether a sample is infectious. For example, determining a first (e.g. bottom) phase to determine the presence of intact viruses may be used to determine whether a patient is infectious. In some cases, determining a second phase may determine whether a sample is positive for the virus. For example, determining a second (e.g. top) phase to determine the presence of nucleic acids or antigens (e.g. spike protein antigens) arising from the virus may be used to determine whether a sample is positive for the virus. In certain embodiments, determining an intact virus within a first phase and a nucleic acid or antigen arising from the virus in a second phase may advantageously indicate positivity and infectiousness without requiring a partition coefficient, eliminating the need for determining the intact virus or the nucleic acid or antigen arising from the virus in more than one phase.

A non-limiting example is now described with reference to FIGS. 6C-6D. In these figures, a sample, e.g., arising from a subject may be obtained, e.g., a swab (panel 1). The sample may be added to a partitioning system, e.g., directly or indirectly, and allowed to partition therein, e.g., as is shown in panel 2. One or more phases may then be determined, e.g., to determine an intact virus (panel 3 of FIGS. 6C-6D) in a first phase, and/or to determine a nucleic acid arising from the virus (FIG. 6C, panel 3) or an antigen arising from the virus (FIG. 6D, panel 3).

As mentioned above, certain aspects of the present disclosure are generally directed to the investigation of the state of a virus, although the disclosure is not limited to only viruses. Other embodiments can be applied to essentially any molecular species and/or interaction, whether biological, biochemical, chemical, or other species, and those of ordinary skill in the art will understand how the disclosure can be used in the context of other molecules. Accordingly, it is to be understood that whenever "virus" is used in the description herein, any other biological or non-biological molecule also can be used or studied in other embodiments.

Some embodiments are directed to techniques for determining information about compositions suspected of containing viruses, and/or molecules able to interact with viruses. The composition may originate from a biological fluid (or other sample), such as a human clinical sample or other biological fluid, tissue, cells, a subject, etc., or the mixture may be a synthetic mixture. The mixture can come from a biological system (e.g., a subject) which includes, but is not limited to, a human or non-human mammal. Non-human mammals include, but are not limited to, a dog, cat, horse, cow, pig, sheep, goat, chicken, primate, rat, and mouse.

Some embodiments are related to developing and determining characteristics (quantitative and/or qualitative) of a mixture that are obtained, for example, via processing using multi-phase partitioning, which can reflect certain structural and functional characteristics of viruses that may be present within the sample. These characteristics can be used, for example, for establishing relationships between the composition of the sample and the physiological state of the biological source of the sample, e.g., the state of health or disease of a subject, such as a human subject. These characteristics can also be used to design experimental conditions for subsequent fractionation of the mixtures into subsets enriched in the molecule(s) of interest for the purpose of the analysis, while simultaneously reduced in the total number of different molecule(s) in some cases. Certain systems and methods can also be useful for detecting, classifying, and/or predicting changes in samples containing viruses. For example, the sample may be one associated with a particular disease or physiological state of a living organism, cells, tissues, or biological liquids. Certain systems and methods can also be used to detect changes to viruses in a biological sample and these changes could further be used to detect and classify a diagnostic that is related to such changes.

Examples of such changes in a mixture can be the differences in a property of a virus of the mixture, such as its conformation, structure and/or interaction tendency with respect to another molecule or molecules (e.g., its binding affinity or other interaction characteristic with respect to another molecule or molecules). For example, if the mixture includes viruses, such changes may be induced through primary sequence modification, by degradation of the virus through chemical, thermal, or other degradation mechanisms, by interaction with other molecules and/or biomolecules, by interaction with low molecular weight compounds (e.g., hormones, peptides, vitamins, cofactors, etc.), by changes in the relative content or concentration of the constituents of the mixture, by reactions such as enzymatic reactions, etc. Some systems and methods can be used, in certain cases, to detect, analyze and/or characterize biological materials as they interact with viruses, including but not limited to, polypeptides, proteins, carbohydrates, nucleic acids, polynucleotides, lipids, sterols, and mixtures or derivatives thereof, e.g., for the purpose of detection of, or onset of, a particular disease or physiological state, monitoring its progress, treatment, etc.

Comparison and classification steps involved in the disclosure can make use of additional information not necessarily related to (not directly derived from) the analytical methods of the disclosure. For example, blood pressure, temperature, blood glucose level, and/or essentially any other measurable physiological condition can be used in conjunction with various techniques of the disclosure to analyze one or more diseases or conditions.

It will be recognized by those of ordinary skill in the art that these biological materials can be found in any suitable form, for example, in the form of extracts from natural sources, biological liquids, collections of molecules generated by combinatorial chemical or biochemical techniques and combinations thereof, synthetically created, etc. In one set of embodiments, the biological materials arise from a biological fluid (e.g., withdrawn from a subject), and such biological materials may include one or more viruses suspected of being present within the subject, e.g., the subject may be suspected of being infected by one or more viruses. In some embodiments, the viruses may not be suspected of being present within the biological materials, e.g. during routine screening.

In one embodiment, the present disclosure provides a method to determine certain conditions under which variations among samples representing different species (e.g., viruses), or mixtures of species could be detected, i.e., determining a set of criteria and/or system components as a "tool," or a part of a tool, to determine information, as well as the subsequent use of the tool. For example, the ability of a system to determine a partition coefficient or a relative measure of interaction between a species, such as a virus, and one or more interacting components that can define one or more phases of the system can serve as an important tool or component of such a tool. Specifically, as one example, the partitioning of the constituents of a sample between two phases having different chemical or biochemical affinities or other characteristics, such as solvent structures, may separate the constituents by their relative affinity for media of different properties or composition. This separation technique thus can include or, alternatively, can be unlike those typically used in proteomics or similar techniques, e.g., 2-D gel electrophoresis, in which charge and size differences are the two dimensions used to separate the constituents of a sample. Some embodiments provide the ability for performing sequential or serial partitioning, with either the same of different conditions, which may result in additional amplification of differences in the fractionated samples. These fractions may be further analyzed using standard proteomics techniques.

As mentioned elsewhere herein, aqueous multi-phase (e.g., two-phase) partitioning systems are well-suited for use in many or most embodiments of the disclosure, but other partitioning systems can be used. Where terms such as "aqueous two-phase partitioning" or "aqueous multi-phase partitioning" is used, it is to be understood that other systems can be used in other embodiments, such as those described herein. Partitioning of a biopolymer in aqueous two-phase systems may depend on its three-dimensional structure, type and topography of chemical groups exposed to the solvent, etc. Changes in the 3-D structure of a receptor induced by some effect, e.g., by binding of a ligand binding or by structural degradation, also can change the topography of solvent accessible chemical groups in the biomolecule, or both the topography and the type of the groups accessible to solvent. One result of these changes may be an alteration in the partition behavior of the biomolecule or other species.

Viruses can be determined to diagnose or determine an underlying physiological condition or disease. Rapid and specific quantification techniques are readily available to those of ordinary skill in the art which can be used to quantify the concentration of viruses using standard methods and techniques directly in the biological sample, e.g., using antibodies in an Enzyme Linked ImmunoSorbent Assay (ELISA). The concentrations in the two interacting components of each system can be used to calculate the values of the partition coefficients. Changes to the individual values of the partition coefficients thus may indicate certain changes to the viruses. In some cases, the change to the partition coefficient of one or more viruses, can result in a definitive diagnosis of a disease or condition. In yet other cases, partitioning of the samples in multiple systems and performing the steps above, then observing the pattern of values for one or more viruses, can provide an alternative way to constructing a sensitive and specific diagnostics method.

Thus, for example, a sample may be obtained from a subject, and partitioned in one or more aqueous two-phase (or multi-phase) partitioning systems. Partition coefficients for one or more viruses may be determined, and used to determine a physiological condition of the subject, e.g., determining the presence and/or risk level of viruses in a subject. In some cases, the partition coefficients may be compared to reference partition coefficients, e.g., reference values previously determined for biomolecules taken from subjects with and without a disease or condition, e.g., viral infections.

For example, in connection with certain aspects, a variety of studies can take place. For example, the studies may include determining analysis procedures that involve taking samples from a single subject or multiple subjects. For example, a subject may be suspected of being infected by a virus. For instance, in one embodiment, the type of virus may be determined as described herein. For example, a coronavirus may be distinguishable from an influenza or other type of virus.

Similarly, changes may be detected using other systems and methods which have an underlying dependence upon the topography and/or the types of solvent accessible groups. Examples of such other methods include, but are not limited to, column liquid-liquid partition chromatography (LLPC), a heterogeneous two-phase system, or a multi-phase heterogeneous system. In some cases, an apparent partition coefficient may be generated that expresses the relative changes in the average partitioning between a first and a second phase, e.g., of a virus. For example, in LLPC, the retention volume of a receptor may be used as the apparent partition coefficient.

As previously discussed, aqueous two-phase partitioning systems may be used in various aspects of the disclosure to determine one or more viruses (or other species). For instance, one or more viruses may be determined within an aqueous two-phase partitioning system, e.g., by determining the amount and/or concentration of the viruses in each of the phases using techniques such as those described herein.

Aqueous multi-phase systems are well-known to those of ordinary skill in the art, and can arise in aqueous mixtures of different water-soluble polymers or a single polymer and a specific salt. When two or more certain polymers, e.g., dextran ("Dex") and polyethylene glycol ("PEG"), or one or more certain polymers and one or more inorganic salts, e.g. polyvinylpyrrolidone ("PVP") and sodium sulfate, are mixed in water above certain concentrations, the mixture can separate into two (or more) immiscible aqueous phases under certain conditions. There may be, in certain instances, a discrete interfacial boundary separating any two phases, for example, such that one is rich in one polymer and the other phase is rich in the other polymer or the inorganic salt. The aqueous solvent in one or more phases may provide a medium suitable for biological products. Two-phase systems can also be generalized to multiple phase system by using different chemical components, and aqueous systems with a dozen or more phases are known in the art.

When a species, such as a virus, is introduced into such a two-phase system, it may distribute between the two phases, and this understanding can be extended to three or more phases. In this and other systems, the species can be found at different concentrations within each phase, or can be at the same concentration within each phase. Partitioning of a solute can be characterized by the partition coefficient "K," defined as the ratio between the concentrations of the solute the two immiscible phases at equilibrium. It has previously been shown that phase separation in aqueous polymer systems may result from different effects of two polymers (or a single polymer and a salt) on the water structure (B. Zavlaysky, *Aqueous Two-Phase Partitioning: Physical Chemistry and Bioanalytical Applications*, Marcel Dekker, New York, 1995). As the result of the different effects on water structure, the solvent features of aqueous media in the coexisting phases can differ from one another. The difference between phases may be demonstrated by techniques such as dielectric, solvatochromic, potentiometric, and/or partition measurements.

The basic rules of solute partitioning in aqueous two-phase systems have been shown to be similar to those in water-organic solvent systems (which can also be used as systems in the present disclosure). However, what differences do exist in the properties of the two phases in aqueous polymer systems are often very small, relative to those observed in water-organic solvent systems, as would be expected for a pair of solvents of the same (aqueous) nature. The small differences between the solvent features of the phases in aqueous two-phase or multi-phase systems can be modified so as to amplify the observed partitioning that results when certain structural features are present.

It is known that the polymer and salt compositions of each of the phases usually depend upon the total polymer and/or salt composition of an aqueous two-phase system. The polymer and/or salt composition of a given phase, in turn, usually governs the solvent features of the aqueous media in this phase. These features include, but are not limited to, dielectric properties, solvent polarity, ability of the solvent to participate in hydrophobic hydration interactions with a solute, ability of the solvent to participate in electrostatic interactions with a solute, and hydrogen bond acidity and basicity of the solvent. All these and other solvent features of aqueous media in the coexisting phases may be manipulated by selection of polymer and salt composition of an aqueous two-phase system. These solvent features of the media may govern the sensitivity of a given aqueous two-phase system toward a particular type of solvent accessible chemical groups in the receptor. This sensitivity, type, and topography of the solvent accessible groups in two different proteins, for example, can determine the possibility of separating proteins in a given aqueous two-phase system.

In some cases, a particularly sensitive system may be required, i.e., a system that is very sensitive to, and able to determine a partition coefficient or a relative measures of interaction with respect to, two very similar species. This sensitivity may be of importance when, for example, subtle differences are being detected between the conformational changes in a receptor induced by binding of closely related chemical compounds. The present disclosure provides, in one set of embodiments, efficient and successful systems and methods for screening aqueous phase compositions to identify and/or amplify differences between the compositions of two mixtures. By utilizing a wide variety of different conditions to screen each molecule, as described herein, different partitioning behavior may be obtained reliably without the need to fully understand the underlying theory of aqueous two-phase partitioning, or any of the other related or substitutable techniques.

Viruses may be distributed between the two or more phases when placed into such a system. For example, in the case where phase-forming polymers are used, solutions comprising one or more of the two polymers and a virus may be mixed together such that both phase-forming polymers and the virus are mixed. The resulting solution is resolved and a two-phase system is formed. Optionally, centrifugation can be used to enhance separation of the phases. It will be recognized by those of ordinary skill in the art that partitioning behavior of a virus may be influenced by many variables, such as the pH, the polymers used, the salts used, factors relating to the composition of the system, as well as other factors such as temperature, volume, etc. Optimization of these factors for desired effects can be accomplished by routine practice by those of ordinary skill in the relevant arts, in combination with the current disclosure. In addition, as previously discussed, the partitioning behavior of a virus may be altered, for example, using a targeting species able to bind to the virus, e.g., selectively.

Evaluation of data from partitioning of a virus can involve use of the partition coefficient, in some embodiments of the disclosure. (However, it should be understood that partition coefficients are not always required.) For example, the partition coefficient of a virus can be taken as the ratio of the virus in first phase to that in the second phase in a biphasic system. When multiple phase systems are formed, there can be multiple independent partition coefficients, each of which can be defined between any two phases. It will be recognized that the partition coefficient for a given virus may be constant if the conditions and the composition of the two-phase system to which it is subjected remain constant. Thus, if changes are observed in the partition coefficient for a virus upon addition of a potential binding partner (for example, an antibody), these changes can be presumed to result from changes in the virus structure caused by formation of a complex with the virus. The partition coefficient K, as used herein, is a specifically mathematically defined quantity as further described herein, and the term includes coefficients representing the relative measure of interaction between a species, such as a virus, and at least two interacting components. It should also be recognized that differences between partition coefficients of different species in two or more mixtures could indicate, in addition to potential structural changes, also binding or lack of binding of such species to other species in the mixtures.

In a non-limiting example of one partitioning system, aqueous multi-phase systems are known to be formable from a variety of substances. For example, in order to determine the partition coefficient of a virus (or a mixture of viruses) to be analyzed, concentrated stock solutions of all the components (polymer 1, e.g., dextran; polymer 2, e.g., PEG, polyvinylpyrrolidone, salts, etc.) in water can be prepared separately. The stock solutions of phase polymers, salts, etc. can be mixed in the amounts and conditions (e.g., pH from about 3.0 to about 9.0, temperature from about 4° C. to 60° C., salt concentration from 0.001 to 5 mol/kg) appropriate to bring the system to the desired composition and vigorously shaken. The system can then be allowed to equilibrate (resolve the phases). Equilibration can be accomplished by allowing the solution to remain undisturbed, or it can be accelerated by centrifugation, e.g., for 2-30 minutes at about 1000 g to 4000 g, or higher. Aliquots of each settled (resolved) phase can be withdrawn from the upper and/or lower phases (or from one or more phases, if multiple phases are present). The concentration of viruses within the phases can be determined for one or more of the phases.

Different assay methods may be used to determine partition coefficients between a species (such as a virus) and interacting components, e.g. in the form of the concentration of the viruses in each phase of a multi-phase system. The assays will often depend upon the identity and type of viruses or other viruses present. Examples of suitable assay techniques include, but are not limited to, spectroscopic, immunochemical, chemical, fluorescent, radiological and enzymatic assays. In some cases, a virus may be determined by determining a peptide or protein associated with the virus. Non-limiting examples, include peplomers, envelope proteins, membrane proteins, nucleocapsids, etc. of coronaviruses, or hemagglutinin or neuraminidase of influenza viruses. Such peptides or proteins may be determined, for example, using suitable antibodies able to interact with these. For example, certain immunochemical assays can be used in some cases, e.g., ELISA. In addition, other peptide or protein detection techniques can be used in certain embodiments. These include, but are not limited to, direct spectrophotometry (e.g., monitoring the absorbance at 280 nanometers) and dye binding reactions with Coomassie Blue G-250 or fluorescamine, o-phthaldialdehyde, or other dyes and/or reagents.

The concentration of a species, such as a virus, in each phase can be used to determine the partition coefficient of the sample under the particular system conditions. Since the partition coefficient reflects the ratio of the two concentrations, the absolute values are not typically required. It will be recognized that this can allow certain analytical procedures to be simplified, e.g., calibration can be eliminated in some instances. It also may have significant advantage for negating the effect of natural variability in the absolute concentration in samples obtained from, e.g., various subjects, when comparing two or more samples, thus focusing on those changes detected as differences in the partition coefficient relevant to changes to the structure of the individual species in the samples.

It should be recognized by those skilled in the art that the steps in above description of obtaining the partition coefficient could be substituted by other steps or measurements. Depending on the size, volumes, amount of the virus, detection system, discrete or continuous operation using either liquid-liquid or liquid-solid portioning, other processes that effectively result in results described herein could be developed. Such modifications and different processes should not limit the scope of this complete disclosure.

The partition coefficient can be compared with other partition coefficients in some cases. For example, a partition coefficient for a virus can be compared to the partition coefficients for the virus under different conditions, a partition coefficient for a virus can be compared to the partition coefficients for the virus when combined with other viruses, a set of partition coefficients for a species can be compared to other sets of partition coefficients, etc. This comparative information can be obtained at the same time or near the same time and in the same system or a similar system as is used to determine the interaction characteristics of the virus, or can be provided as pre-prepared data in the form of charts, tables, or electronically stored information (available on the Internet, disc, etc.)

In one embodiment, proteins or other biomolecular mixtures from an experimental sample and from a reference sample (determined simultaneously, previously, or subsequently, as described above) may be caused to partition in a variety of different aqueous two-phase systems, e.g. formed by different types of polymers, such as Dextran and PEG or Dextran and Ficoll, by the same types of polymers with different molecular weights, such as Dextran-70 and PEG-600 or Dextran-70 and PEG-8,000, by the same polymers but containing different in type and/or concentration salt additives, different buffers of different pH and concentration, etc. The overall partition coefficients for the mixtures determined using a particular assay procedure (e.g., same for both samples) can be determined in all of the systems. In one embodiment, the systems displaying different partition coefficients for the mixtures under comparison may be selected as a separation medium, for example, for further fractionation and/or characterization of the mixtures. In another embodiment, mixtures are partitioned using one or more standard systems with known properties, e.g., those providing enhanced sensitivity levels towards hydrophobic or ionic interactions. In such a case, the individual partition coefficients of the species comprising the mixtures may be determined following separation of the mixtures in the phases and/or compared between two or more mixtures.

The reasons for the observed differences in the partition behavior of the two samples do not have to be scientifically characterized for such differences to be useful for many applications, e.g., for diagnostics. Such differences, resulting in partitioning behavior, may arise due to multiple reasons, including relative compositional, structural, or conformational differences in the samples when exposed to aqueous media of different solvent structures.

In some embodiments, one or more of the fluid manipulations may occur within a microfluidics device. "Microfluidic," as used herein, refers to a device, article, or system including at least one fluid channel having a cross-sectional dimension of less than about 1 mm. The "cross-sectional dimension" of the channel is measured perpendicular to the direction of net fluid flow within the channel. Thus, for example, some or all of the fluid channels in an article can have a maximum cross-sectional dimension less than about 2 mm, and in certain cases, less than about 1 mm. In one set of embodiments, all fluid channels in an article are microfluidic and/or have a largest cross sectional dimension of no more than about 2 mm or about 1 mm. In certain embodiments, the fluid channels may be formed in part by a single component (e.g. an etched substrate or molded unit). Of course, larger channels, tubes, chambers, reservoirs, etc. can be used to manipulate in other embodiments of the disclosure. In one set of embodiments, the maximum cross-sectional dimension of the channels in an article is less than about 1 mm, less than about 500 micrometers, less than about 300 micrometers, less than about 200 micrometers, less than about 100 micrometers, less than about 75 micrometers, less than about 50 micrometers, less than about 30 micrometers, less than about 25 micrometers, less than about 20 micrometers, less than about 15 micrometers, less than about 10 micrometers, less than about 5 micrometers, less than about 3 micrometers, less than about 2 micrometers, less than about 1 micrometer, less than about 500 nm, less than about 300 nm, less than about 100 nm, or less than about 50 nm. In some cases, suitable microfluidics devices may be readily obtained commercially.

In addition, according to some aspects of the present disclosure, a computer and/or an automated system is provided able to automatically and/or repetitively perform any of the methods described herein. As used herein, "automated" devices refer to devices that are able to operate without human direction, i.e., an automated device can perform a function during a period of time after any human has finished taking any action to promote the function, e.g. by entering instructions into a computer. Typically, automated equipment can perform repetitive functions after this point in time. One specific example of a technique that can make use of a computer or other automated system is in a process in which a physiological condition of a system as determined by determining a relative measure of interaction between one or more species from a sample from the system and various interacting components of a partitioning system. In the clinical setting, this may be accomplished by drawing a sample of blood (milliliter-sized or a very small sample such as a drop or less) and subjecting the blood sample or a subset thereof (e.g., plasma) to a multi-phase partitioning process. The results of this process can then be compared to similar behavior of markers in a similar system, which can take the form of data stored electronically.

Various embodiments of the present disclosure can also be implemented exclusively in hardware, or in a combination of software and hardware. For example, in one embodiment, rather than a conventional personal computer, a Programmable Logic Controller (PLC) is used. As known to those skilled in the art, PLCs are frequently used in a variety of process control applications where the expense of a general purpose computer is unnecessary. PLCs may be configured in a known manner to execute one or a variety of control programs, and are capable of receiving inputs from a user or another device and/or providing outputs to a user or another device, in a manner similar to that of a personal computer. Accordingly, although embodiments of the present disclosure are described in terms of a general purpose computer, it should be appreciated that the use of a general purpose computer is exemplary only, as other configurations may be used.

"Aqueous," as used herein, refers to the characteristic properties of a solvent/solute system wherein the solvating substance has a predominantly hydrophilic character. Examples of aqueous solvent/solute systems include those where water, or compositions containing water, are the predominant solvent.

"Partitioning system," as used herein, refers to any material having at least two phases, sections, areas, components, or the like, at least two of which can interact differently with at least one species to which they are exposed. For example, a partitioning system can include different areas of a solid surface, which can interact differently with a particular molecule exposed to the different sections, a multi-phase system such as a multi-phase liquid system, e.g., an aqueous/non-aqueous system or an aqueous multi-phase system (as defined herein) to which one or more species can be exposed and optionally dissolved, at least some of which species can interact differently with different phases. For example, a particular species may have a greater affinity for one phase rather than another phase to the extent that a multi-phase partitioning system can isolate a species from a mixture, or cause a species to partition at least in some way differently between the phases.

"Aqueous multi-phase system," as used herein, refers to an aqueous system which includes greater than one aqueous phase in which a species can reside, and which can be used to characterize the structural state of the species according to the methods described herein. For example, an aqueous multi-phase system can separate at equilibrium into two, three, or more immiscible phases. Aqueous multi-phase systems are known in the art and this phrase, as used herein, is not meant to be inconsistent with accepted meaning in the art. Examples of various aqueous multi-phase systems, and their compositions, are discussed herein.

An "interacting component" means a component, such as a phase of multi-phase system, that can interact with a species and provide information about that species (for example, an affinity for the species). Multiple interacting components, exposed to a species, can define a system that can provide a "relative measure of interaction" between each component and the species. An interacting component can be aqueous or non-aqueous, can be polymeric, organic (e.g. a protein, small molecule, etc.), inorganic (e.g. a salt), or the like, or any combination thereof. A set of interacting components can form a system useful in and in part defining any experimental method which is used to characterize the structural state of a species according to the methods described herein. Typically, a system of interacting components can measure the relative interaction between the species and at least two interacting components. An aqueous multi-phase system is an example of a system of interacting components, and it is to be understood that where "aqueous system" or "aqueous multi-phase system" is used herein, this is by way of example only, and any suitable system of interacting components can be used.

Where aqueous two-phase and aqueous multi-phase systems are described herein, it is to be understood that other systems, as used herein, systems analogous to those comprising only aqueous solutions or suspensions can be used. For example, an aqueous two-phase system can include non-aqueous components in one or more phases that are not liquid in character. In this aspect, multi-phase systems also refers to related techniques that rely on differential affinity of the biomolecule to one media versus another, wherein the transport of the biomolecule between one medium and, optionally, another medium occurs in an aqueous environment. Examples of such multi-phase systems include, but are not limited to, HPLC columns or systems for liquid-liquid partition chromatography, as are known to those of ordinary skill in the art.

"Relative measure of interaction," with reference to a particular species as used herein, means the degree to which the species interacts with another species or with a phase of a multi-phase system in a relative sense. For example, a particular species may have a greater affinity for one phase of a multi-phase system rather than another phase or phases, the degree to which it interacts with or resides in, that phase as opposed to other phases defines its relative measure of interaction. Relative measures of interaction, in the context of the present disclosure, are generally determined in a ratiometric manner, rather than an absolute manner. That is, where a species can interact with each phase of a two-phase system but resides more preferably in one than the other, the present disclosure typically makes use of information as to the ratio of concentration of the species in each of the two phases, but not necessarily of the absolute concentration of the species in either phase. In other cases, the interaction can be an interaction based not upon residence of a particular species within a particular solvent or fluid carrier, but interaction with a solid surface such as a solid phase of a chromatography column where the relative measure manifests itself in elution time, or can involve geometric or spatial interaction such as a particular species interaction with a porous substrate as opposed to that of a different species or a different substrate.

"Partition coefficient," as used herein, refers to the coefficient which is defined by the ratio of chemical activity or the concentrations of a species in two or more phases of a multi-phase system at equilibrium. For example, the partition coefficient (K) of a species in a two-phase system can be defined as the ratio of the concentration of species in the first phase to that in the second phase. For multi-phase systems, there can be multiple partition coefficients, where each partition coefficient defines the ratio of species in first selected phase and a second selected phase. It will be recognized that the total number of partition coefficients in any multi-phase system will be equal to the total number of phases minus one.

For heterogeneous phase systems, an "apparent partition coefficient," as used herein, refers to a coefficient which describes information obtained from alternative techniques that is correlated to the relative partitioning between phases. For example, if the heterogeneous two-phase system used is an HPLC column, this "apparent partition coefficient" can be the relative retention time for the species. It will be recognized by those of ordinary skill in the art that the retention time of a species, in such a case, reflects the average partitioning of the species between a first, mobile phase and a second, immobile phase. Also, it will be recognized that other, similarly determinable properties of species can also be used to quantify differences in physical properties of the species (e.g. in other techniques) and are, therefore, suitable for use as apparent partition coefficients.

"Bind," as used herein, means the well-understood receptor/ligand binding, as well as other nonrandom association between a biomolecule and its binding partner. "Specifically bind," as used herein, describes a binding partner or other ligand that does not cross react substantially with any biomolecule other than the biomolecule or biomolecules specified. Generally, molecules which preferentially bind to each other are referred to as a "specific binding pair." Such pairs include, but are not limited to, an antibody and its antigen, a lectin and a carbohydrate which it binds, an enzyme and its substrate, and a hormone and its cellular receptor. As generally used, the terms "receptor" and "ligand" are used to identify a pair of binding molecules. Usually, the term "receptor" is assigned to a member of a specific binding pair, which is of a class of molecules known for its binding activity, e.g., antibodies. The term "receptor" is also preferentially conferred on the member of a pair that is larger in size, e.g., on lectin in the case of the lectin-carbohydrate pair. However, it will be recognized by those of skill in the art that the identification of receptor and ligand is somewhat arbitrary, and the term "ligand" may be used to refer to a molecule which others would call a "receptor." The term "anti-ligand" is sometimes used in place of "receptor."

"Molecule-molecule interaction," such as biomolecule-biomolecule interaction, protein-protein interaction, and the like means an interaction that typically is weaker than "binding," i.e., an interaction based upon hydrogen bonding, van der Waals binding, London forces, and/or other non-covalent interactions that contribute to an affinity of one molecule for another molecule, which affinity can be assisted by structural features such as the ability of one molecule to conform to another molecule or a section of another molecule. Molecule-molecule interactions can involve binding, but need not.

"Biomolecule," as used herein, means a molecule typically derived from a subject, and which typically includes building blocks including nucleotides, and the like. Examples include, but are not limited to, peptides, polypeptides, proteins, protein complexes, nucleotides, oligonucleotides, polynucleotides, nucleic acid complexes, saccharides, oligosaccharides, carbohydrates, lipids, etc., as well as combinations, enantiomers, homologs, analogs, derivatives and/or mimetics thereof.

"Species," as used herein, refers to a molecule or collection of molecules, for example, an inorganic chemical, an organic chemical, a biomolecule, or the like. In the present disclosure, species generally are biomolecules.

"Corresponding species," as used herein, means at least two different species that are identical chemically or, if they differ chemically and/or by molecular weight, differ only slightly. Examples of corresponding species include structural isoforms of proteins, proteins or other molecules that are essentially identical but that differ in binding affinity with respect to another species or plural species, have different higher-order structure, e.g., differing in secondary or tertiary structure but not differing or not differing significantly in chemical sequence. In general, corresponding species are species that may be arranged differently (isoforms, isomers, etc.) but are composed of the same or essentially the same chemical building blocks.

"Detectable," as used herein, refers the ability of a species and/or a property of the species to be discerned. One example method of rendering a species detectable is to provide further species that bind or interact with the first species, where the species comprise(s) a detectable label. Examples of detectable labels include, but are not limited to, nucleic acid labels, chemically reactive labels, fluorescence labels, enzymatic labels and radioactive labels.

"Mimetic," as used herein, includes a chemical compound, an organic molecule, or any other mimetic, the structure of which is based on, or derived from, a binding region of an antibody or antigen. For example, one can model predicted chemical structures to mimic the structure of a binding region, such as a binding loop of a peptide. Such modeling can be performed using standard methods (see, for example, Zhao et al., *Nat. Struct. Biol.* 2: 1131-1137 (1995)). The mimetics identified by methods such as this can be further characterized as having the same binding function as the originally identified molecule of interest, according to the binding assays described herein.

"Structure," "structural state," "configuration" or "conformation," as used herein, all refer to the commonly understood meanings of the respective terms, for example, as they apply to biomolecules such as proteins and nucleic acids, as well as pharmacologically active small molecules. In different contexts, the meaning of these terms will vary, as is appreciated by those of skill in the art. The structure or structural state of a molecule refers generally not to the building blocks that define the molecule but the spatial arrangement of these building blocks. The configuration or confirmation typically defines this arrangement. For instance, the use of the terms primary, secondary, tertiary or quaternary, in reference to protein structure, have accepted meanings within the art, which differ in some respects from their meaning when used in reference to nucleic acid structure (see, e.g., Cantor and Schimmel, *Biophysical Chemistry*, Parts I-III). Unless otherwise specified, the meanings of these terms will be those generally accepted by those of skill in the art.

"Physiological conditions," as used herein, means the physical, chemical, or biophysical state of a subject. As most typically used in the context of the present disclosure, physiological condition refers to a normal (e.g., healthy in the context of a human) or abnormal (e.g., in a diseased state in the context of a human) condition.

"Marker," as used herein, is a species that can be a carrier of information regarding a physiological state of a biological environment within which it resides. A marker can exhibit at least two different properties or values of a specific property or properties (e.g., structural conformation, binding affinity for another species, etc. but not solely different amounts of the species) that correspond to and/or that represent information regarding the two or more physiological states of environments within which they reside. For example, a marker may be a protein that is structurally modified between a first state representative of a healthy system within which it resides and a second structural state (different conformation) representative of a disease system within which it resides.

The following documents are incorporated herein by reference: U.S. Pat. No. 7,968,350, issued Jun. 28, 2011, entitled "Characterization of Molecules"; U.S. Pat. No. 8,099,242, issued Jan. 17, 2012, entitled "Systems and Methods for Characterization of Molecules"; International Patent Application No. PCT/US04/019343, filed Jun. 14, 2004, entitled "Systems and Methods for Characterization of Molecules," published as Int. Pat. Apl. Pub. No. WO 2004/111655 on Dec. 23, 2004; U.S. Pat. Apl. Pub. No. 2015-0219655, entitled "Methods and Devices for Analyzing Species to Determine Diseases"; U.S. Pat. Apl. Ser. No. 62/987,385, filed May 10, 2020, entitled "Systems and Methods for Determining Viruses such as Coronaviruses"; U.S. Pat. Apl. Ser. No. 62/982,880, filed Feb. 28, 2020, entitled "Systems and Methods for Determining Viruses such as Coronaviruses"; U.S. Pat. Apl. Ser. No. 62/987,385, filed Mar. 10, 2020, entitled "Systems and Methods for Determining Viruses such as Coronaviruses"; U.S. Pat. Apl. Ser. No. 63/071,472, filed Aug. 28, 2020, entitled "Systems and Methods for Determining Viruses such as Coronaviruses"; U.S. Pat. Apl. Ser. No. 63/091,849, filed Oct. 14, 2020, entitled "Systems and Methods for Determining Viruses such as Coronaviruses"; U.S. Pat. Apl. Ser. No. 63/000,441, filed Mar. 26, 2020, entitled "Determination of Viruses such as Coronaviruses Based on Viral Proteins"; and U.S. Pat. Apl. Ser. No. 63/003,843, filed Apr. 1, 2020, entitled "Determination of Viruses such as Coronaviruses Based on Viral Proteins."

The following examples are intended to illustrate certain embodiments of the present disclosure, but do not exemplify the full scope of the disclosure.

Example 1

COVID-19 (Coronavirus Disease 2019) screening and diagnostics represents multiple challenges and specific requirements, amongst these include:
Simple, rapid POC (point of care) test format
Low-cost (especially for wide-scale screening)
Ability to readily differentiate between influenza and other highly prevalent viruses and COVID-19.

This prophetic example customizes previously validated technology with a potential to address all the above requirements, based on differences in the structure of the virion that is specific to COVID-19 vs. other viruses, and not based on molecular differences in its RNA—the scientific modality that underlies all current technologies. This example detects and further classifies such differences using a novel technology that interrogates the virion structure via its differential interaction with two adjacent aqueous environments of different solvent properties serving as "structural reporters."

The unique combination of simplicity/true POC/low-cost makes the technology specifically attractive as a reflex screening test prior to molecular PCR-based confirmatory testing. Simply put, a screening test with very high (but not necessarily perfect) negative predictive value for COVID-19 virion that could be very widely deployed, combining the above characteristics, may solve the logjam presented by requiring all people presenting with non-specific fever or other clinical symptoms to undergo slow molecular testing or submit to quarantine. Such a test could serve as a true POC filter to screen all people presenting with non-specific symptoms to differentiate, e.g., influenza, from COVID-19. Those who could not be ruled out as negatives could then be directed to second-tier diagnostics using definitive molecular testing. This schema is especially attractive for infections with high $r_0$ and potentially long incubation period such as COVID-19, given the practical impossibility of extremely wide availability of molecular-based testing and/or quarantine on a national scale.

Aqueous two-phase partitioning is an analytical technology in which aqueous mixture of polymers, salts, and other additives is designed to naturally phase separate into two distinct phases called top and bottom phases. These two phases have different physicochemical/intermolecular solvent properties. Any solute—small or large molecule, cell, or a virus—that is mixed with the system and then allowed to equilibrate may then partition between the two phases in unequal concentrations, depending on its 3D structure and its molecular interactions with the different solvent structures in the two phases. While the intermolecular solvent/solute molecular interactions are very complex, the assay itself is very simple: The ratio of the concentrations of the solute in the two phases is called the partition coefficient, K, and is a numerical index specific to the aqueous partition system composition—and to the 3D structure of the solute being interrogated. The chemistry of the system, and thus K, could be designed to exploit certain desired properties. For example, K could be made very large, meaning that a certain virion, e.g., COVID-19, would be found only the top phase but not in the bottom phase; but when another virion of different structure is present, e.g., influenza virion, it would be found in both of the aqueous phases. Other variations could be
designed as well as would be described below.

A typical aqueous partition protocol could be generally described by the following steps, as a non-limiting example. See also FIG. 7.
1. Obtain a sample of saliva (or any other easily accessible biofluid containing COVID-19, such as nasal fluid) from a patient. The absolute amount is not a critical parameter, since the index K is ratiometric and independent of the overall sample size or the viral load.
2. Add the sample into a small vial (typically a 2 mL tube) containing ready-to-use aqueous two phase system. Screw back the cap.
3. Shake or briefly agitate the tube.
4. Briefly spin using hand-held centrifuge to aid phase separation.
5. Examine approximate virion load in both phases using one of known assays, e.g.:
   a. A COVID-19 virus-binding moiety or targeting species such as peplomers, envelope/membrane proteins, spike glycoproteins, HE, etc. In other cases the nuclear material (RNA) may be used for determining the load.
   b. An influenza virus (A, B, C, D, Isavirus, etc.) virus-binding moiety or targeting species such as hemagglutinin, neuraminidase, nucleocapside, etc. In other cases the nuclear material (RNA) may be used for determining the load.

Any one of these targets could be determined with a host of available techniques using additional conventional signaling moiety such as a dye (colorimetric/fluorescent), ligand/enzymatic assisted reaction, etc. The specific choice of the assay is determined primarily by desired level of protocol simplicity and readout—the former may include simple addition of prepared dye to the mixture and the latter could involve detection of appearance of specific color in one of the two phases to the naked eye. It should be emphasized that since the overall test relies on structure-based isolation of CoVID-19 into one of the two phases differently than, e.g., influenza, there is no need for a quantitative determination of the actual viral load—only its existence in both phases or lack of existence in one of the phases to screen/diagnose.

6. Selection of appropriate visual or other cut-off values for the test could be determined using standard ROC methodologies with desired levels of negative or positive predictive values (PPV/NPV) appropriate for the population under study. The same test could be used for first line POC screening with simple visual determination per step 5 above, to be followed by a second test with a different cut-off using a lab read-out instrument and/or other orthogonal techniques (e.g., PCR, etc.) for diagnosis.

The entire protocol could be conducted in few minutes per sample, could be readily automated if needed, uses highly stable chemical reagents, and has COG (cost of goods) in the single dollar range. The readout instrument could be a simple colorimetric device onto which the entire tube is placed, or other POC format readers. In some cases, no sensor device is needed and the tube can be determined visually, e.g., as is shown in FIG. 7.

Example 2

This example tested the extent to which SARS CoV-2 or H1N1 migrates to the top or bottom phase in the provided tubes (labeled 1-10). An aliquot of the top and bottom phase of each tube is analyzed by plaque assay for the presence of the virus. The virus was SARS-CoV-2 UTHSC passage 3, (SARS-Related Coronavirus 2 Isolate USA-WA1/2020), and H1N1 (PR8). The titer of the stock viruses was $2\times10^6$ pfu/mL SARS CoV-2, and $1\times10^8$ pfu/mL, PR8. The inoculum of the viruses was $4\times10^4$ pfu, SARS CoV-2 and PR8. The cell line for the plaque assays were Vero E6 (SARS CoV2) and MDCK (PR8).

Results are as follows. Table 1 shows plaque assay results of ATS tubes 1-10 inoculated with SARS CoV-2. Table 2 shows plaque assay results of ATS tubes 1-10 inoculated with PR8.

It was found that SARS CoV-2 was present in the bottom phase only in ATS tubes 1, 2, 4, 5, 6, and 7. SARS CoV-2 was present in both top and bottom phases in ATS tubes 3, 8, 9, and 10. PR8 was present in the bottom phase only in tubes 1 and 2. PR8 was present in both phases in ATS tubes 3-10.

TABLE 1

| Tubes + COVID-19 | top phase pfu | dilution | pfu/mL |
|---|---|---|---|
| ATS-1 | 0 | | 0 |
| ATS-2 | 0 | | 0 |
| ATS-3 | 20 | 2 | 200 |
| ATS-4 | 0 | | 0 |
| ATS-5 | 0 | | 0 |
| ATS-6 | 0 | | 0 |
| ATS-7 | 0 | | 0 |
| ATS-8 | 9 | 2 | 90 |
| ATS-9 | 2 | 6 | 60 |
| ATS-10 | 20 | 6 | 600 |
| Tubes + COVID-19 | bottom phase pfu | dilution | pfu/mL |
| ATS-1 | 60 | 2 | 600 |
| ATS-2 | 55 | 2 | 550 |
| ATS-3 | 44 | 2 | 440 |
| ATS-4 | 66 | 6 | 1980 |
| ATS-5 | 60 | 2 | 600 |
| ATS-6 | 47 | 2 | 470 |
| ATS-7 | 91 | 2 | 910 |
| ATS-8 | 75 | 2 | 750 |
| ATS-9 | 39 | 2 | 390 |
| ATS-10 | 27 | 6 | 810 |

TABLE 2

| Tubes + PR8 | top phase pfu | dilution | pfu/mL |
|---|---|---|---|
| ATS-1 | 0 | | |
| ATS-2 | 0 | | |
| ATS-3 | 10 | 5 | 100 |
| ATS-4 | 17 | 5 | 170 |
| ATS-5 | 23 | 5 | 230 |
| ATS-6 | 41 | 5 | 410 |
| ATS-7 | 6 | 5 | 60 |
| ATS-8 | 37 | 5 | 370 |
| ATS-9 | 57 | 5 | 570 |
| ATS-10 | 39 | 5 | 390 |
| Tubes + PR8 | bottom phase pfu | dilution | pfu/mL |
| ATS-1 | 68 | 5 | 680 |
| ATS-2 | 42 | 5 | 420 |
| ATS-3 | 46 | 5 | 460 |
| ATS-4 | 52 | 5 | 520 |
| ATS-5 | 37 | 5 | 370 |
| ATS-6 | 54 | 5 | 540 |
| ATS-7 | 57 | 5 | 570 |
| ATS-8 | 52 | 5 | 520 |
| ATS-9 | 67 | 5 | 670 |
| ATS-10 | 62 | 5 | 620 |

Example 3

This example demonstrated the feasibility of AuNP (gold nanoparticles) readout system with coronavirus, including with 3 SIA candidates. In this example, AuNP-anti IgG conjugates and a S1/S2 mAb ELISA system were used. Negative control experiments were used, with each top and bottom phase of each of the 3 SIA systems. Positive controls with the virus were also used. In addition, positive aggregation experiments with each top and bottom phase of each of the 3 SIA systems were used.

FIG. 8 shows conjugate formation in various experiments (center wells). FIG. 8A shows an OD (optical density) (526 nm) of 0.29. FIG. 8B shows an OD (560 nm) of 0.29. Thus, these figures illustrate that the gold nanoparticles were able to bind to the virus.

FIG. 9 shows OD (a measure of aggregation) as a function of time for negative controls (no aggregation) (FIG. 9A), positive controls (FIG. 9B), and a system with the virus (FIG. 9C). FIG. 9D illustrates the change in optical density caused by aggregation of the virus particles with the gold nanoparticles.

Figure 10:
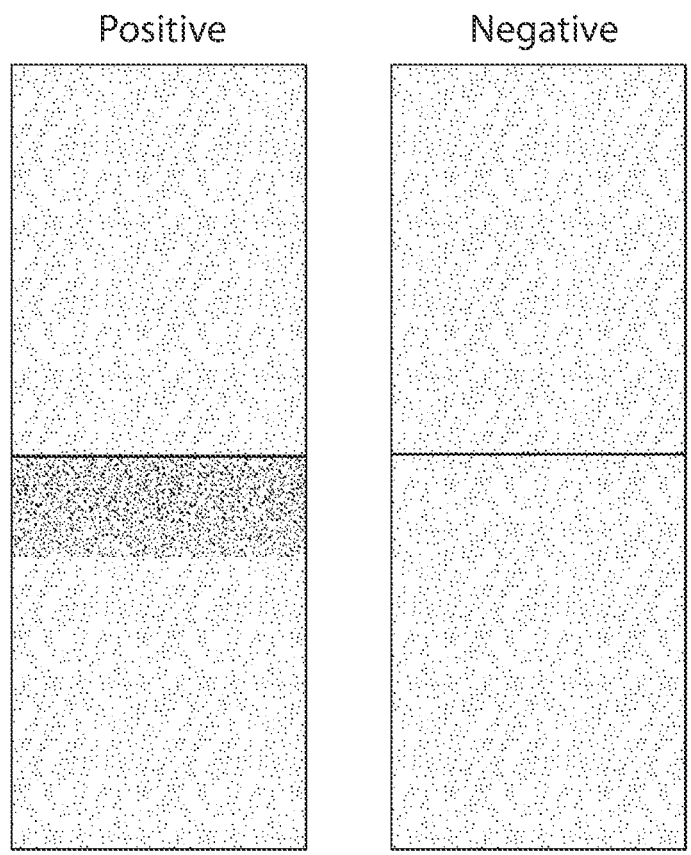
FIG. 10 illustrates positive and negative controls for aggregation of viruses, in accordance to certain embodiments.

FIG. 10 is a schematic diagram illustrating how positive and negative controls can be readily determined, e.g., using optical density, colorimetrically, visually (e.g., using the naked eye), etc.

Example 4

This example illustrates Aqueous Two-Phase Partitioning using Solvent Interaction Analysis (SIA), in accordance with another embodiment. This allows for sensitive, fully customizable technology for using tailored water structure to interrogate the 3D structure of any dissolved molecule/particle. This allows access to utilizing changes in intermolecular interactions (hydrogen bonding/ionic and electrostatic interactions, etc.) to observe macroscopic changes in partitioning of target, as well as fast, inexpensive, automation or manual operation, including with a variety of different assay formats.

Figure 7:
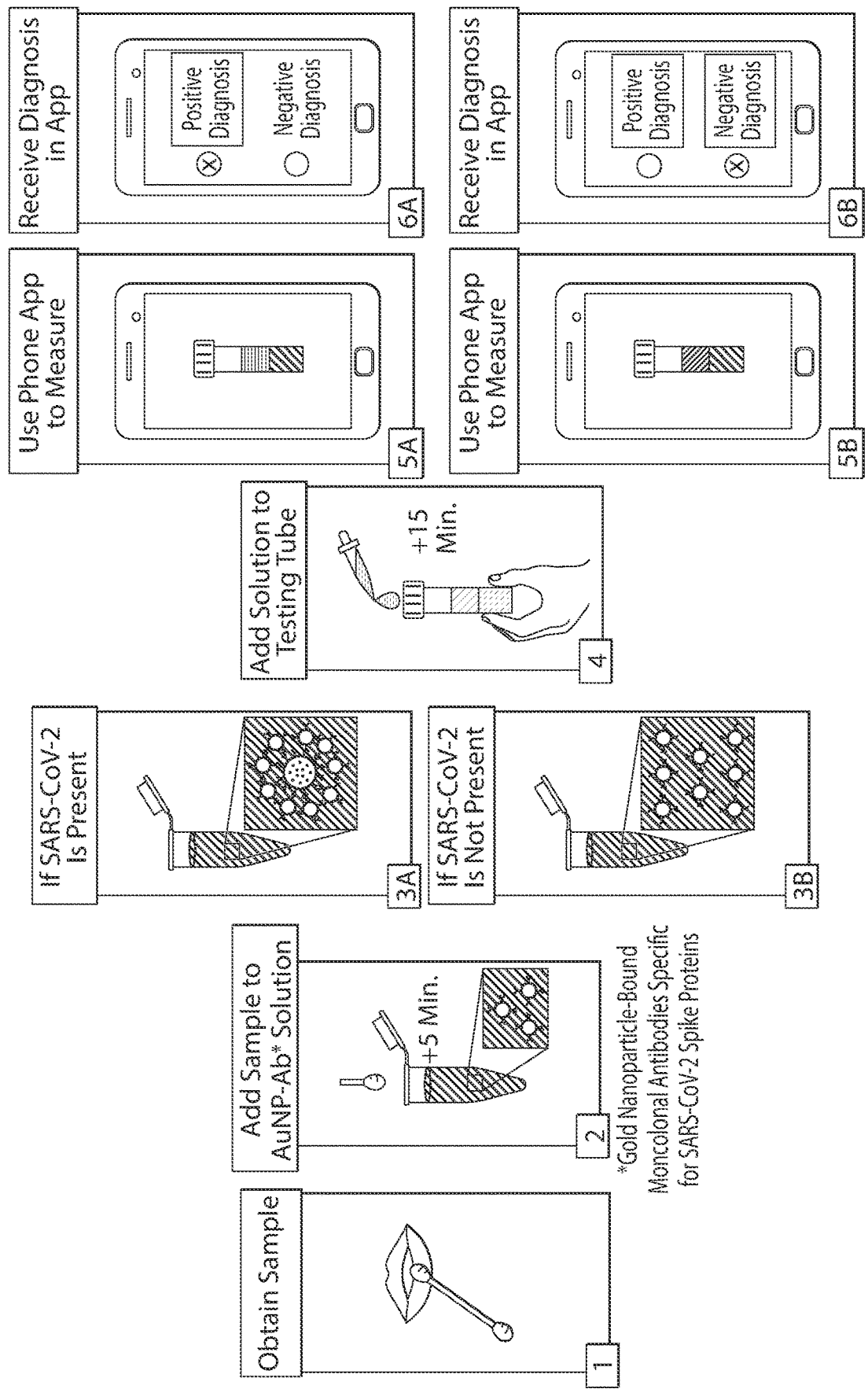
FIG. 7 illustrates a method of determining a virus, in one embodiment.
Figure 8A:
FIGS. 8A-8B illustrate conjugation of virus to gold nanoparticles, in various embodiments.
Figure 8B:
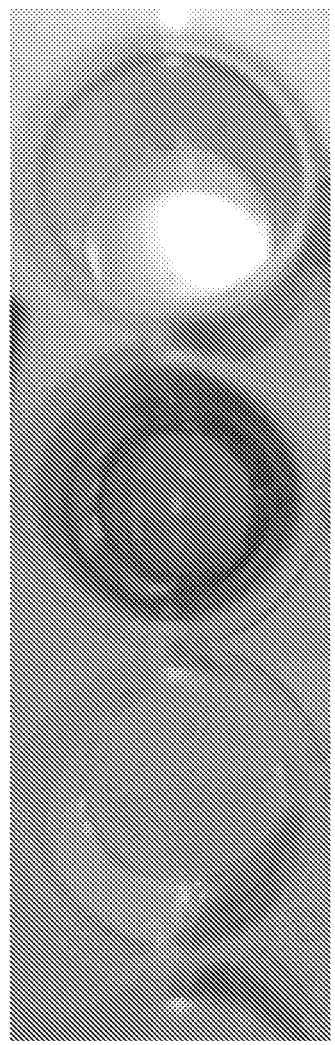
Figure 9A:
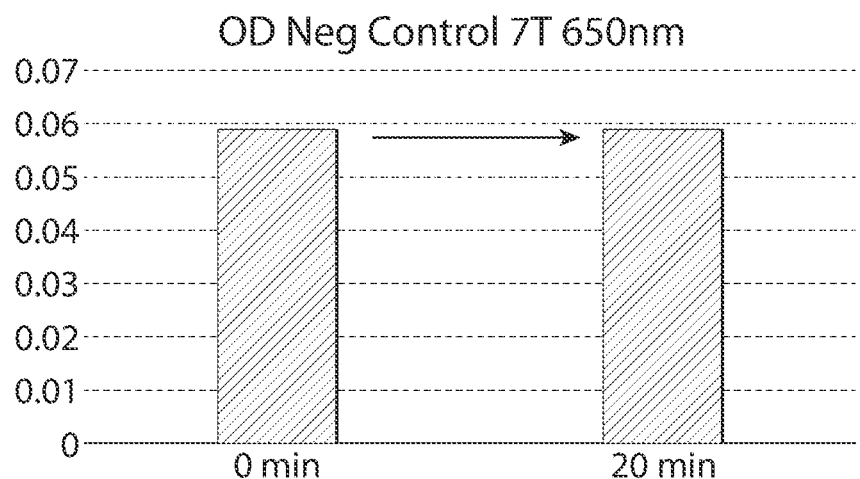
FIGS. 9A-9D illustrate aggregation of a virus to gold nanoparticles, in certain embodiments.
Figure 9B:
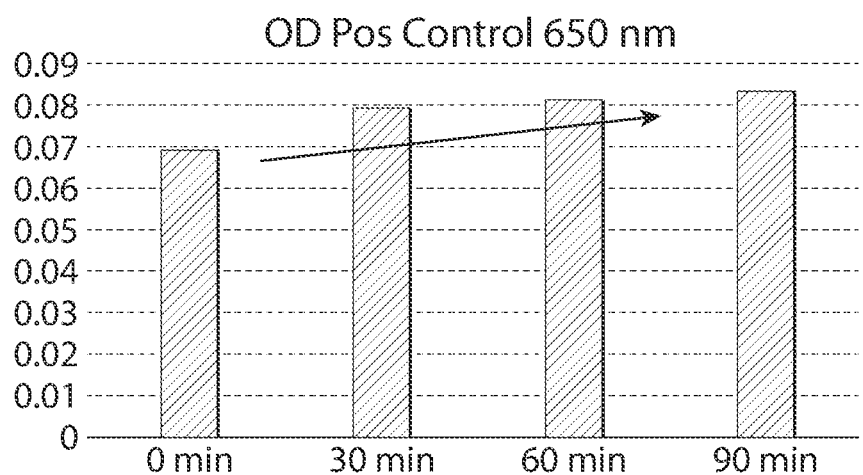
Figure 9C:
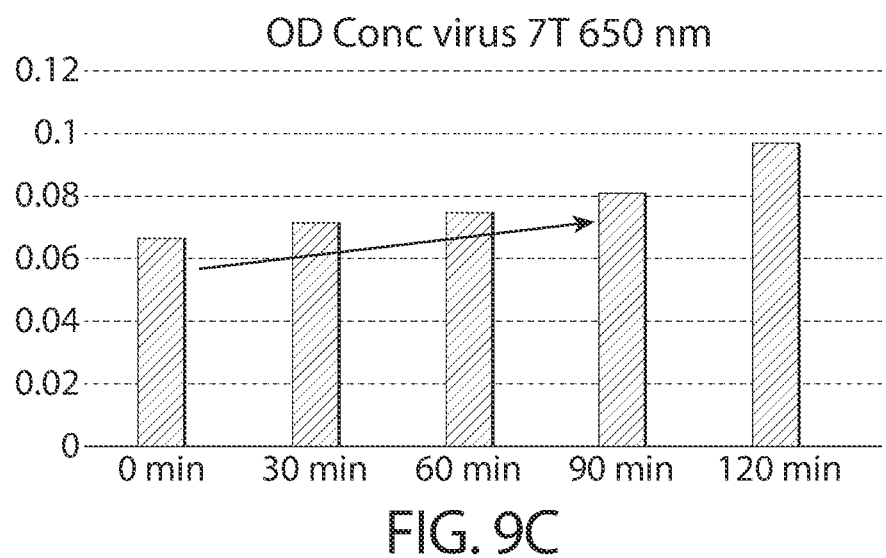
Figure 9D:
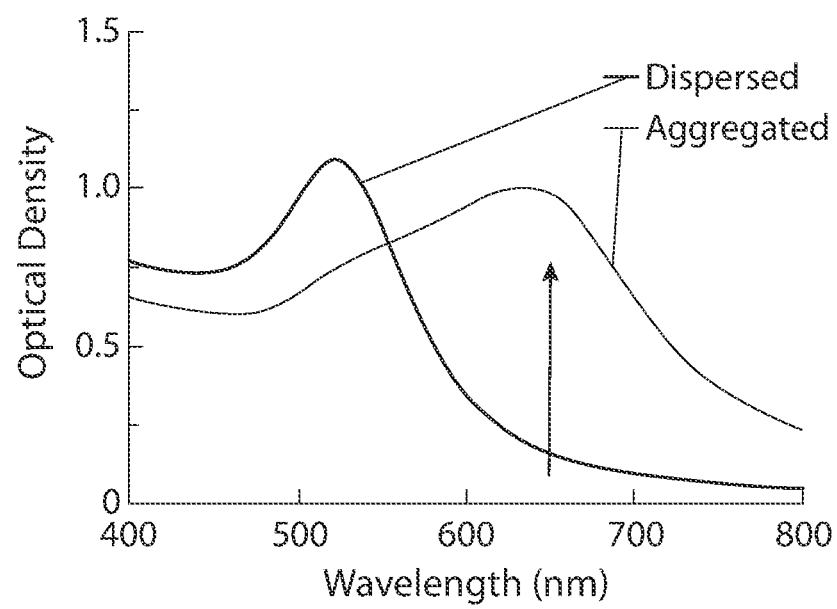

An example method is shown in FIG. 7. This method use AuNP-mAb (gold nanoparticles/monoclonal antibodies) for a readout. SIA is used to partition the AuNP-mAb-virion complex exclusively to the top phase. The SIA allows internal control, e.g., a color change must be observed, e.g., on the top phase. In some cases, automated diagnoses with a simple one picture colorimetric app can be obtained, e.g., using a cell phone.

The AuNP system illustrated here is an example of a readout system, although other readout systems may be used in other embodiments. The system shown in this example is relatively sensitive (e.g., it can detect 100-1,000 virions), and is coupled to molecular recognition via mAb. It changes color with the presence of the virus, allowing for simple, easy detection. The SIA system allows for structure-based recognition.

Figure 11:
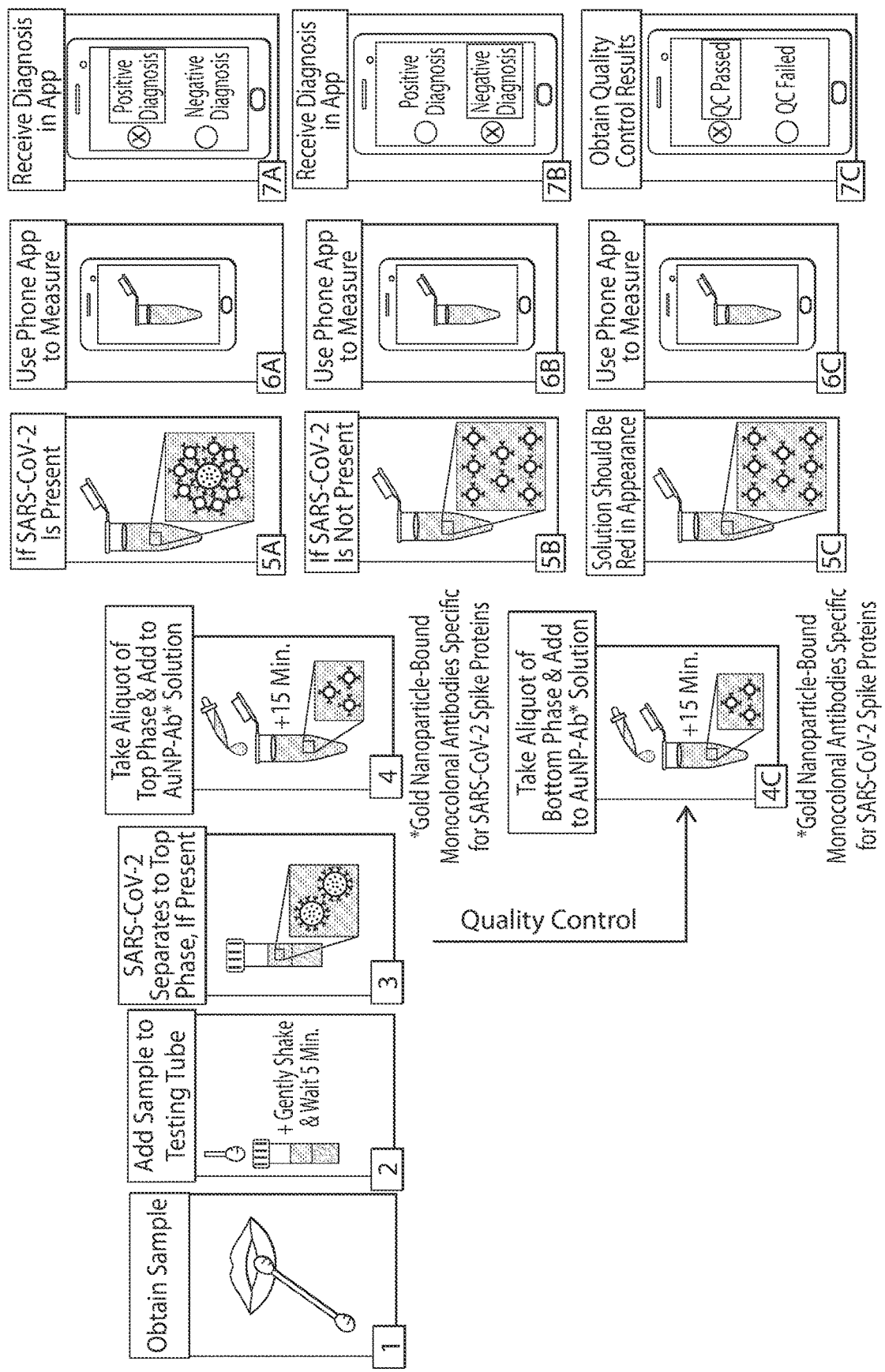
FIG. 11 illustrates a method of determining a virus, in another embodiment.

Another example method is shown in FIG. 11. This example uses AuNP-mAb for readout. The SIA is used to partition the SARS-CoV-2 virion to the top phase. SIA allows for an internal control, where a color change can be observed, and on top phase, and independently. The bottom phase may be negative. In some cases, automated diagnosis can be obtained with a simple, one-picture colorimetric app, e.g., using a cell phone. An additional QC (quality control) picture can also be obtained.

In some cases, 100-1,000 virions may be determined. For comparison, a typical swab sample contains more than $10^3$ virus particles. In some cases, high specificities may be obtained, e.g., based on mAb specificity and/or direct structural (3D) classification metrics.

Example 5

For COVID-19, one of the most important functions of diagnostic testing is to accurately categorize individuals who are negative for active coronavirus infection (symptomatic or asymptomatic) using an immediate result POC field test. Neither PCR (technical complexity, slow turnaround time) nor serology (inability to identify active disease, potential to mischaracterize immune status, overall diagnostic inaccuracy) provide the optimum solution to this critical public health need. This example illustrates a diagnostic platform, Solvent Interaction Analysis (SIA), that effectively addresses this public health problem. This platform can be used to rapidly identify SARS-CoV-2 based on an analysis of 3D shape, structure, and molecular signature. Combined with colorimetric gold-nanoparticle technology, the test kit is neatly comprised of a small plastic tube containing test reagents and an attachable specimen receiving device to obtain either self-collected saliva or, alternatively, saliva obtained by saturation of a swab. Saliva has been chosen as the appropriate test sample due to the documented presence of SARS-CoV-2 in this biologic fluid as well as other factors including but not limited to ease of collection, patient and provider acceptance, and the successful implementation of this medium in other commercially available assays. While SIA based SARS-CoV-2 assay uses saliva as the test sample biologic material in this example, other techniques such as nasopharyngeal swab or lavage specimens based on limit of detection (LOD) considerations and specifications can also be used.

Initially, the test output is detected several minutes after combining the sample with the test reagents as a color and intensity change when compared to a visual image analysis guide card providing a definitive detection result. Other embodiments of the test kit can use, for example, readily available smart phone colorimetry applications with integrated cloud based capability to allow rapid evaluation of clustering, tracing, location-based monitoring and alike, or a stand-alone hand-held laser diode based colorimetry detection device with similar cloud enabled data functionality. The assay is specifically designed to deliver very high sensitivity to active infection (low false negative rate), providing an effective screening test with superior exclusion power to allow widespread, easily accessible, repeatable testing to confirm the negative disease status of individuals.

COVID-19 diagnostic testing (screening and early detection) presents multiple challenges and has specific requirements, such as the following: a simple, rapid POC test format, ideally requiring little or no special equipment, a low-cost test platform (especially for wide-scale screening), a highly sensitive assay able to readily differentiate between influenza, other highly prevalent viruses, and SARS-CoV-2, a test that provides actionable clinical information regarding current infection (like PCR) as opposed to prior exposure (like serology), and/or an assay that addresses limitations of current testing modalities, e.g., accurately and rapidly detects active infection without the need for lab instrumentation (e.g. PCR) and provides real time diagnostic information in a POC kit format as opposed to information regarding exposure only (e.g. serology).

This example combines two orthogonal viral identification modalities. The first modality is the clinically validated Solvent Interaction Analysis (SIA) technology that addresses the above based on differences in the 3-dimensional structure of the virion that is specific to COVID-19, compared to other viruses, rather than only based on molecular differences in viral RNA or on downstream generation of antibodies to the virus. The second modality is a colorimetric readout to the virion which has been aggregated into a specific location within the test tube using viral identification unique to its spike protein with an antibody-gold nanoparticle conjugate system (see below). The functional virion structure is interrogated via its differential interaction with two adjacent aqueous environments of differing solvent properties serving as "structural reporters."

No additional instrumentation is needed to deliver information regarding the presence of active infection. The assay kit in this example includes a saliva sample collection tube with an attachable funnel (self-collected saliva specimen) or a valve membrane cap (saliva saturated swab), a 3 mL tube containing an SIA aqueous two-phase partitioning system with readout reagents (gold nanoparticle conjugated to mAb for the virion spike protein), a negative internal control, and a positive control). Initially, the test output is detected several minutes after combining the saliva sample with the test reagents as a color and intensity change when compared to a visual image analysis guide card providing a definitive detection result. Other embodiments that can be used for detection include smart phone colorimetry applications (apps), e.g., with integrated cloud based capability to allow rapid evaluation of clustering, tracing, location-based monitoring etc., or a stand-alone hand-held laser diode based colorimetry detection device, e.g., with similar cloud enabled data functionality.

Figure 12:
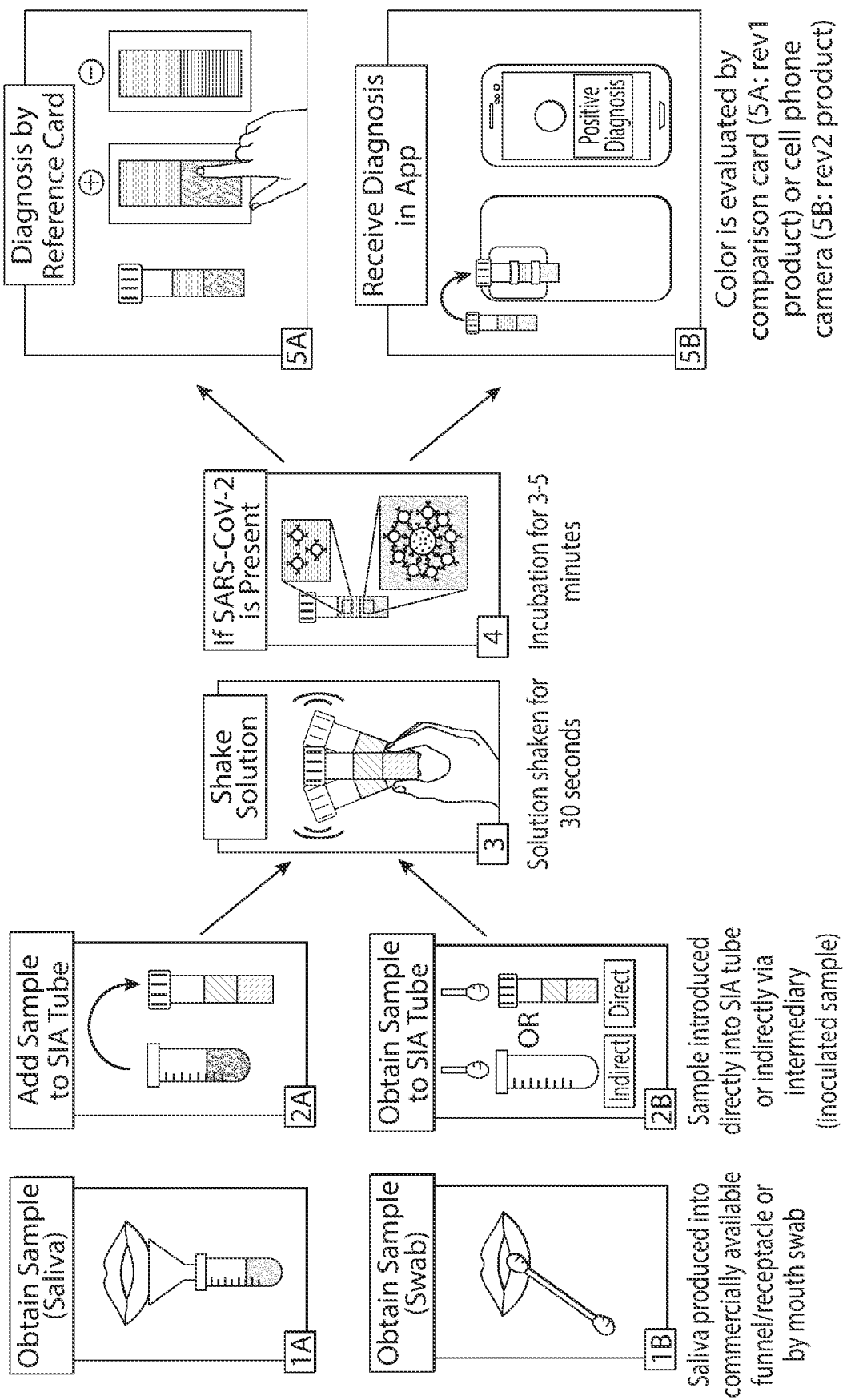
FIG. 12 illustrate additional methods of determining a virus, in yet other embodiments.

The process workflow diagram in the example of FIG. 12 represents two sample collection methodologies (panels 1 and 2) and two result/diagnosis readout methodologies (panel 5). The initial sample collection workflow will be 1B/2B. The test process itself is depicted in panels 3 and 4, which is then followed by a readout phase, for example, via simple comparison against a standard image card for positive and negative results (initial implementation in 5A), or using an automated colorimetric app in a smart phone with the reagent tube place on a clip-on device against the phone camera, etc.

A stand-alone, hand-held colorimetric device can be used to allow a simple, reader-independent detection result using rapid interrogation of the reagent tube at fixed locations corresponding to virus aggregation (below the two-phase interface) and negative control (above the interface in the top layer). A simple solid-state laser diode at fixed wavelength (650 nm) and a receiver photodiode across the tube can provide continuous absorbance kinetic information, which can be analyzed by an on-board pre-programmed electronics package. The user may receive a positive/negative virus detection result from two LED on the outside of the device to indicate a negative result or a red light to delineate a positive result. See, e.g., FIG. 1. Other implementations are of course possible in other embodiments.

The electronics package may provide Bluetooth connectivity to a smart phone for cloud uploading/registration/tracing and/or other applications. This concept is akin to the "razor blade/razor holder" model, in which a holder (the device) will be provided with each box kit of ca. 25 or 50 reagent tubes.

Aqueous two-phase partitioning (SIA) is an analytical technology in which mixtures of polymers, salts, and other additives are designed to produce separation into two distinct phases (layers), a "top phase" and a "bottom phase." While the precise phase mixtures may vary, these two phases may have different physicochemical and intermolecular solvent properties. Any solute, e.g., a virus, that is mixed with the SIA system and then allowed to equilibrate may partition between the two phases in unequal concentrations, e.g., depending on its three dimensional structure and molecular interactions within the different solvent milieus in the two phases. While the intermolecular solvent-solute interactions are very complex, the conceptual basis for SIA based assays is elegantly simple: The ratio of the concentrations of the solute between the two phases produces a numerical index partition coefficient ("K") that is specific to the aqueous partition system composition, and to the 3D structure of the solute being interrogated.

The chemistry of the system, and thus K, can be designed to exploit certain desired properties. For example, K could be made very large, such that a certain virion, e.g., SARS-CoV-2, would be found only in the bottom phase but not in the top phase of the SIA system. In this type of scenario, when another virion of different structure is present (e.g., influenza virion), that particle would then be found only in the top phase. Importantly, other assay variations can be designed to integrate scientific advances in nanotechnology. For instance, a virion bound to gold nanoparticles (AuNP) conjugated with antibodies to the SARS-CoV-2 spike protein could be designed to add unique colorimetric properties after partitioning the SARS-CoV-2 protein molecules exclusively to a particular phase of the SIA system.

AuNP conjugated to biomolecules have had a long and successful history in diagnostics in general, and in viral recognition/detection in particular. Owing to basic properties such as surface plasmon resonance (SPR), AuNP can provide unique advantages for optical signal transduction. In this example, colorimetric detection may be used due to color amplification and color change upon virion aggregation. Simply put, distance dependent changes after antibody binding to spike proteins on the virion produce a shift in optical density and/or color that can be detected and exploited, e.g., for diagnostic applications. After virion aggregation to a specific phase of the SIA system, detection of a color and/or intensity change in a specific location in the reagent tube may signify the identification of the virus due to its structure (by partitioning) and its molecular signature (by its spike protein antigen).

Two assays were used in this example, an SIA based structural recognition assay; (ii) a molecular recognition assay with colorimetric readout component. Prior to the addition of the molecular recognition component, aqueous partitioning systems are clear in color, but the interface between phases is well defined showing the two layers, each having different physicochemical properties allowing potential segregation of the virion into one or both layers.

SARS-CoV-2 was added to each of 10 tubes containing different SIA system chemistries, sealed, gently shaken, briefly spun down to settle the tubes, and then aliquots of each layer were transferred to a Vero E6 plaque assay. The following are the results (pfu) corresponding to the top and bottom layers (phases) of each of the tubes.

Figure 13A:
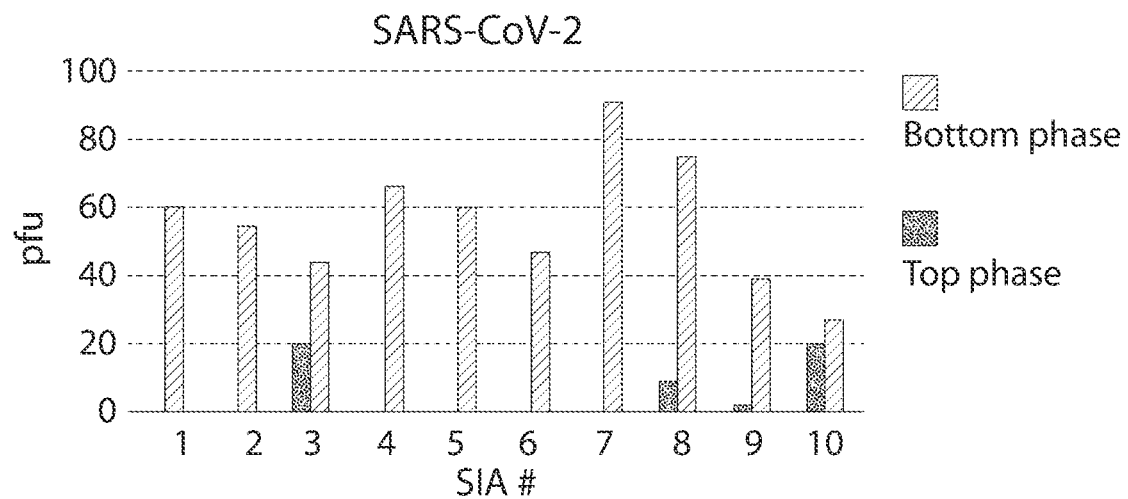
FIGS. 13A-13B illustrate that different partitioning systems can be used to separate whole CoV2 virions, in yet other embodiments.
Figure 13B:
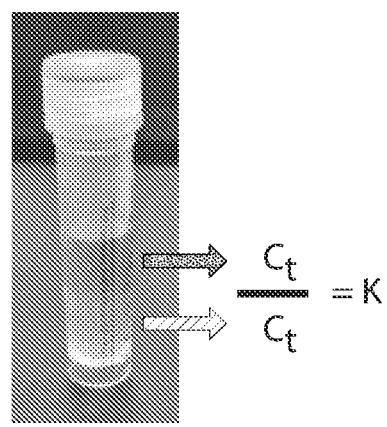

The results demonstrate that certain chemistries (e.g., numbers 1, 2, 4, 5, 6, 7) can exclude the virus completely from the top phase (left bars, most are ~0) and isolate it exclusively in the bottom phase (right bars), as is shown in FIG. 13A. This analysis provides an indication of efficient viral separation based on overall 3D conformational structure using a simple, 1-step SIA based assay system. The overall 3D structure of a virion is much less variable than its molecular structure. Because of its unique physical properties, the SIA based assay should be significantly less susceptible to frequent mutations, a signature of RNA viruses including SARS-CoV-2, that can interfere with and limit the diagnostic accuracy of molecular based diagnostic test including PCR and serology.

Following viral identification via aqueous partitioning, the readout portion of the test is performed with a well-known technique utilizing the quantum mechanical effect called surface plasmon resonance (SPR) that produces a change in color upon aggregation of gold (or other metals) nanoparticles in solution. In this example, a molecular recognition step is added by conjugating the S1 and/or S2 mAb for the SARS-CoV-2 spike protein onto the gold nanoparticles. In solution, such nanoparticles remain pink/red. Once they bind to a virion, each containing up to 200 spike proteins, the entire aggregated system will turn purple (see FIGS. 14A-14B).

The color change can be seen by the naked eye, e.g., when aided using a standardized color analysis guide card, and given that such color change is indicated at a specific location in the test tube at the bottom layer near the interface, in comparison with the negative control at the top layer. The color and intensity change can also be standardized using smart phone based colorimetry applications, which may provide accurate, real time, quantitative comparison of spectral input from the control and sample portions of the test tube simultaneously, yielding a cut-off detection readout through the smart phone application and accommodating other functionality, including data aggregation (e.g., location) as well as the integration of other information to enable index patient tracing and monitoring.

Example 6

This example demonstrates the partitioning of two different whole functional viruses, SARS-CoV-2 (CoV2) and H1N1 in a set of 11 Aqueous Two-Phase Systems (ATPS). This example shows several ATPS in which CoV2 is partitioned to one of the two aqueous phases, providing the basis for a viral diagnostics test that is based on the virus 3D structure, and not on any molecular recognition attribute such as its RNA/DNA or any envelope, spike or other surface protein. This example further shown that different viruses may partition differently in the same ATPS due to their 3D structures.

Aqueous Two-Phase Systems Preparation. A set of 11 Aqueous Two-Phase Systems (ATPS) with unique chemistry (composition described with detail in the list below) was prepared. A mixture of polymer-polymer or polymer-salt was prepared by dispensing appropriate amounts of the respective aqueous stock solutions into a 2.0 mL microcentrifuge tube using a Hamilton (Reno, NV, USA) ML-4000 four-probe liquid handling workstation. Appropriate amounts of stock solution of Sodium Phosphate Buffer (NaPB, pH 7.4), additive (sodium chloride (NaCl) or trimethylamine N-oxide (TMAO)) and water were added to give the required ionic, polymer and additive composition required for the final system with total weight of 1.4 g (total volume of ca. 1.3 mL). The prepared ATPS reagent vials were stored upright at 4° C. until use.

ATPS 1: Aqueous two-phase system was prepared with Dextran-75 (with an average molecular weight of 75,000), Polyethylene glycol PEG-8000 (with an average molecular weight of 8000), 0.15 M NaCl, and 0.01 M sodium phosphate buffer (NaPB), pH 7.4.

ATPS 2: Aqueous two-phase system was prepared with Dextran-75 (with an average molecular weight of 75,000), Polyethylene glycol PEG-8000 (with an average molecular weight of 8000), and 0.09 M NaCl, and 0.05 M sodium phosphate buffer (NaPB), pH 7.4.

ATPS 3: Aqueous two-phase system was prepared with Dextran-75 (with an average molecular weight of 75,000), Polyethylene glycol PEG-8000 (with an average molecular weight of 8000), and 0.11 M sodium phosphate buffer (NaPB), pH 7.4.

ATPS 4: Aqueous two-phase system was prepared with Dextran-40 (with an average molecular weight of 40,000), Polyethylene glycol PEG-3350 (with an average molecular weight of 3350), 0.15 M NaCl, and 0.01 M sodium phosphate buffer (NaPB), pH 7.4.

ATPS 5: Aqueous two-phase system was prepared with Dextran-40 (with an average molecular weight of 40,000), Polyethylene glycol PEG-3350 (with an average molecular weight of 3350), and 0.09 M NaCl, and 0.05 M sodium phosphate buffer (NaPB), pH 7.4.

ATPS 6: Aqueous two-phase system was prepared with Dextran-40 (with an average molecular weight of 40,000), Polyethylene glycol PEG-3350 (with an average molecular weight of 3350), and 0.11 M sodium phosphate buffer (NaPB), pH 7.4.

ATPS 7: Aqueous two-phase system was prepared with Ficoll-70 (with an average molecular weight of 70,000), Polyethylene glycol PEG-8000 (with an average molecular weight of 8000), and 0.01 M sodium phosphate buffer (NaPB), pH 7.4.

ATPS 8: Aqueous two-phase system was prepared with Ficoll-70 (with an average molecular weight of 70,000), Polyethylene glycol PEG-8000 (with an average molecular weight of 8000), 0.50 M TMAO, and 0.01 M sodium phosphate buffer (NaPB), pH 7.4.

ATPS 9: Aqueous two-phase system was prepared with Ficoll-70 (with an average molecular weight of 70,000), Polyethylene glycol PEG-8000 (with an average molecular weight of 8000), 1.00 M TMAO and 0.01 M sodium phosphate buffer (NaPB), pH 7.4.

ATPS 10: Aqueous two-phase system was prepared with Ficoll-70 (with an average molecular weight of 70,000), Polyethylene glycol PEG-8000 (with an average molecular weight of 8000), 1.50 M TMAO and 0.01 M sodium phosphate buffer (NaPB), pH 7.4.

ATPS 11: Aqueous two-phase system was prepared with Polyethylene glycol PEG-8000 (with an average molecular weight of 8000), $Na_2SO_4$ and 0.01 M sodium phosphate buffer (NaPB), pH 7.4.

Figure 15:
FIG. 15 illustrates various aqueous partitioning systems, according to one embodiment.
Figure 16:
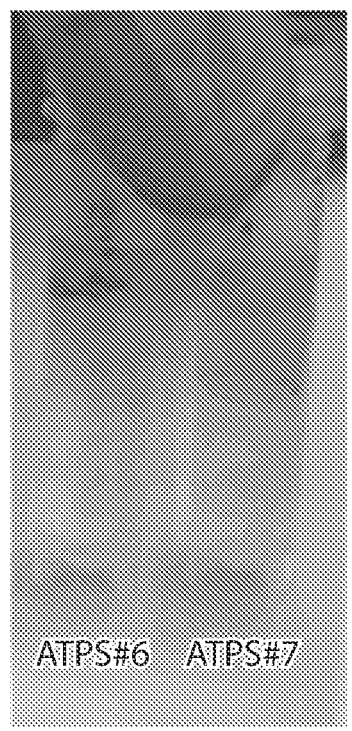
FIG. 16 illustrates maleimide functionalized AuNP-antibody conjugates in a partitioning system, in another embodiment.
Figure 17A:
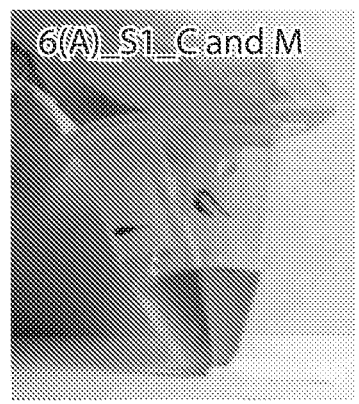
FIGS. 17A-17D illustrate maleimide functionalized AuNP-antibody conjugates, in still other embodiments.
Figure 17B:
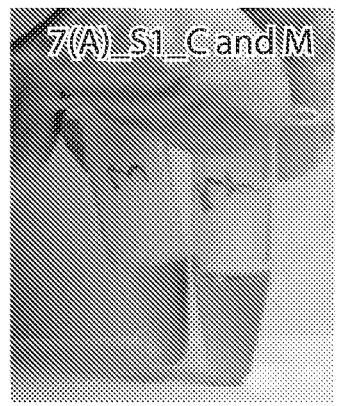
Figure 17C:
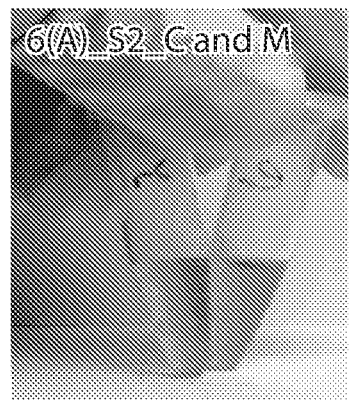
Figure 17D:
Figure 18A:
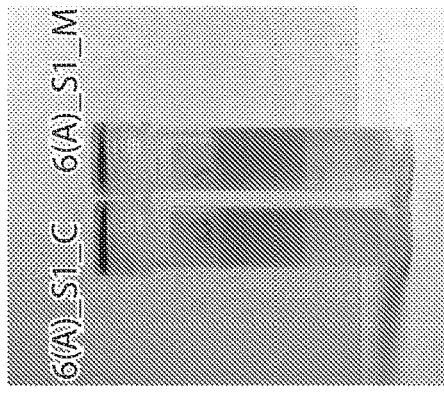
FIGS. 18A-18D illustrate various aqueous partitioning systems with viruses, according to still other embodiments.
Figure 18B:
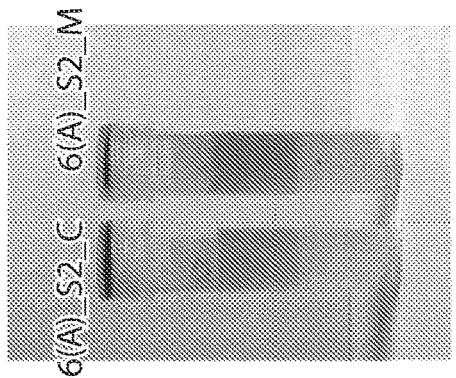
Figure 18C:
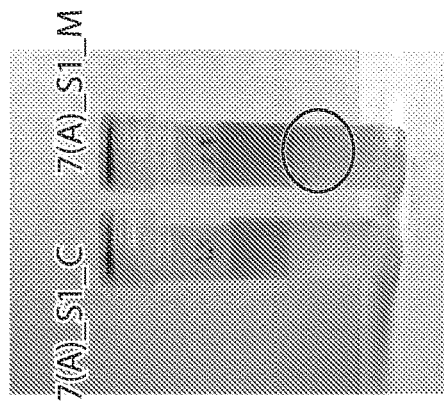
Figure 18D:
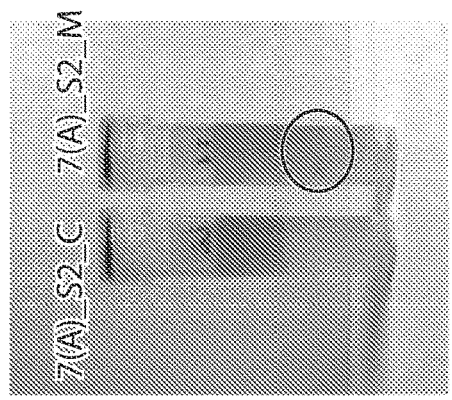

Prior to the addition of the molecular recognition component, aqueous partitioning systems were clear in color, but the interface between phases was well defined showing the two layers—each having different physicochemical properties allowing potential segregation of the virion into one or both layers. FIG. 15 shows examples of the different ATPS chemistries.

The different ATPS chemistries developed were then evaluated for their selectivity for SARS-CoV-2 virion and control virus (H1N1).

Partitioning. SARS-CoV-2 UTHSC passage 3 (SARS-Related Coronavirus 2 Isolate USA-WA1/2020) and H1N1 (PR8) were obtained. The virus and stock titer information are provided in Table 3.

TABLE 3

| Virus | Titer of stock Virus | Inoculum of Virus | Cell line for plaque assay |
|---|---|---|---|
| SARS-CoV-2 UTHSC passage 3, (SARS-Related Coronavirus 2 Isolate USA-WA1/2020) | $2 \times 10^6$ pfu/mL | $4 \times 10^4$ pfu | Vero E6 |
| H1N1 (PR8) | $1 \times 10^8$ pfu/mL | $4 \times 10^4$ pfu | MDCK |

SARS-CoV-2 and control virus (H1N1) were added to each of the 11 tubes containing different ATPS chemistries, sealed, gently mixed, briefly spun down to settle, and then aliquots of each layer were prepared and transferred to the cell line for plaque assay. The results displayed different partitioning behavior for SARS-CoV-2 and control virus (H1N1). This example further demonstrates that different partitioning systems may exhibit different levels of clinical specificity and degree of clinical differentiation power for the virions.

Table 4 shows the different partitioning behavior for both the viruses in the selected ATPS. In particular, this table shows SARS-CoV-2 and H1N1 (PR8) differential partitioning behavior determined by cell line for plaque assay (see Table 1) (*PR8 in ATPS 11 measured by $TCID_{50}$).

TABLE 4

| ATPS Systems | SARS-CoV-2 Top Phase pfu/mL | Bottom Phase pfu/mL | H1N1 (PR8) Top Phase pfu/mL | Bottom Phase pfu/mL |
| --- | --- | --- | --- | --- |
| ATPS-1 | 0 | 600 | 0 | 680 |
| ATPS-2 | 0 | 550 | 0 | 420 |
| ATPS-3 | 200 | 440 | 100 | 460 |
| ATPS-4 | 0 | 1980 | 170 | 520 |
| ATPS-5 | 0 | 600 | 230 | 370 |
| ATPS-6 | 0 | 470 | 410 | 540 |
| ATPS-7 | 0 | 910 | 60 | 570 |
| ATPS-8 | 90 | 750 | 370 | 520 |
| ATPS-9 | 60 | 390 | 570 | 670 |
| ATPS-10 | 600 | 810 | 390 | 620 |
| ATPS-11 | 60 | 4120 | $3.16 \times 10^3$ | $1 \times 10^6$ |

SARS CoV-2 was present in the bottom phase only in ATPS 1, 2, 4, 5, 6 and 7. SARS CoV-2 was present in both top and bottom phases in ATPS 3, 8, 9, 10, 11. H1N1 (PR8) was present in the bottom phase only in ATPS tubes 1 and 2 and was present in both phases in ATPS 3-11. These results demonstrate that certain chemistries (e.g., ATPS 1, 2, 4, 5, 6, 7) can exclude the virus completely from the top phase and isolate it exclusively in the bottom phase. This analysis provides a definitive indication of efficient viral separation based on overall 3D conformational structure using a simple, 1-step ATPS based assay system. Based on the plaque assay results, the systems which separated COVID-19 predominantly in the bottom phase, were used as potential candidates for next steps of experiments.

Example 7

Molecular recognition assay with colorimetric readout component. This example demonstrates an assay for visual colorimetric detection of CoV2 utilizing a combination of ATPS capable of exclusively partitioning CoV2 to one of the two aqueous phases based on its 3D structure, followed by a direct molecular identification of the virus via a monoclonal antibody conjugated to a nanoparticle-based reporting system. Many choices of the colorimetric readout system are available, and in this example, the SARS-CoV-2 spike protein S1 and S2 mAb and novel conjugation chemistries with gold nanoparticles (AuNP) for compatibility with the aqueous partitioning system were applied.

Preparation of AuNP-antibody conjugates: antibody oxidation/modification. SARS-CoV-2 (2019-nCoV) Spike Antibody, Rabbit monoclonal antibody (S1) (Part #40150-R007) was obtained from Sino Biological as a 1 mg/mL solution in phosphate buffered saline (PBS).

SARS-CoV-2 (2019-nCoV) Spike Antibody, Mouse monoclonal antibody (S2) (Part #GTX632604) was obtained from GeneTex as a 1 mg/mL solution in phosphate buffered saline (PBS).

The S1 and S2 mAb 1 mg/mL solutions were concentrated up to 4 mg/mL using an Amicon Ultra-4 centrifugal filter unit (10 kDa). The 4 mg/mL S1 and S2 mAb solutions were oxidized by incubating in 0.1 M sodium acetate, pH 5.5, and 10 mM sodium metaperiodate, pH 5.5 for 20 minutes, on ice, in the dark. After incubation, the oxidized mAb solution was diluted in and washed with 1×-PBS (pH 7.4) three times using an Amicon Ultra-15 (30 kDa) centrifugal filter unit. The oxidized mAb solution was then reduced with a solution containing PDPH and TCEP-HCl. Preparation of the PDPH/TCEP-HCl solution is as follows: 50 mg of PDPH was dissolved in 100 microliters of DMSO. TCEP-HCl was prepared at 5 mM in Milli-Q ultrapure $H_2O$. 5 microliters of the PDPH solution was added to 95 microliters of the TCEP-HCl solution and incubated for 30 minutes, at room temperature, in the dark. After incubation, the PDPH-TCEP solution was diluted 25-fold with 1×-PBS (pH 7.4.) The oxidized mAb solution was further modified by adding to the previously prepared PDHP-TCEP solution. The oxidized mAb solution was diluted approximately 2-fold with the PDPH-TCEP solution, incubated for 1 hour while shaking, at room temperature, in the dark. After incubation, the PDHP-modified mAb was washed with 10 mM sodium phosphate buffer (NaPB, pH 7.25) four times using an Amicon Ultra-15 (30 kDa) centrifugal filter unit.

mAb Conjugation to Gold Nanoparticles (AuNP). Conjugation of mAb was achieved utilizing 2 different gold nanoparticles, non-functionalized and maleimide functionalized. Both gold nanoparticles were obtained from Cytodiagnostics. Non-functionalized gold nanoparticles (Part #G-10-100) were purchased at 10 nm diameter in 0.01×-PBS. Maleimide gold nanoparticle conjugation kits (Part #MG5K-10-10) were purchased at 10 nm diameter.

Non-functionalized AuNP. For conjugation to non-functionalized AuNP's, the previously oxidized and modified S1 or S2 mAb (section 2.1.1) were diluted approximately 10-fold with 10 mM sodium phosphate buffer (NaPB), pH 7.25. This diluted mAb solution was added, while stirring, to the supplied non-functionalized AuNP solution as received and without modification. After addition, the mAb/AuNP solution was incubated for 45 minutes, at room temperature, in the dark. After incubation, the mAb/AuNP solution was collected using an Amicon Ultra-15 (30 kDa) centrifugal filter unit. The collected mAb/AuNP solution was transferred to an Eppendorf tube and centrifuged to remove any free, unconjugated antibody. Supernatant was removed and the collected mAb/AuNP pellet was resuspended in 10 mM NaPB, pH 7.25. This solution was used for further experiments in ATPS. Note: IgG-FITC conjugation to non-functionalized AuNP's, follows the same procedure described for the conjugation to non-functionalized AuNP's, the previously oxidized and modified S1 or S2 mAb.

Maleimide functionalized AuNP. For conjugation to maleimide functionalized AuNP's, the previously oxidized and modified S1 or S2 mAb was used as described above. The conjugation reaction was performed according to the supplier's protocol (Cytodiagnostics), with minor modification. After conjugation, the collected mAb/AuNP solution was transferred to an Eppendorf tube and centrifuged to remove any free, unconjugated antibody. Supernatant was removed and the collected mAb/AuNP pellet was resuspended in 10 mM NaPB, pH 7.25. This solution was used for further experiments in ATPS.

AuNP-Antibody conjugate with Aqueous Two-Phase Systems (ATPS) for the molecular detection of SARS-CoV-2: colorimetric based assay. The maleimide functionalized AuNP-Antibody conjugates were incubated with ATPS 1, 2, 4, 5, 6, and 7 (systems which shown to concentrate the COVID-19 predominantly in the bottom phase from plaque assay, see Table 4). All these systems exhibited the maleimide functionalized AuNP-antibody conjugates (appearing as a red color) in the top phase of the system. An example is shown in FIG. 16 for ATPS 6 and 7.

FIG. 16 shows maleimide functionalized AuNP-Antibody conjugates in the top phase (appearing as a red color) in ATPS 6 and 7.

For the design validation, and assuming that the ATPS systems coupled with fluorescent antibodies that specifically target surface antigens (S1 and S2) of virus particle, the following experiments (described in detail below) were executed:
 i) Partitioning of S1 or S2 spike protein in ATPS systems.
 ii) Antibody—virus interaction
 iii) AuNP conjugates—virus interaction
 iv) Virus induced separation of AuNP conjugates in ATPS Partitioning of fluorescent S1 or S2 spike protein in ATPS. The aqueous two-phase systems (ATPS) 1, 2, 4, 5, 6 and 7 were prepared as described above. The components stock solutions were dispensed by liquid handling workstation Hamilton ML-4000 into a microtube of a total volume of 1.2 mL, appropriate amount of the fluorescent S1 or S2 spike protein stock solution (10 and 5 µL of 1.0 mg/mL, respectively) and the corresponding amount (90 and 95 microliters, respectively) of water were added to a system up to a total volume of a mixture of ca. 470 microliters. The systems were vigorously shaken and centrifuged for 30 min at 3500 g in a refrigerated centrifuge with a microplate rotor with the temperature maintained at 23° C. to speed the phase settling. Microtubes were taken out of the centrifuge, and aliquots of 60 microliters from the top and the bottom phases were withdrawn and each diluted 2-fold with 10 mM sodium phosphate buffer (NaPB) pH 7.25, mixed and 200 microliters transferred to a florescent microplate. The partition coefficient for protein was determined as the ratio of the top to bottom phase concentrations and the results presented in Table 5, showing the results for fluorescent S1 or S2 spike protein partitioning.

TABLE 5

| ATPS # | FITC-S1 $K_{S1}$ | FITC-S2 $K_{S2}$ |
| --- | --- | --- |
| 1 | 0.20 | 0.11 |
| 2 | 0.20 | 0.08 |
| 4 | 1.12 | 0.51 |
| 5 | 1.79 | 0.51 |
| 6 | 3.32 | 0.74 |
| 7 | 0.02 | 0.02 |

Non-functionalized AuNP-antibody (IgG-FITC) conjugate—Spiked Antibody mixture (1:1 S1 mAb and S2 mAb)—Virus interaction. The non-functionalized AuNP-antibody (IgG-FITC) conjugate, spiked antibody mixture (1:1 S1 mAb and S2 mAb) and ATPS systems (ATPS 4, 6 and 7 were selected) were analyzed as follows.

The AuNP-antibody (IgG-FITC) conjugated reagent (appearing as a red color), once in the presence of the Spiked Antibody mixture (1:1 S1 mAb and S2 mAb), in the presence or absence of ATPS phase, has the ability to bind with the virus resulting in the significant aggregation of the particle causing the color change (red to purple); this change can be directly assessed by the naked eye or quantified by UV-vis spectroscopy.

Preparation of the ATPS vials for phase separation. Preparation of the negative controls: top or bottom phase (ATPS)+AuNP-Ab Conjugate+NaPB (No Virus). Using the micro-centrifuge tubes, the negative controls by mixing top or bottom phase of each ATPS with AuNP-Ab Conjugate reagent and NaPB were prepared as shown in Table 6.

TABLE 6

| Tube ID | ATPS ID | Phase | Phase, µL | AuNP-Ab Conjugate, µL | 0.01M NaPB, µL | Total Mixture, µL |
| --- | --- | --- | --- | --- | --- | --- |
| C_4T | 4 | Top (T) | 50 | 60 | 90 | 200 |
| C_4B | 4 | Bottom (B) | 50 | 60 | 90 | 200 |
| C_6T | 6 | Top (T) | 50 | 60 | 90 | 200 |
| C_6B | 6 | Bottom (B) | 50 | 60 | 90 | 200 |
| C_7T | 7 | Top (T) | 50 | 60 | 90 | 200 |
| C_7B | 7 | Bottom (B) | 50 | 60 | 90 | 200 |

Preparation of the positive control: AuNP-Ab Conjugate+NaPB+Spiked Antibody (Ab) Mixture+Virus (No ATPS phase). Using the micro-centrifuge tubes, prepare the positive control (C_V) by mixing the AuNP-Ab Conjugate reagent in NaPB with Spiked Antibody (Ab) Mixture and the virus (titer of stock virus: $2\times10^6$ pfu/mL SARS CoV-2s or higher), as shown in Table 7.

TABLE 7

| Tube ID | AuNP-Ab Conjugate, µL | 0.01M NaPB, µL | Spiked Ab Mixture, µL | Virus [2 × $10^6$ pfu/mL], µL | Total Mixture, µL |
| --- | --- | --- | --- | --- | --- |
| C_V | 60 | 96 | 4 | 40 | 200 |

Preparation of the test samples: top or bottom phase (ATPS)+AuNP-Ab Conjugate+NaPB+Spiked Antibody (Ab) Mixture+Virus. These were prepared by taking additional micro-centrifuge tubes and preparing the test samples (S) as indicated in Table 8. This was performed by mixing top or bottom phase of each ATPS, AuNP-Ab Conjugate reagent in NaPB, and Spiked Antibody (Ab) Mixture with the virus (titer of stock virus: $2\times10^6$ pfu/mL SARS CoV-2s or higher).

TABLE 8

| Tube ID | ATPS/phase ID | Phase, µL | AuNP-Ab Conjugate, µL | MNaPB µL | Spiked Ab Mixture, µL | Virus [2 × $10^6$ pfu/mL]µL | Total Mixture, µL |
| --- | --- | --- | --- | --- | --- | --- | --- |
| S_4T_V | 4T | 50 | 60 | 46 | 4 | 40 | 200 |
| S_4B_V | 4B | 50 | 60 | 46 | 4 | 40 | 200 |
| S_6T_V | 6T | 50 | 60 | 46 | 4 | 40 | 200 |
| S_6B_V | 6B | 50 | 60 | 46 | 4 | 40 | 200 |
| S_7T_V | 7T | 50 | 60 | 46 | 4 | 40 | 200 |
| S_7B_V | 7B | 50 | 60 | 46 | 4 | 40 | 200 |

Figure 14A:
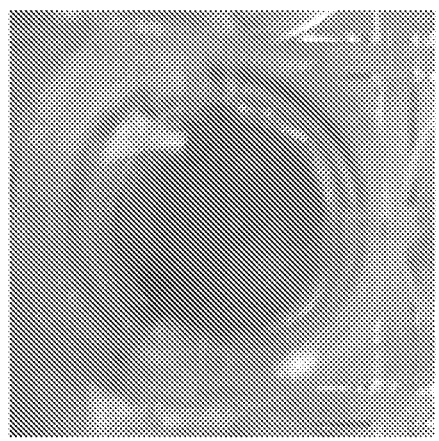
FIG. 14A-14B illustrate AuNP-antibody conjugates, in yet other embodiments.
Figure 14B:
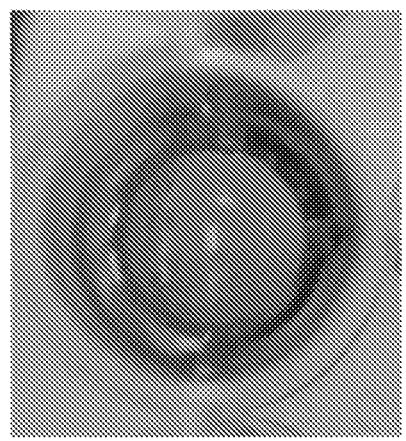

Monitoring of all the steps before and after incubation: FIGS. 14A-14B show an example for the MTP wells for non-aggregated and aggregated mixture—a change in color is observed upon aggregation of gold nanoparticles in solution. A molecular recognition was achieved by conjugating the S1 and/or S2 mAb for the SARS-CoV-2 spike protein onto the gold nanoparticles (described earlier). In solution, such nanoparticles remain pink/red. Once they bind to a virion, each containing up to 200 spike proteins, the entire aggregated system will turn purple. In particular, in FIG. 14, AuNP-antibody conjugate in MTP non-aggregated (FIG. 14A) and aggregated (FIG. 14B).

The maleimide functionalized AuNP-antibody conjugates and ATPS systems (ATPS 6 and 7 were selected) were analyzed to explore the use of the Solvent Interaction Analysis (SIA) test using Aqueous Two-Phase Systems (ATPS) with AuNP-(S1 or S2) mAb conjugate for the molecular detection of SARS-CoV-2—colorimetry read-out-based assay.

Using micro-centrifuge tubes, the controls (C) and AuNP conjugate—virus mixture (M) were prepared as indicated in Table 9 (e.g., for tube with ID 6 (A)_S1_C, 300 microliters NaPB solution were added to the tube; then 100 microliters of AuNP-S1 mAb conjugate solution were added to the tube (total of 400 microliters solution)) and mixed well (e.g., using a precision pipette with a fresh tip to mix the material).

TABLE 9

| A | Tube ID | 0.01M NaPB, μL | Virus [2 × $10^6$ pfu/mL], μL | AuNP-mAb Conjugate (S1 or S2), μL | Total, μL |
|---|---|---|---|---|---|
| Control | 6 (A)_S1_C | 300 | 0 | 100 | 400 |
| | 6 (A)_S2_C | 300 | 0 | 100 | 400 |
| | 7 (A)_S1_C | 300 | 0 | 100 | 400 |
| | 7 (A)_S2_C | 300 | 0 | 100 | 400 |
| Mixture | 6 (A)_S1_M | 200 | 100 | 100 | 400 |
| | 6 (A)_S2_M | 200 | 100 | 100 | 400 |
| | 7 (A)_S1_M | 200 | 100 | 100 | 400 |
| | 7 (A)_S2_M | 200 | 100 | 100 | 400 |

The prepared tubes (controls and mixtures) were incubated for 2 h at 37° C. The virus was reacted with the Maleimide functionalized AuNP conjugates prepared with S1 or S2 mAbs and then loaded the mixtures into the corresponding ATPS Reagent vials. Photographs of the tubes (mixtures and respective controls) side by side were taken (see FIGS. 17A-17D). Controls are shown in FIGS. 17A and 17C and the virus mixtures are shown in FIGS. 17B and 17D.

The ATPS Reagent vials of each chemistry (ATPS 6 and ATPS 7) were prepared with 400 microliters free volume, total weight of 1.4 g (after addition of the sample, see below). The tubes were labeled using matching ID of the already prepared Controls and Mixtures (see table above), mixed using the vortex for 40-60 sec at intensity 10 or Maximum intensity and the 400 microliters of sample (controls or mixtures after 1 h incubation) were dispensed into the corresponding ATPS Reagent vial.

After sample addition, the tubes were gently mixed by manual inversion 25× times until the contents appeared homogeneously cloudy and well mixed. The tubes were load into a mini centrifuge and centrifuge for 1 minute. After the centrifugation cycle, the tubes were removed from mini centrifuge and placed upright on the bench for 1 h. After 1.5 h, the ATPS Reagent vials were inspected and photograph of the tubes (mixtures and respective controls) were taken side by side. The tubes were monitored at regular time intervals by taking clear photographs (up to 2.5 hours). The images (FIGS. 18A-18D) show the photographs of the ATPS #6 and #7 after 1.5 h incubation period. The bottom phase of the tube containing the virus (_M) was more pink than its counterpart control tube (_C), indicating presence of virus that is partitioned to the bottom phase and is molecularly detected there by the AuNP-mAb system.

This example demonstrates a whole virion detection system that can not only provide for visual point-of-care confirmation of the presence of viral material in the sample, but also direct confirmation that the viral material corresponds to whole virions, the functional infective unit itself. This information has significant benefit over other detection techniques that may only report the presence of viral material itself, e.g., RNA or surface proteins, but not the presence of the whole functional virus particle itself and thus may have considerably less clinically relevant or actionable information.

Example 8

This example illustrates a COVID/SIA experimental protocol in accordance with another embodiment of the disclosure. The assay objective is to reduce RT-PCR overall false positive rate by converting its reporting solely on viral RNA content to reporting on presence of whole functional SARS-CoV-2 ("CoV2") virions in the sample.

The scientific rationale is as follows. Solvent Interaction Analysis (SIA), an analytical implementation of aqueous two-phase partitioning for clinical diagnostics application, has been demonstrated to selectively partition CoV2 whole virions into one of the two aqueous phases. See, e.g., the previous examples, and U.S. Pat. Nos. 7,968,350, 8,211,714, 8,099,242, and 9,354,229, each incorporated herein by reference in their entireties. Subsequent quantification of CoV2 viral RNA in both aqueous phases and comparison on a ratiometric index basis of samples containing functional CoV2 virions vs. those containing only viral RNA could serve as a basis using conventional statistical techniques (ROC analysis) to define an appropriate cut-off value to differentiate samples containing functional CoV2 virions from those with only viral RNA.

In FIG. 13, multiple SIA chemistries were tested for their capacity to separate whole CoV2 virions into one of the two aqueous phases, tested with standard plaque functional assay (Vero E6 cells). In the majority of the different cases tested (FIG. 13A), the virus was found only in the bottom phase, meaning that the K ratiometric index, defined as, e.g., by the ratio of $C_t$ of the top to bottom phases, would have a specific numerical value. For example, if the current cut-off value for a particular RT-PCR test is $C_t$=40, and RNA was found only in the bottom phase, with, e.g., $C_t$=25, then the ratio K=40/25=1.6 (FIG. 13B).

Since it was also to be expected that free RNA to be present in clinical samples from dead virions, any real world case would be expected to have measurable amounts of RNA in both phases. The distinction between sample containing only free RNA—with no infectivity potential—and that which contains free RNA and whole functional virions—with infectivity potential—lies in the relative amount of RNA to be expected in the bottom phase. Free RNA would be partitioned with a specific K index value independently of the overall concentration of RNA in the sample; this unique property of SIA has been verified and is the basis for other clinical assays based on SIA. Therefore, for a sample of only free RNA, one can expect to measure a K index value that will correspond to that which was previously verified in calibration experiments from patients with known clinical status, i.e., positive RT-PCR but negative infective potential by plaque or TCID50 assays. Conversely, for a sample of free RNA and whole functional virions, one can expect to measure a higher K index value, since there will be additional RNA contribution from the virions in the bottom phase, and therefore a lower $C_t$ value. Potentially the infectivity potential (viral load) could also be calibrated against the K index value in studies with known plaque of TCID50 readouts as gold-standards.

The experimental protocol is as follows:
1. Evaluate K index for free RNA:
   a. Add ca. 200 microliters of saline buffer from ca. 12 positive confirmed high $C_t$ value samples, e.g., >35, to SIA reagent tubes, shake/centrifuge per protocol, withdraw aliquots from top and bottom phases, measure $C_t$ from both phases, calculate K for each sample.
   b. Perform statistical analysis of the distribution of K and its mean, correlation with $C_t$, and other measures of association. Ideally, an average K value with tight SD would be determined independently of $C_t$ for all high $C_t$ samples to represent samples with only free RNA and thus non-infectious status. Potentially, additional verification of infectivity via plaque or TCID50 could be done on a random subset of the samples.
2. Evaluate K index for samples suspected of potential infective status:
   a. Same protocol as in 1(a), with samples selected with low $C_t$, e.g., <25 collected a few days at most following initial clinical presentation of symptoms thereby presumed to be infectious. A subset of these samples will be verified for infectivity via plaque or TCID50 and potentially viral loading vs. their $C_t$ values. K index values for each sample will be calculated.
   b. Perform statistical analysis of the distribution of K and its mean, correlation with $C_t$, and other measures of association. It is not expected that the K index will be constant as for free RNA; rather, as more viral loading is being partitioned into the bottom phase, it is expected that the index K will monotonically be increased in its numerical value.
3. Determination of diagnostics cut-off value for the index K, and potential viral load index:
   a. Following verification of statistically separable populations of the K indices corresponding to free RNA and free RNA+virions, a ROC analysis will be performed to determine a K cut-off for optimizing sensitivity/specificity performance for a desired clinical indication.
   b. Should a correlation between the index K and viral load as determined by plaque or TCID50 assays will be established, an empirical equation will be derived to predict viral load from direct measurement of K.
4. Clinical validation:
   a. Following assay development, following consultation with FDA, a clinical validation study will be conducted in preparation for EUA to the FDA.

Example 9

Figure 6A:
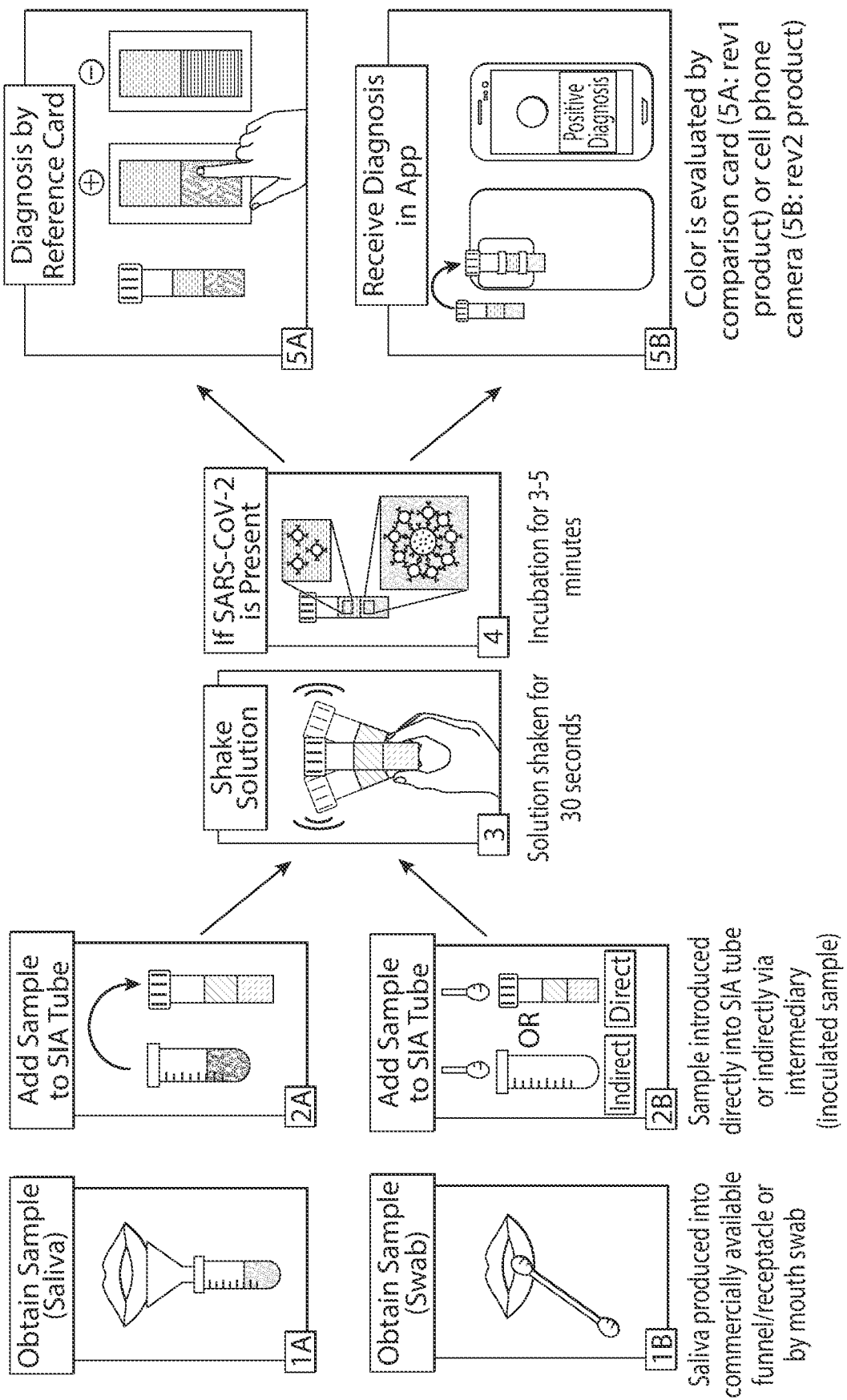
FIGS. 6A-6D illustrate yet other methods for determining a virus, in still other embodiments.
Figure 6B:
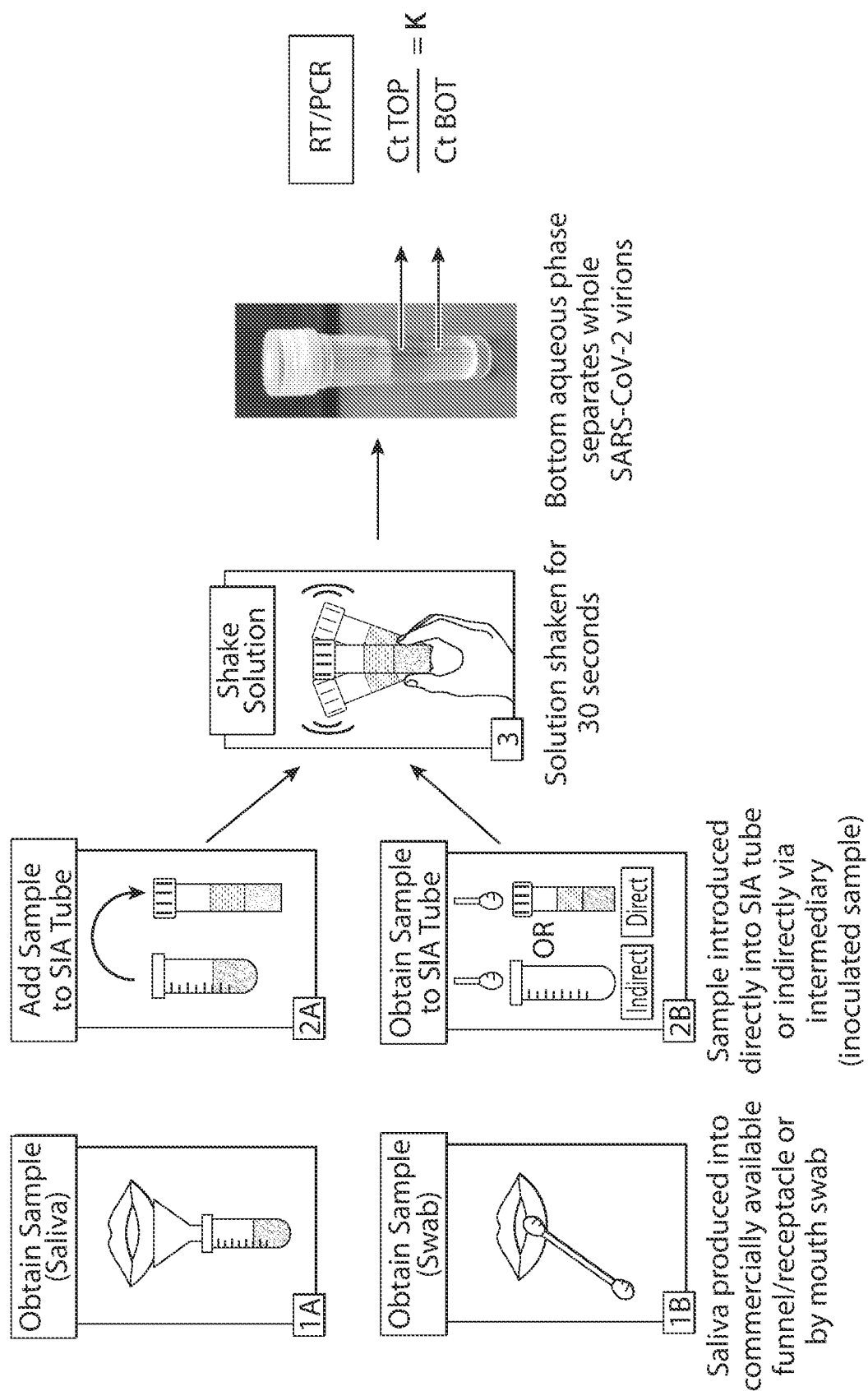
Figure 6C:
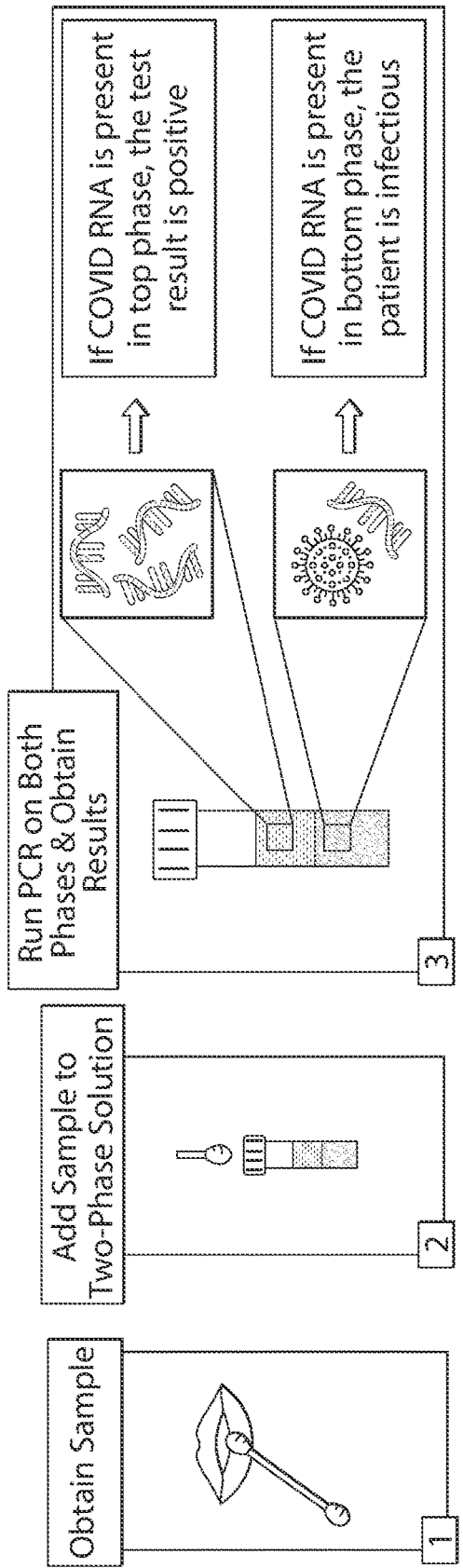
Figure 6D:
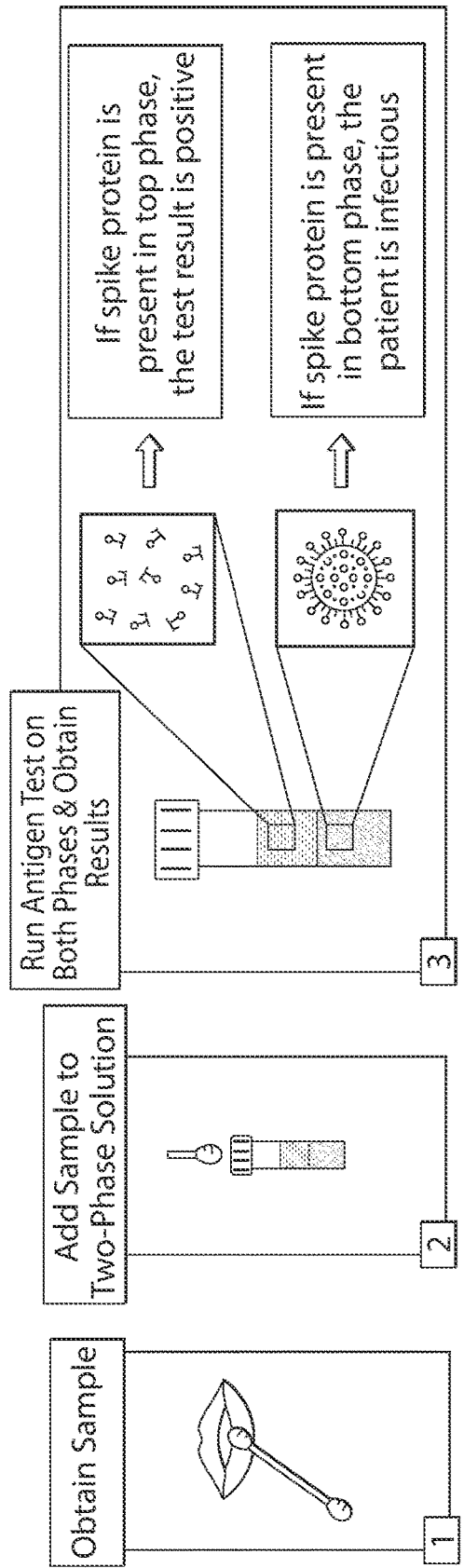

In the non-limiting example shown in FIGS. 6A-6B, the intact virion is predominantly partitioned into the bottom phase. In this example, upon RT/PCR of both the top and the bottom phases, the values of the respective cycle times, $C_t$, of the two phases can be divided to arrive at a numerical value of a partition coefficient, K. In some cases, $C_t$ may be correlated to the actual RNA concentration and K could be derived from the ratio of such concentrations. The statistical distribution of K values in the case corresponding to the presence of only viral RNA in the sample may be expected to have certain mean and dispersion parameters that could be pre-evaluated in experiments using treated virions and clinical samples with, e.g., high $C_t$ values and/or those validated otherwise via plaque or other assays to have no infective virions. If a sample contains mostly infective virions, or a mix of RNA and infective intact virions, the $C_t$ value of only the bottom phase will then be lower in this specific example since the total RNA content of only that phase will be substantially increased. The K value would then be larger than that corresponding to the mean K value for the RNA case only, and using standard statistical techniques, an appropriate cut-off value for a sample K value, denoting the presence of intact virions, may then be established and subsequently used for clinical diagnostics applications. Without restricting the generality of the present example, a non-limiting example of a diagnostics process that is able to identify not only a positive infection (disease) status of a person but also their potential for infectivity, i.e., their ability to transmit the disease to others via direct identification of the presence of whole infectious agents (e.g., virus particles, virions) in a clinical sample could be comprised of the following steps:

1. Test development:
   a. Obtain statistically significant number of clinical samples from individuals with confirmed disease state (e.g., by RT/PCR).
   b. Extract RNA from each individual sample.
   c. Partition each individual RNA in an aqueous partitioning system according to standard protocol to include mixing and phase separation/centrifugation.
   d. Withdraw aliquots from the top and bottom phases of each system
   e. Conduct RT/PCR on each phase sample and measure cycle time, Ct, or alternatively, using the assay calibration curve, measure sample concentration.
   f. Divide the top by bottom values of Ct (or concentrations) to obtain individual sample values of the partition coefficient, K.
   g. Assemble individual values of K for RNA into a statistical distribution of K values for RNA partitioning.
   h. Repeat steps a-g, moving step b to after step d, with confirmed positive samples by RT/PCR, additionally confirming presence of whole virus particles in the samples by additional functional assays such as plaque or TCID50 assays. Following the last step, there will be a second distribution of K values, this time of samples that contain whole virions in addition to free RNA.
   i. Using standard statistical discriminatory techniques, e.g., Receiver-Operating Characteristics ("ROC"), determine a suitable cut-off value for K to achieve desired sensitivity, specificity, accuracy, and other performance attributes.

2. Test Performance:
   a. Obtain a sample from an individual suspect of having a disease.
   b. Add sample to the aqueous partitioning system, mix, phase separate, remove aliquots from top and bottom phases.
   c. Conduct RT/PCR on both top and bottom phase aliquots and measure Ct or concentration and calculate K.
      i. If Ct values for both the top and bottom phases>instrument limit of quantification, sample is considered negative and the individual is considered as not having the disease.

d. Compare individual unknown sample K value to cut-off value.
   i. If Ksample>Kcut-off, the sample is considered to contain whole virus particles and the individual is considered positive for the disease and may also be contagious.
   ii. If Ksample<Kcut-off, the sample contains only RNA and the individual is considered positive for the disease.

Example 10

Figure 19:
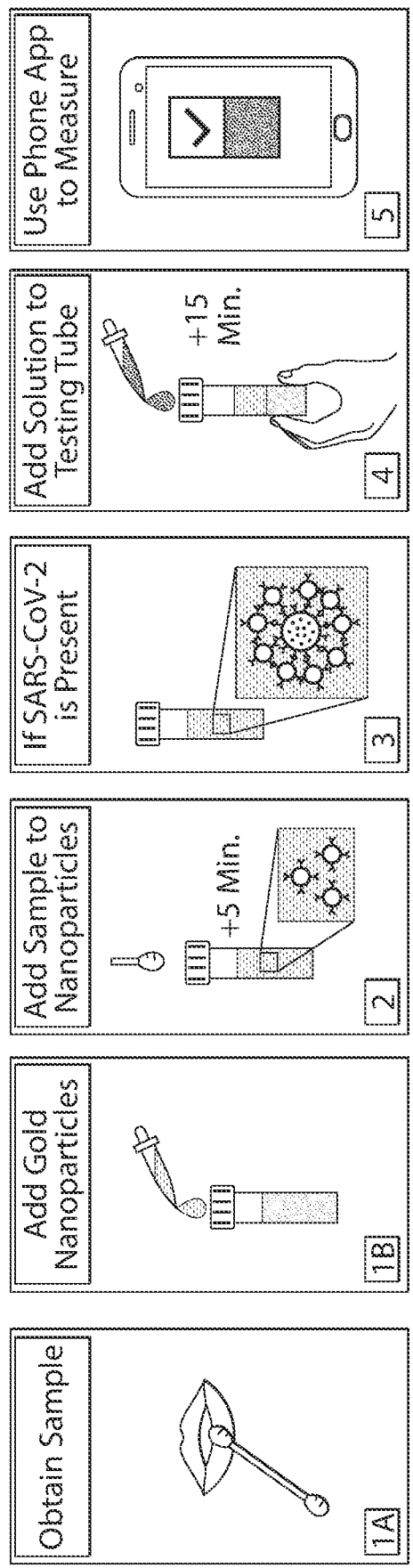
FIG. 19 illustrates a method of detecting a coronavirus, in yet another embodiment.
Figure 20:
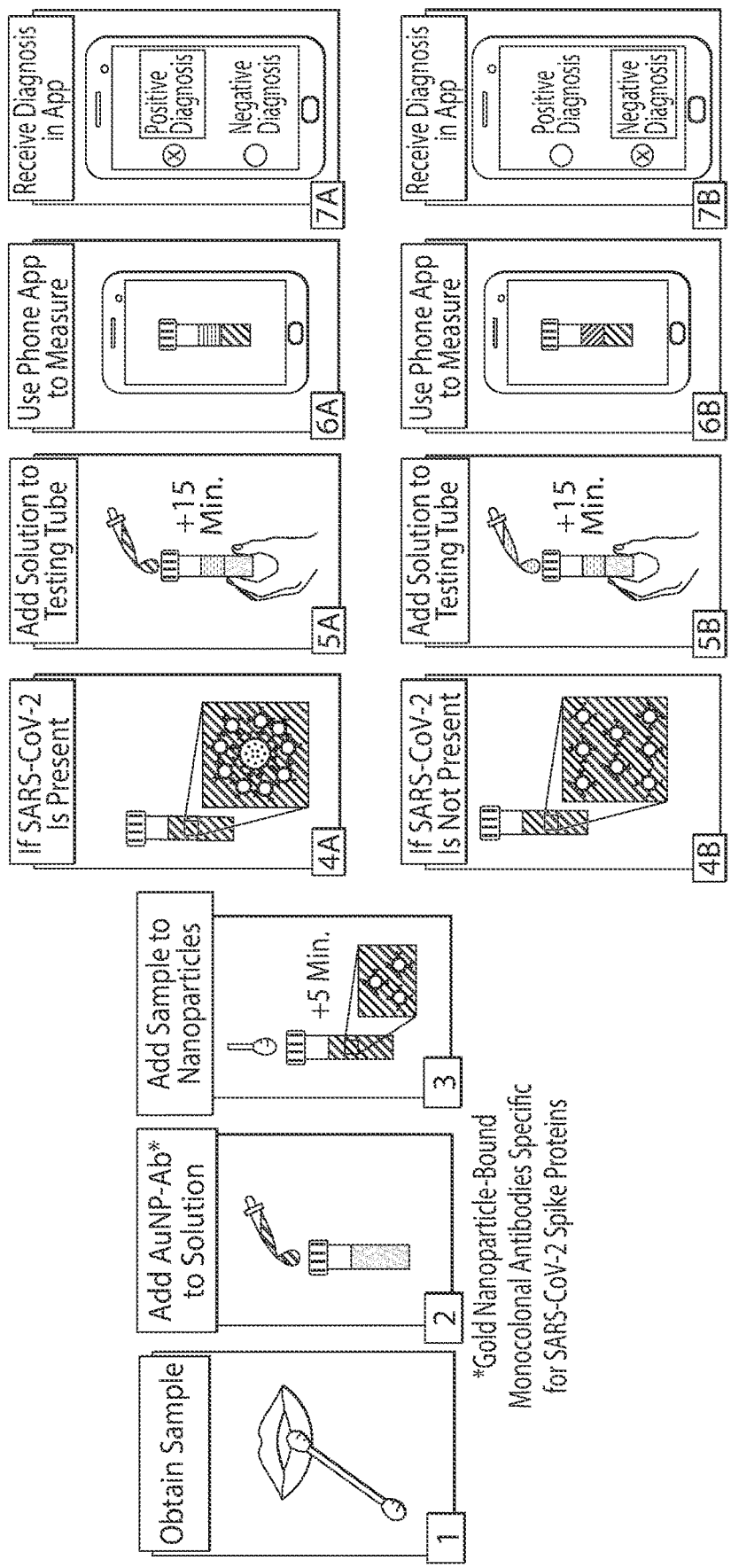
FIG. 20 illustrates another method of detecting a coronavirus, in still another embodiment.
Figure 21:
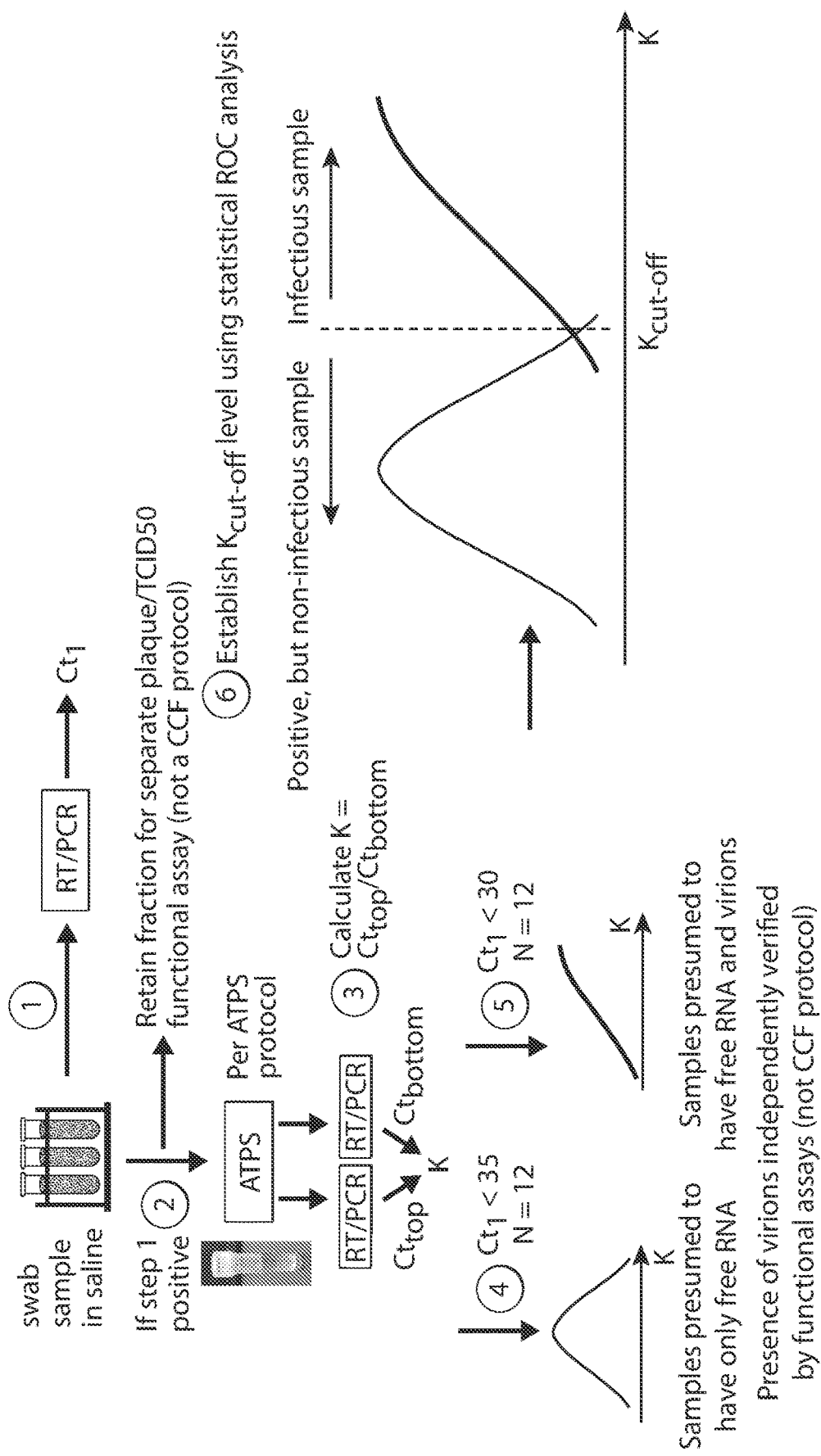
FIG. 21 illustrates a method of establishing a cut-off value for the ratiometric K value of viral samples determined using an aqueous multi-phase partition system.
Figure 22:
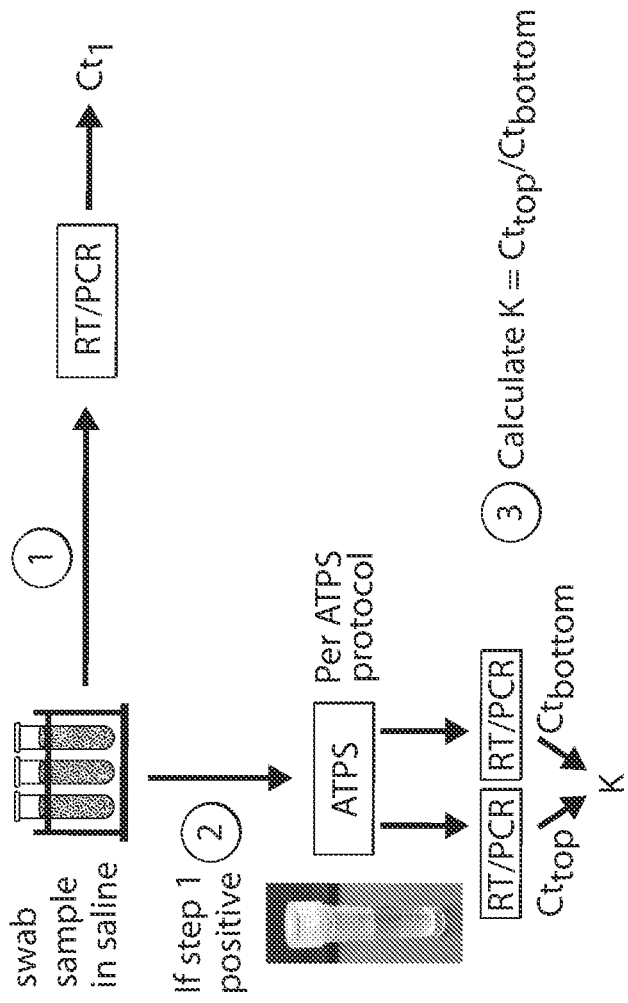
FIG. 22 illustrates a method of diagnosing a sample based on a ratiometric K index determined using an aqueous multi-phase partition system.

In this example, AuNP-Ab (gold nanoparticles with antibodies) are used for corona complex formation as primary detection system. Partitioning is used as an internal control primarily, where AuNP-Ab without virions are compared to those bound to virions in solution. When added to a partitioning system designed to partition the virion-bound AuNP complexes to the top, a red color appears on the bottom (where AuNP-Ab are present) and a purplish color appears on the top if positive (i.e., where the AuNp-Ab are bound to virions via the antibodies). A cellphone or a smartphone can be used as a colorimeter, for example, by using spectral subtraction to compare the colors or phases to determine if a virus, such as SARS-CoV-2 or another coronavirus, is present. See, e.g., FIG. 19 or 20. Other colorimeters could be used in other embodiments. In some cases, an app on the cellphone or smartphone may determine whether the virus is present, e.g., identifying a positive diagnosis if the virus is present or a negative diagnosis if the virus is not present. It should be noted that this test is relatively specific to the virus to be detected, e.g., due to the presence of antibodies specific to the virions, e.g., to a protein on the virus. Examples of such proteins include peplomers, envelope proteins, membrane proteins, nucleocapsids, spike glycoproteins, hemagglutinin-esterase dimers (HE), or the like.

Example 11

This example illustrates direct structure-based screening of SARS-CoV-2 virions for non-PCR, non-Serology POC (point of care) testing, in accordance with another embodiment. COVID-19 diagnostic testing (screening and early detection) presents multiple challenges and has specific requirements or constraints, including one or more of the following:

simple, rapid POC test format, ideally requiring little or no special equipment low-cost (especially for wide-scale screening)

assay that can readily differentiate between influenza, other highly prevalent viruses, and SARS-CoV-2 test structure that provides actionable clinical information regarding current infection (like PCR) as opposed to prior exposure (like serology)

This example illustrates the customization of a clinically validated technology (Solvent Interaction Analysis (SIA), identified as an FDA Breakthrough Device Designation for 2019 for prostate cancer) to address all of the above requirements based on differences in the structure of the virion that is specific to COVID-19, compared to other viruses, rather than molecular differences in viral RNA or on downstream generation of antibodies to the virus—the scientific modalities that underlie all current technologies. This example illustrates a test that bridges the gap between serology and PCR: a rapid POC kit requiring no additional equipment (like serology) to deliver information regarding current infection status (like PCR). This example interrogates the virion structure via its differential interaction with two adjacent aqueous environments of differing solvent properties serving as "structural reporters."

The combination of technical simplicity, POC capability and low baseline cost makes the technology described in this example specifically attractive as a widescale primary screening "filter" test prior to molecular PCR-based confirmatory testing. The same combination of advantages couples well with POC serology testing to provide complete clinical information regarding both current and past infection status.

In one embodiment, the assay kit includes a standard sample collection swab system, a 2 mL tube containing an aqueous two-phase partition system (e.g., as described herein), readout reagents (e.g., a gold nanoparticle conjugated mAb to the virion spike protein), a cellphone colorimeter application with pre-determined cut-off value to provide definitive diagnosis, and a negative internal control.

The assay focuses on two parallel paths: (i) specificity to the virion via mAb with dual negative internal controls to produce an immediate disease status based directly on virion presence, denoting active disease rather than indirectly on the presence of antibodies which primarily reflect viral exposure, and (ii) dual orthogonal specificity measures to the virion utilizing an exclusive combination of both structural (via direct classification of the virion 3D structure) and a mAb, with internal quality control. This potentially reaches PCR statistical specificity in a POC format.

One methodology is shown in FIG. 7. This example shows non-PCR, non-serology, POC testing for presence of SARS-CoV-2 virions with dual built-in-negative controls (color and location in tube). About 20 min total assay time, manual parallel operations only (simple automation possible), no instrument processing (simple cell phone app), stable reagents, low cost.

Another methodology is shown in FIG. 11. This example shows dual specificity non-PCR, non-serology, POC testing for presence of SARS-CoV-2 virions with internal quality control (color and location in tube). About 20 min total assay time, manual parallel operations only (simple automation possible), no instrument processing (simple cell phone app), stable reagents, low cost.

Aqueous two-phase partitioning (SIA) is an analytical technology in which aqueous mixtures of polymers, salts, and other additives is designed to produce separation into two distinct phases, a "top phase" and a "bottom phase." See, e.g., U.S. Pat. No. 8,211,714, 8,099,242, or 9,354,229, each incorporated herein by reference. In addition, in some cases, more than two phases and/or non-aqueous phases can also be used in some embodiments. While the precise phase mixtures will vary from application to application, these two phases will usually have different physicochemical/intermolecular solvent properties. Any solute—small or large molecule, cell, or virus—that is mixed with the system and then allowed to equilibrate may then partition between the two phases in unequal concentrations, depending on its 3D structure and molecular interactions with the different solvent structures in the two phases. While the intermolecular solvent/solute interactions can be very complex in some cases, the conceptual basis for SIA based assays is elegantly simple: The ratio of the concentrations of the solute in the two phases produces a partition coefficient ("K") specific to the aqueous partition system composition, and to the 3D structure of the solute being interrogated. The partition coefficient can thus be readily determined, without requiring any detailed knowledge of the actual intermolecular solvent/solute interactions.

The chemistry of the system, and thus K, may be designed to exploit certain desired properties. For example, K could be made very large, meaning that a certain virion, e.g., SARS-CoV-2, would be found only in the top phase but not in the bottom phase; but when another virion of different structure is present, e.g., influenza virion, it would be found only in the bottom phase. Importantly, other assay variations may be designed to integrate scientific advances in nanotechnology. For instance, a virion bound to gold nanoparticles (AuNP) conjugated with antibodies to the SARS-CoV-2 spike may be used to partition the SARS-CcV-2 protein molecules exclusively to the top phase of such partitioning system. The steps involved in a typical aqueous partition protocol are generally described by the following steps (see Step 4 in FIG. 7, or Steps 2-3 in FIG. 11):

1. Add patient sample into a small vial (typically 2 mL tube) containing ready-to-use aqueous two-phase system. Screw down the cap.
2. Shake or briefly agitate the tube.
3. Let sit for about 5 min to phase separate (15 min if AuNP-Ab incubation step is integrated with partitioning as in FIG. 7).

Depending on the assay format (e.g., as shown in FIG. 10 or 11), the analyte may be either the biological sample itself (FIG. 11) or the AuNP-Ab solution plus the biological sample (FIG. 7). Other configurations are also possible. Further, the assay readout in FIG. 7 is conducted in situ, while the readout in FIG. 11 is conducted using two additional steps—taking aliquots from the top and bottom phases of the partitioning system, e.g., using a disposable pipette, incubating with AuNP-Ab in separate tubes, and comparing the colors for a diagnosis (for example, using a cellphone application, or other suitable colorimetric detector).

Some typical assay parameters are as follows.

Sensitivity. AuNP conjugated to mAb have been amply documented to provide sensitivities down to 100 virions/mL in aggregation assays. The SARS-CoV-2 spike protein S1 and S2 mAbs can be conjugated with AuNP for compatibilities with the aqueous partitioning chemistries. Near-PCR LOQ levels can be used to allow the direct query of swab samples (typically containing >$10^3$ virus particles).

Specificity. The example assay formats shown in FIGS. 10 and 11 offer similar levels of statistical specificity. The assay shown in FIG. 7 relies on specificity due to mAb for the spike protein, while the assay shown in FIG. 11 has built-in dual orthogonal specificity "sensors"—the first being the partitioning of the SARS-CoV-2 virion to only the top phase of the partitioning system based on its 3D structure (and interaction with the two aqueous solvents), and the second being the readout specificity using mAb for SARS-CoV-2 spike protein. These offer similar assay specificity level compared to RT-PCR.

Negative Internal Control. The assay shown in FIG. 7 includes built-in internal controls via direct, automated application comparison of colors (e.g., using a cellphone, as is shown here) in the top versus bottom phases of the partitioning tube produced by the interaction of nanoparticles with the substrate analyte, essentially reporting the operational integrity of the overall assay. Similar colors (e.g., red) indicate the lack of AuNP-Ab aggregation around virions that should occur exclusively in the top phase, while dissimilar colors (e.g., purple vs. red, per pre-determined spectral cutoff within the application) can be used confirm the presence of viral-nanoparticle complexes in the top phase and a positive test result. Different colors are also possible in some cases, e.g., based on the size of the nanoparticles, or other factors). The assay shown in FIG. 11 has a separate internal control for the overall assay integrity. As the SARS-CoV-2 virions will only partition to the top phase, leaving the bottom phase to always be free of the virions, negativity in the bottom phase by incubation with AuNP-Ab following phase aliquoting can be used as a second verification.

Example operational parameters are as follows.

The total assay time may be about 20 minutes. It can also potentially be less upon assay optimization of certain kinetic steps.

Unlimited multiplexing is possible. For example, assay steps of additional assays could be conducted in parallel while incubation or other wait periods are required.

The assay can be either manual or automated. For example, manual kits for field applications can be provided. Lab automation with commercially-available robotic liquid handling for partition and sample preparation, e.g., in 96-well plates, are also possible.

The assay can be performed without complex instrumentation. In one embodiment, the only instrument needed can be a cellphone running a simple colorimeter application.

Scale-up of assays such as these are relatively easy, given that the chemistry of the partitioning system is based on water, polymers, and salts. AuNP and mAb are also both readily available from multiple sources today.

Example 12

This example illustrates a method of defining an appropriate cut-off value to differentiate saliva samples containing functional SARS-CoV-2 ("CoV2") virions from those with only viral RNA. The procedure follows the steps outlined below, and illustrated in FIG. 21.

1. Clinical samples of patients suspected of having CoV2 must be processed by RT-PCR. Next, the following steps are performed for samples that are positive by RT-PCR.
2. Samples that are positive by RT-PCR can be analyzed using Aqueous Two-Phase Systems (ATPS), for instance, as described in Example 6. Remaining fluid from the sample may be preserved for analysis by additional functional assays such as plaque or TCID50 assays.
3. For each sample, add 200 microliters of saline buffer to an SIA reagent tube as described in Example 5, and perform the ATPS protocol before withdrawing aliquots from the top and bottom phases.
4. Repeat Step 3 for at least 12 samples with $C_t$>35 (presumably containing only free RNA and not infectious virions).
5. Repeat Step 3 for at least 12 samples with $C_t$<30 (presumably containing only free RNA and not infectious virions).
6. Establish a cut-off value for the ratiometric index K using standard statistical ROC analysis techniques, according to the clinically desired false negative/positive levels.

Correlations between K-indices and the results of plaque assays and/or TCID50 assays may be used to predict viral load from direct measurement of K values.

Example 13

This example illustrates a method of diagnosing saliva samples suspected of being infected with SARS-CoV-2 ("CoV2"). The procedure follows the steps outlined below, and illustrated in FIG. 22.

1. Clinical samples of patients suspected of having CoV2 must be processed by RT-PCR. Next, the following steps are performed for samples that are positive by RT-PCR.
2. Samples that are positive by RT-PCR can be analyzed using Aqueous Two-Phase Systems (ATPS), for instance, as described in Example 6. Remaining fluid from the sample may be preserved for analysis by additional functional assays such as plaque or TCID50 assays.
3. Aliquots of the top and bottom phases should be collected and analyzed by RT-PCR.
4. The ratiometric index K should be computed for the sample and compared with a previously established cut-off value, which may be produced, e.g., by following the procedure of Example 12. If K exceeds the cut-off value, the sample contains virions and may be considered infectious. If K is below the cut-off value, the sample does not contain virions, and may be considered less infectious.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When the word "about" is used herein in reference to a number, it should be understood that still another embodiment of the disclosure includes that number not modified by the presence of the word "about."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method, comprising:
   partitioning a biological fluid in an aqueous multi-phase partitioning system, wherein the biological fluid arises from a subject suspected of being infected with a virus, and wherein the aqueous multi-phase partitioning system comprises two or more immiscible aqueous phases; and
   determining the virus in at least one phase of the partitioning system using an agent comprising a signaling moiety and a virus-binding moiety.

2. The method of claim 1, comprising determining the virus by determining the signaling moiety.

3. The method of claim 1, comprising determining the signaling moiety colorimetric ally.

4. The method of claim 1, comprising determining the signaling moiety fluorescently.

5. The method of claim 1, further comprising releasing nucleic acid from the virus.

6. A method, comprising:
   partitioning a biological fluid in an aqueous multi-phase partitioning system, wherein the biological fluid arises from a subject suspected of being infected with a virus, and wherein the aqueous multi-phase partitioning system comprises two or more immiscible aqueous phases;
   determining a nucleic acid associated with the virus in at least one phase of the partitioning system; and
   sequencing the nucleic acid.

7. A method, comprising:
   partitioning a biological fluid in an aqueous multi-phase partitioning system, wherein the biological fluid arises from a subject suspected of being infected with a virus, wherein the aqueous multi-phase partitioning system comprises two or more immiscible aqueous phases, and wherein the aqueous multi-phase partitioning system comprises an agent comprising a particle and a virus-binding moiety; and
   determining the particle within the phases of the partitioning system.

8. The method of claim 7, wherein the virus-binding moiety is able to bind to viral RNA.

9. The method of claim 7, wherein the virus-binding moiety is able to bind to a coronavirus.

10. The method of claim 9, wherein the virus-binding moiety is able to bind to a peplomer of the coronavirus.

11. The method of claim 9, wherein the coronavirus is COVID-19.

12. The method of claim 7, wherein the virus-binding moiety is able to bind to an influenza virus.

13. The method of claim 7, wherein upon binding of the virus-binding moiety to a virus, the partitioning of the agent changes.

14. The method of claim 7, wherein if the virus is present in the aqueous multi-phase partitioning system, at least 75% of the agent partitions into a single phase of the partitioning system.

15. The method of claim 7, wherein the virus-binding moiety comprises an antibody.

16. The method of claim 7, wherein the virus-binding moiety comprises a nucleic acid sequence substantially complementary to a portion of the virus's genome.

17. The method of claim 7, further comprising a targeting species able to bind to the virus.

18. The method of claim 6, wherein sequencing the nucleic acid comprises PCR.

19. The method of claim 6, comprising sequencing the nucleic acid in the at least one phase of the partitioning system.

20. The method of claim 6, wherein the aqueous multi-phase partitioning system comprises an agent comprising a binding moiety specific for the virus.

* * * * *

UNITED STATES PATENT AND TRADEMARK OFFICE
CERTIFICATE OF CORRECTION

| | | |
|---|---|---|
| PATENT NO. | : 11,988,665 B2 | Page 1 of 1 |
| APPLICATION NO. | : 17/800296 | |
| DATED | : May 21, 2024 | |
| INVENTOR(S) | : Arnon Chait et al. | |

It is certified that error appears in the above-identified patent and that said Letters Patent is hereby corrected as shown below:

In the Claims

Column 59, Lines 18-19, Claim 3 should read:
3. The method of claim 1, comprising determining the signaling moiety colorimetrically.

Signed and Sealed this
Twelfth Day of November, 2024

Katherine Kelly Vidal
*Director of the United States Patent and Trademark Office*